US012616837B2

(12) United States Patent
Dhuldhoya et al.

(10) Patent No.: US 12,616,837 B2
(45) Date of Patent: May 5, 2026

(54) METHODS AND APPARATUSES FOR EXTRACOCHLEAR STIMULATION

(71) Applicant: The Board of Trustees of the Leland Stanford Junior University, Stanford, CA (US)

(72) Inventors: Jay Dhuldhoya, Oakland, CA (US); Francis Wong, Oakland, CA (US); Peter Luke Santa Maria, Emerald Hills, CA (US); Ina Bianca Yu, Little Rock, AR (US); David Hindin, Mountain View, CA (US); Saniya Ali, Sugar Land, TX (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 387 days.

(21) Appl. No.: 18/025,886

(22) PCT Filed: Oct. 15, 2021

(86) PCT No.: PCT/US2021/055140
§ 371 (c)(1),
(2) Date: Mar. 11, 2023

(87) PCT Pub. No.: WO2022/081949
PCT Pub. Date: Apr. 21, 2022

(65) Prior Publication Data
US 2023/0338734 A1       Oct. 26, 2023

Related U.S. Application Data

(60) Provisional application No. 63/193,396, filed on May 26, 2021, provisional application No. 63/091,933, filed on Oct. 15, 2020.

(51) Int. Cl.
A61N 1/36 (2006.01)
A61N 1/05 (2006.01)

(52) U.S. Cl.
CPC ....... A61N 1/36038 (2017.08); A61N 1/0541 (2013.01)

(58) Field of Classification Search
None
See application file for complete search history.

(56) References Cited

U.S. PATENT DOCUMENTS 6,640,121 B1    10/2003   Telischi
2001/0056291 A1 *  12/2001   Zilberman  ......... A61N 1/36038
607/57

(Continued)

OTHER PUBLICATIONS

Aguila-Vinson et al, "Perception of hearing loss by graduate students of speech-Language pathology", 2004, https://pubs.asha.org/doi/pdf/10.1044/cicsd_31_F_205.*

(Continued)

*Primary Examiner* — Mallika D Fairchild
(74) *Attorney, Agent, or Firm* — LUMEN PATENT FIRM

(57) ABSTRACT

Devices and methods for extracochlear stimulation are described herein. Such devices and methods may be configured for improving hearing in a subject in need thereof in any frequency range. In some embodiments, high frequency ranges are particularly targeted by the energy delivery elements provided herein. Low frequency ranges may be amplified by an acoustic amplifier, in various embodiments. Further, an external surface of the cochlea may be minimally prepared or altered prior to or during electrode placement on the cochlear surface. Such minimal preparation may include: disrupting mucosa on the external surface of the cochlea, applying an acid to the external surface of the cochlea, or applying a tissue growth factor to the external surface of the cochlea.

9 Claims, 67 Drawing Sheets

(56)                References Cited

U.S. PATENT DOCUMENTS

| | | | |
|---|---|---|---|
| 2002/0019669 A1 | 2/2002 | Berrang | |
| 2004/0133250 A1* | 7/2004 | Ball | A61N 1/36038 |
| | | | 607/57 |
| 2005/0201574 A1* | 9/2005 | Lenhardt | A61H 23/0245 |
| | | | 381/151 |
| 2006/0015155 A1* | 1/2006 | Charvin | H04R 25/606 |
| | | | 607/57 |
| 2006/0212094 A1* | 9/2006 | Moser | A61N 1/0541 |
| | | | 607/57 |
| 2007/0005117 A1* | 1/2007 | Fritsch | A61N 1/36038 |
| | | | 607/56 |
| 2008/0033520 A1 | 2/2008 | Jolly | |
| 2008/0153070 A1 | 6/2008 | Tyler | |
| 2009/0254163 A1* | 10/2009 | Gibson | A61N 1/0541 |
| | | | 607/116 |
| 2010/0094311 A1 | 4/2010 | Jolly | |
| 2010/0174344 A1* | 7/2010 | Dadd | A61N 5/0601 |
| | | | 607/57 |
| 2011/0319907 A1 | 12/2011 | Gallegos | |
| 2016/0015975 A1* | 1/2016 | Dueck | A61N 1/0541 |
| | | | 607/57 |
| 2016/0059015 A1* | 3/2016 | Risi | A61N 1/0541 |
| | | | 607/57 |
| 2017/0094429 A1 | 3/2017 | Bervoets | |
| 2019/0167985 A1* | 6/2019 | Carlson | A61N 1/0541 |
| 2020/0139125 A1* | 5/2020 | Noble | G06T 7/12 |

OTHER PUBLICATIONS

Cosetti et al. Cochlear Implant Electrode Insertion. Operative Techniques in Otolaryngology. 2010 (21) pp. 223-232.

Banfai et al. 1986 Extracochlear Sixteen Channel Electrode System. The Chochlear Implant. Otolaryngologic Clinics of North America 19(2) May 1986 371-408.

Banfai et al. Extracochlear eight and 16 chanel cochlear implants. International Cochlear Implant Symposium 1985, pp. 118-120.

Pulec et al. Multichannel extracochlear implant. The American Journal of Otology 10(2) 1989, 84-90.

Ryu et al. How to avoid facial nerve injury in mastoidectomy. The Korean Society 2016. https://www.ncbi.nlm.nih.gov/pmc/articles/PMC5020572/ J Audiol Otol. Sep. 2016; 20(2): 68-72.

* cited by examiner

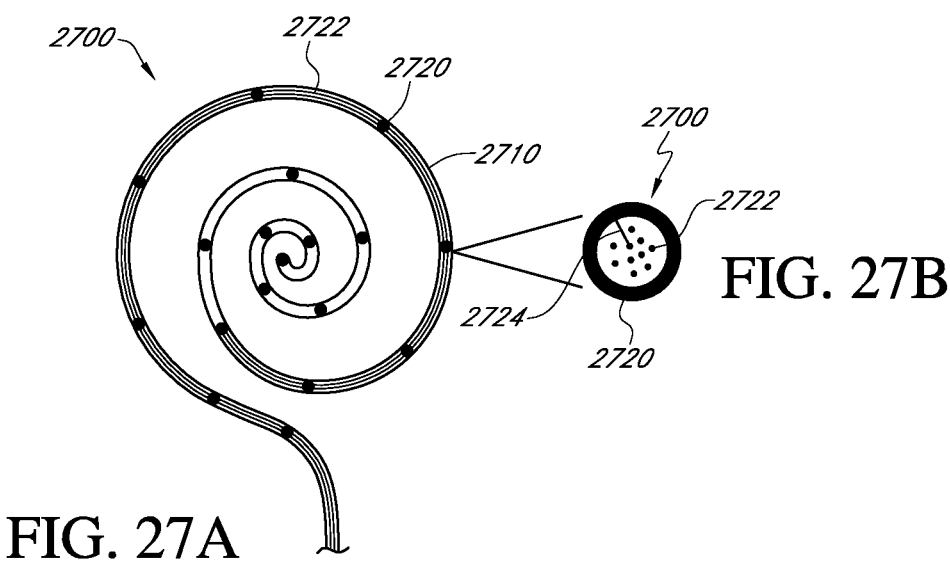
FIG. 27A
FIG. 27B
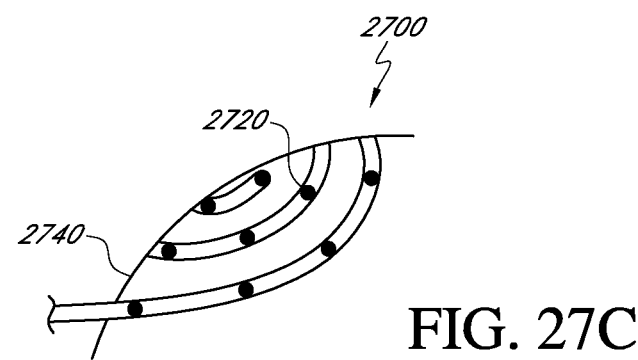
FIG. 27C
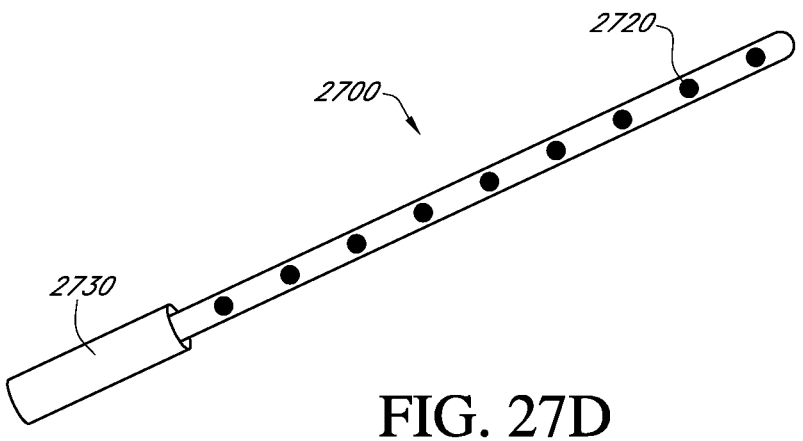
FIG. 27D

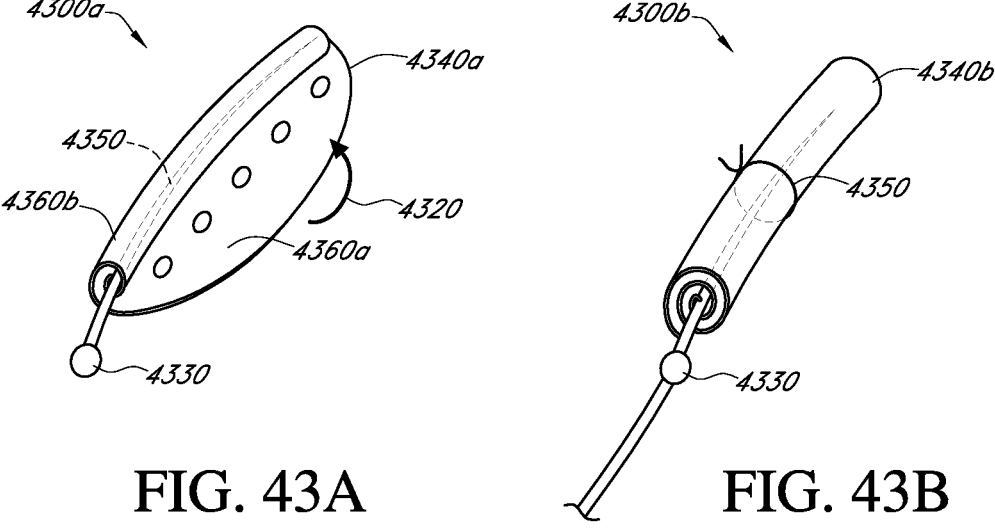
FIG. 43A          FIG. 43B
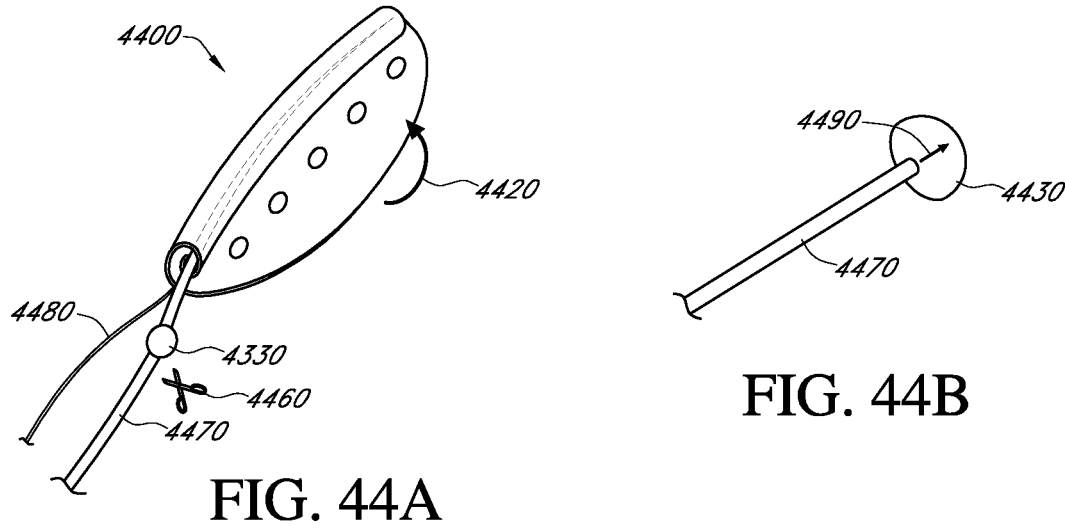
FIG. 44B
FIG. 44A

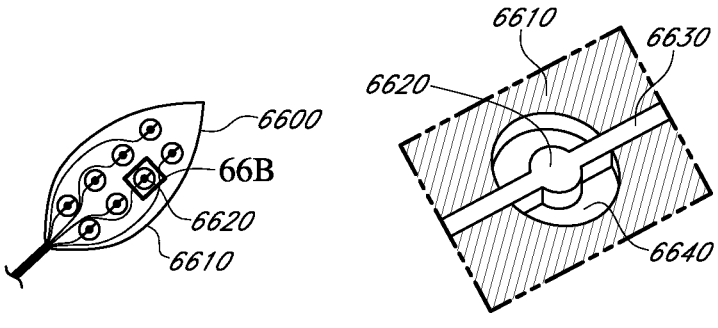
FIG. 66A          FIG. 66B
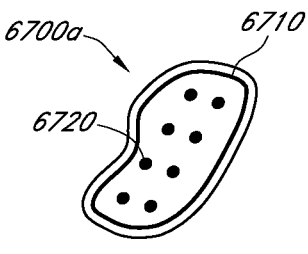         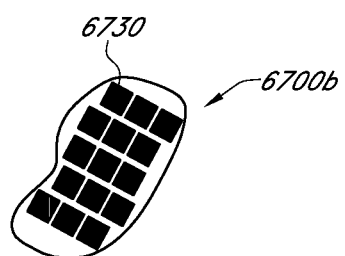
FIG. 67A          FIG. 67B
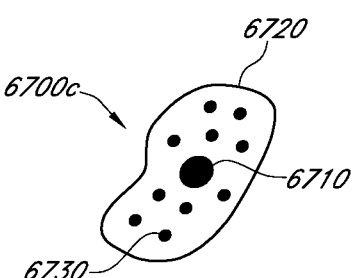
FIG. 67C

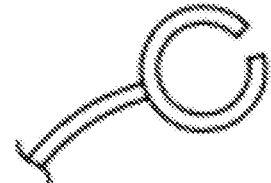
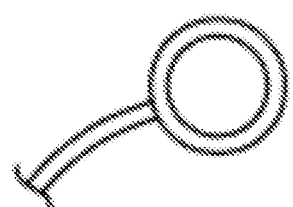
FIG. 68G　　　　　　FIG. 68H
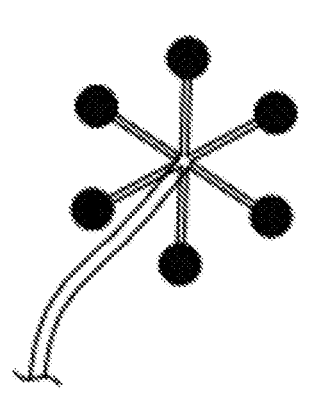
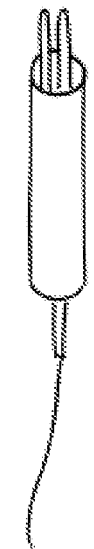
FIG. 68I　　　　　　FIG. 68J

METHODS AND APPARATUSES FOR EXTRACOCHLEAR STIMULATION

CROSS-REFERENCE TO RELATED APPLICATIONS

This application claims the priority benefit of U.S. Provisional Patent Application Ser. Nos. 63/091,933 filed Oct. 15, 2020; and 63/193,396 filed May 26, 2021; both of which are herein incorporated by reference in their entireties.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of medical device implants, and more specifically to the field of cochlear implants. Described herein are methods and apparatuses for extracochlear stimulation.

BACKGROUND

Sensorineural hearing loss is a condition estimated to affect over one third of US adults aged between 65 and 74, over half of adults over 75 years old, and over 460 million people worldwide. There are many causes of sensorineural hearing loss including aging, noise exposure, and drug-induced ototoxicity that may ultimately lead to dysfunction or loss of hair cells within the cochlea that are responsible for transducing acoustic waves to neuronal signals. It typically affects higher frequencies first and, for patients with the most severe degree of sensorineural loss where hearing aids are no longer effective, it severely impairs speech comprehension which has a profound effect on quality-of-life. These profound effects on quality-of-life include well established links to social withdrawal, isolation, depression, and dementia.

Currently, mild-to-moderate hearing loss is well treated with hearing aids, whereas severe hearing loss or severe-to-profound hearing loss is best addressed with a cochlear implant, which electrically stimulates the tonotopically arranged neurons within the cochlea. However, despite its effectiveness, a cochlear implant is considered an irreversible and invasive procedure that involves insertion of an electrode into the cochlea that often damages the delicate structures within the inner ear and carries a high risk of residual hearing loss. The only option for those with good low frequency hearing, but poor high frequency hearing, is to attempt a hybrid style cochlear implant. However, even this hybrid style comes with a high chance of residual hearing loss. This risk of residual hearing loss that occurs with placing an electrode inside the cochlea prevents many patients from considering cochlear implants as a treatment option, and so they continue to struggle with hearing aids that cannot work for their hearing loss.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 23A shows the one or more posts and FIG. 23B shows the energy delivery element coupled to the one or more posts.

FIG. 24A shows an energy delivery element for attachment to the cochlear surface. FIG. 24B shows the energy delivery element of FIG. 24A with adhesive added to one or more apertures defined by the energy delivery element.

FIG. 27A shows a deployed, coil-like configuration of an energy delivery element.

FIG. 27B shows a cross-sectional view of the array of FIG. 27A.

FIG. 27C shows the energy delivery element of FIG. 27A conformed to an external surface of the cochlea.

FIG. 27D shows a linear configuration of the energy delivery element of FIG. 27A.

FIG. 34A shows the substrate; FIG. 34B shows one embodiment of various tissue integration features of the substrate; and FIG. 34C shows another embodiment of various tissue integration features of the substrate.

FIG. 43A shows one embodiment of an energy delivery element being rolled into a compressed or unexpanded configuration.

FIG. 43B shows the energy delivery element of FIG. 43A in a fully compressed or unexpanded configuration.

FIG. 44A shows the energy delivery element of FIG. 43A tethered to a delivery tool for delivery into the middle ear cavity.

FIG. 44B shows another embodiment of tethering an energy delivery element to a delivery tool for delivery into the middle ear cavity.

FIG. 66A shows another embodiment of an energy delivery element.

FIG. 66B shows a zoomed-in view of an electrode contact of the element of FIG. 66A.

FIG. 67A-67C show various energy delivery element configurations and shapes.

FIGS. 68A-68J show various round window electrode designs.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Figure 2:
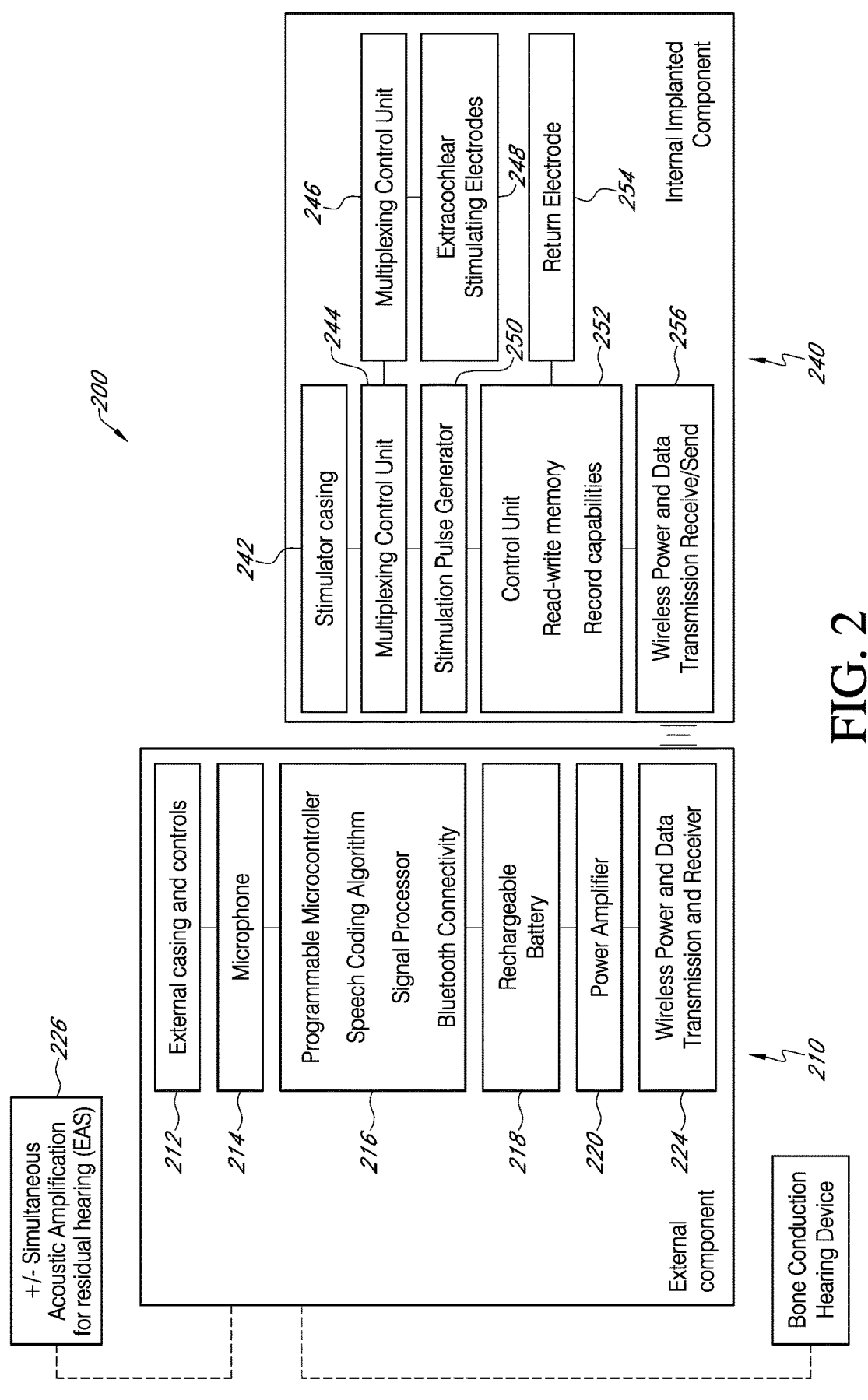
FIG. 2 shows one example of a system diagram showing the components of an extracochlear implant system.

Described herein are new approaches to improve speech understanding in patients with high-frequency hearing loss and residual low-frequency hearing. The approaches described herein address a treatment gap between hearing aids and cochlear implants in patients with useful residual hearing. Exemplary embodiments described herein include an extracochlear (outside the cochlea) electrical neurostimulation device (e.g., as shown in FIG. 2 or any of the device embodiments described elsewhere herein), that restores or improves high-frequency hearing without the risk of irreversible low frequency residual hearing loss. The embodiments described herein may also be used to suppress tinnitus as a primary benefit or as a secondary benefit, for example in patients with both high-frequency hearing loss and tinnitus in the same ear.

In certain cases, the devices described herein and associated methods, have been developed to overcome challenges, limitations, and/or failures associated with previous attempts at extracochlear stimulation for the restoration of hearing, in particular minimal improvements in speech understanding, invasive surgeries, and tissue responses (osteoneogenesis) that lead to poor device performance, device failure, and/or explantation.

Previous work in extracochlear devices attempted to treat heterogenous groups of patients, with a focus on profoundly deaf patients or patients with significant hearing loss across the full frequency range, often resulting in sub-optimal or even negative outcomes in a majority of patients that were fitted with various devices from multiple groups or labs. Multiple groups determined that extracochlear implants were inadequate for their target patient population and quickly replaced the extracochlear implants with intracochlear implants. Still others determined that extracochlear implants only improved lip reading and environmental awareness but not to the degree of improving speech understanding in a majority of patients. One study recommended extracochlear implants as an alternative to intracochlear implants only for those of a very young age or having labyrinthitis ossificans or malformations of the inner ear that would render the deaf patient unsuited for an intracochlear implant.

Figure 47:
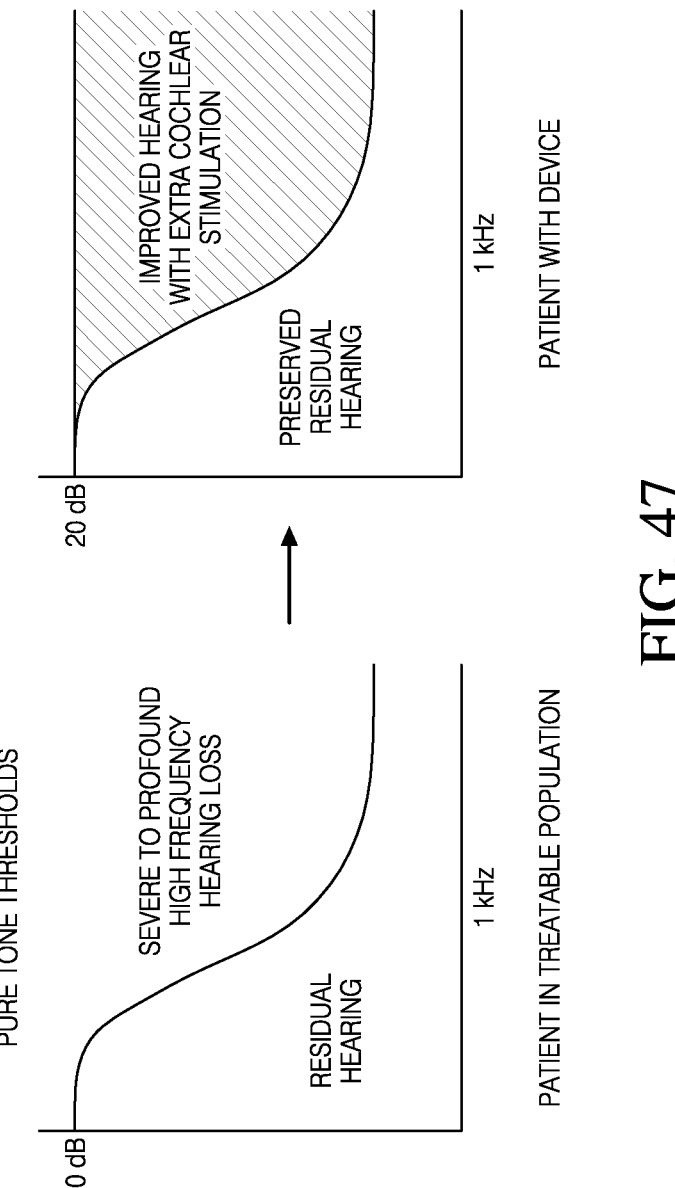
FIG. 47 shows schematics of pure tone thresholds without (left) and with (right) any one of the extracochlear devices described herein.

As described herein, improved extracochlear devices and methods of their delivery and improved methods of treatment are needed to specifically target a subset of the patient population to improve their speech understanding and substantially preserve residual hearing. Such a patient population may have or be diagnosed with severe-to-profound high frequency sensorineural hearing loss in one or both ears. As shown in FIG. 47, a target population may have residual hearing with severe-to-profound high frequency hearing loss, as shown by the sloping high frequency hearing loss shown in the left, pure tone threshold schematic. Once this target patient population is treated with any of the devices and/or methods described herein, residual hearing is preserved, or substantially preserved, while high frequency hearing is improved or even restored, as shown in the right, pure tone threshold schematic that represents a best-case scenario outcome. Severe-to-profound high frequency sensorineural hearing loss may comprise having pure tone audiometric thresholds greater than about 70 dB in a frequency range of about 2 kHz to about 8 kHz. In some cases, severe-to-profound high frequency sensorineural hearing loss may comprise having pure tone audiometric thresholds greater than about 70 dB in a frequency range of about 1.5 kHz to about 8 kHz.

Additionally, or alternatively, such a patient population may have or be diagnosed with severe high frequency sensorineural hearing loss in one or both ears. Severe high frequency sensorineural hearing loss may comprise having pure tone audiometric thresholds between about 70 dB and about 90 dB in a frequency range of about 2 kHz to about 8 kHz. In some cases, severe high frequency sensorineural hearing loss may comprise having pure tone audiometric thresholds between about 70 dB and about 90 dB in a frequency range of about 1.5 kHz to about 8 kHz.

Additionally, or alternatively, such a patient population may have or be diagnosed with profound high frequency sensorineural hearing loss in one or both ears. Profound high frequency sensorineural hearing loss may comprise having pure tone audiometric thresholds greater than about 90 dB in a frequency range of about 2 kHz to about 8 kHz. In some cases, profound high frequency sensorineural hearing loss may comprise having pure tone audiometric thresholds greater than about 90 dB in a frequency range of about 1.5 kHz to about 8 kHz.

Additionally, or alternatively, such a patient population may have or be diagnosed with moderate-to-profound high frequency sensorineural hearing loss in one or both ears. Moderate-to-profound high frequency sensorineural hearing loss may comprise having pure tone audiometric thresholds greater than about 40 dB in a frequency range of about 2 kHz to about 8 kHz. In some cases, moderate-to-profound high frequency sensorineural hearing loss may comprise having pure tone audiometric thresholds greater than about 40 dB in a frequency range of about 1.5 kHz to about 8 kHz.

Alternatively to a patient population experiencing high frequency hearing loss, the devices and methods described herein may, alternatively or additionally, be used to treat a patient diagnosed with or having moderate sensorineural hearing loss. Such a patient population may have or be diagnosed with moderate sensorineural hearing loss in one or both ears. Moderate sensorineural hearing loss may comprise having pure tone audiometric thresholds between about 40 dB and 55 dB.

Alternatively to a patient population experiencing high frequency hearing loss, the devices and methods described herein may, alternatively or additionally, be used to treat a patient diagnosed with or having moderately severe sensorineural hearing loss. Such a patient population may have or be diagnosed with moderately severe sensorineural hearing loss in one or both ears. Moderately severe sensorineural hearing loss may comprise having pure tone audiometric thresholds between about 55 dB and 70 dB.

Alternatively to a patient population experiencing high frequency hearing loss, the devices and methods described herein may, alternatively or additionally, be used to treat a patient diagnosed with or having severe sensorineural hearing loss. Such a patient population may have or be diagnosed with severe sensorineural hearing loss in one or both ears. Severe sensorineural hearing loss may comprise having pure tone audiometric thresholds between about 70 dB and 90 dB.

Alternatively to a patient population experiencing high frequency hearing loss, the devices and methods described herein may, alternatively or additionally, be used to treat a patient diagnosed with or having moderate-to-severe sensorineural hearing loss. Such a patient population may have or be diagnosed with moderate-to-severe sensorineural hearing loss in one or both ears. Moderate-to-severe sensorineural hearing loss may comprise having pure tone audiometric thresholds between about 40 dB and 90 dB.

Additionally, or alternatively, such a patient population may receive limited benefit from acoustic amplification in improving speech understanding. Limited benefit from acoustic amplification may comprise achieving less than about 60% on speech recognition scores under best-aided conditions, as measured by speech comprehension tests. In some cases, limited benefit from acoustic amplification may comprise achieving less than about 40% on speech recognition scores under best-aided conditions as measured by speech comprehension tests. In some cases, limited benefit from acoustic amplification may comprise achieving between 10% and 60% on speech recognition scores under best-aided conditions as measured by speech comprehension tests. In some cases, limited benefit from acoustic amplification may comprise achieving between 10% and 40% on speech recognition scores under best-aided conditions as measured by speech comprehension tests. In some cases, limited benefit from acoustic amplification may comprise achieving between 20% and 60% on speech recognition scores under best-aided conditions as measured by speech comprehension tests. In some cases, limited benefit from acoustic amplification may comprise achieving between 20% and 40% on speech recognition scores under best-aided conditions as measured by speech comprehension tests. Exemplary, non-limiting speech comprehension tests include: AzBio, CNC words, CNC sentences, or HINT Sentences in Noise and Quiet.

Additionally, or alternatively, such a patient population may have or be diagnosed with residual low-frequency hearing. Residual low-frequency hearing may comprise having pure tone audiometric thresholds less than about 70 dB in a frequency range of about 125 Hz to about 1 kHz. In some cases, residual low-frequency hearing may comprise having pure tone audiometric thresholds less than about 70 dB in a frequency range of about 250 Hz to about 1 kHz. In some cases, residual low-frequency hearing may comprise having pure tone audiometric thresholds less than about 70 dB in a frequency range of about 125 Hz to about 500 Hz. In some cases, residual low-frequency hearing may comprise having pure tone audiometric thresholds less than about 70 dB in a frequency range of about 250 Hz to about 500 Hz.

As used herein, residual low-frequency hearing may comprise having pure tone audiometric thresholds less than about 55 dB in a frequency range of about 250 Hz to about 1 kHz. In some cases, residual low-frequency hearing may comprise having pure tone audiometric thresholds less than about 55 dB in a frequency range of about 250 Hz to about 1 kHz. In some cases, residual low-frequency hearing may comprise having pure tone audiometric thresholds less than about 55 dB in a frequency range of about 125 Hz to about 500 Hz. In some cases, residual low-frequency hearing may comprise having pure tone audiometric thresholds less than about 55 dB in a frequency range of about 250 Hz to about 500 Hz.

As used herein, residual low-frequency hearing may comprise having pure tone audiometric thresholds less than about 40 dB in a frequency range of about 250 Hz to about 1 kHz. In some cases, residual low-frequency hearing may comprise having pure tone audiometric thresholds less than about 40 dB in a frequency range of about 250 Hz to about 1 kHz. In some cases, residual low-frequency hearing may comprise having pure tone audiometric thresholds less than about 40 dB in a frequency range of about 125 Hz to about 500 Hz. In some cases, residual low-frequency hearing may comprise having pure tone audiometric thresholds less than about 40 dB in a frequency range of about 250 Hz to about 500 Hz.

As used herein, residual low-frequency hearing may comprise having pure tone audiometric thresholds less than about 20 dB in a frequency range of about 250 Hz to about 1 kHz. In some cases, residual low-frequency hearing may comprise having pure tone audiometric thresholds less than about 20 dB in a frequency range of about 250 Hz to about 1 kHz. In some cases, residual low-frequency hearing may comprise having pure tone audiometric thresholds less than about 20 dB in a frequency range of about 125 Hz to about 500 Hz. In some cases, residual low-frequency hearing may comprise having pure tone audiometric thresholds less than about 20 dB in a frequency range of about 250 Hz to about 500 Hz.

As used herein, residual low-frequency hearing may include or be described as unaided hearing in one or both ears that is subjectively useful to that patient in their activities of daily living.

Additionally, or alternatively, such a patient population may have or be diagnosed with residual hearing. Residual hearing may include or be described as unaided hearing in one or both ears that is subjectively useful to that patient in their activities of daily living.

Additionally, or alternatively, such a patient population may have or be diagnosed with sloping high-frequency hearing loss or "ski-slope" hearing loss. Such sloping high-frequency hearing loss may be characterized by one or both ears having pure tone audiometric thresholds that are lower for the lower frequencies, typically below 1 kHz, and gradually increase toward the high frequencies creating a sloping pattern of audiometric thresholds on a pure-tone audiogram.

Such users or patients may benefit from one or more devices or methods described herein that are able to improve or restore high frequency hearing with minimal risk of damaging residual hearing, resulting in improved speech comprehension and substantially preserved residual hearing.

As used herein, improved speech comprehension may comprise an about 15-percentage point improvement in speech recognition scores at 6-months post-implantation. In some cases, improved speech comprehension may comprise an about 15-percentage point improvement in speech recognition scores at 12-months post-implantation. In some cases, improved speech comprehension may comprise an about 25-percentage point improvement in speech recognition scores at 6-months post-implantation. In some cases, improved speech comprehension may comprise an about 25-percentage point improvement in speech recognition scores at 12-months post-implantation. In some cases, improved speech comprehension may comprise a, about 40-percentage point improvement in speech recognition scores at 6-months post-implantation. In some cases, improved speech comprehension may comprise an about 40-percentage point improvement in speech recognition scores at 12-months post-implantation. In some cases, improved speech comprehension may comprise an improvement of between 15-percentage points and 40-percentage points in speech recognition scores at 6-months post-implantation. In some cases, improved speech comprehension may comprise an improvement of between 15-percentage points and 40-percentage points in speech recognition scores at 12-months post-implantation. In some cases, improved speech comprehension may comprise an improvement of between 25-percentage points and 40-percentage points in speech recognition scores at 6-months post-implantation. In some cases, improved speech comprehension may comprise an improvement of between 25-percentage points and 40-percentage points in speech recognition scores at 12-months post-implantation. Speech recognition scores are measured under best-aided conditions with speech comprehension tests such as, but not limited to, AzBio, CNC words, CNC sentences, or HINT Sentences in Noise and Quiet.

As used herein, improved speech comprehension may comprise improvements in patient reported outcome measures such as, but not limited to, EAR-Questionnaire (EAR-Q), Hearing Handicap Inventory for Adults (HHIA), and Self-Assessment of Communication (SAC).

As used herein, substantially preserved residual hearing may comprise an about 5 dB increase in pure tone audiometric thresholds from baseline at 3-months post-implantation. In some cases, substantially preserved residual hearing may comprise an about 5 dB increase in pure tone audiometric thresholds from baseline at 6-months post-implantation. In some cases, substantially preserved residual hearing may comprise an about 5 dB increase in pure tone audiometric thresholds from baseline at 12-months post-implantation. In some cases, substantially preserved residual hearing may comprise an about 10 dB increase in pure tone audiometric thresholds from baseline at 3-months post-implantation. In some cases, substantially preserved residual hearing may comprise an about 10 dB increase in pure tone audiometric thresholds from baseline at 6-months post-implantation. In some cases, substantially preserved residual hearing may comprise an about 10 dB increase in pure tone audiometric thresholds from baseline at 12-months post-implantation. In some cases, substantially preserved residual hearing may comprise an about 15 dB increase in pure tone audiometric thresholds from baseline at 3-months post-implantation. In some cases, substantially preserved residual hearing may comprise an about 15 dB increase in pure tone audiometric thresholds from baseline at 6-months post-implantation. In some cases, substantially preserved residual hearing may comprise an about 15 dB increase in pure tone audiometric thresholds from baseline at 12-months post-implantation. In some cases, substantially preserved residual hearing may comprise between 5 dB and 10 dB increase in pure tone audiometric thresholds from baseline at 3-months post-implantation. In some cases, substantially preserved residual hearing may comprise between 5 dB and 10 dB increase in pure tone audiometric thresholds from baseline at 6-months post-implantation. In some cases, substantially preserved residual hearing may comprise between 5 dB and 10 dB increase in pure tone audiometric thresholds from baseline at 12-months post-implantation. In some cases, substantially preserved residual hearing may comprise between 5 dB and 15 dB increase in pure tone audiometric thresholds from baseline at 3-months post-implantation. In some cases, substantially preserved residual hearing may comprise between 5 dB and 15 dB increase in pure tone audiometric thresholds from baseline at 6-months post-implantation. In some cases, substantially preserved residual hearing may comprise between 5 dB and 15 dB increase in pure tone audiometric thresholds from baseline at 12-months post-implantation. In some cases, substantially preserved residual hearing may comprise between 10 dB and 15 dB increase in pure tone audiometric thresholds from baseline at 3-months post-implantation. In some cases, substantially preserved residual hearing may comprise between 10 dB and 15 dB increase in pure tone audiometric thresholds from baseline at 6-months post-implantation. In some cases, substantially preserved residual hearing may comprise between 10 dB and 15 dB increase in pure tone audiometric thresholds from baseline at 12-months post-implantation.

Improved devices, as shown elsewhere herein, are configured to selectively improve or restore hearing in a frequency range of about 2 kHz to about 8 kHz, or in some cases, in a frequency range of about 1.5 kHz to about 8 kHz, or in some cases, in a frequency range of about 1 kHz to about 8 kHz, or in some cases, in a frequency range of about 2 kHz to about 6 kHz, or in some cases, in a frequency range of about 1.5 kHz to about 6 kHz, or in some cases, in a frequency range of about 1 kHz to about 8 kHz. In some embodiments, as shown elsewhere herein, improved devices are configured to conform to a surface overlying the basal turn of the cochlea. Further, at least in some embodiments, the cochlea undergoes minimal processing, surgical manipulation, and/or preparation to substantially preserve the structure of the cochlea, as described elsewhere herein. Further still, in some instances, an energy delivery device may be delivered through a facial recess, a transcanal approach, or a combination thereof, as described elsewhere herein.

In general, the devices, for example electrode arrays (also referred elsewhere herein as energy delivery elements), described herein and associated methods, may be configured or adapted to attach to any tissue surface. For example, electrode arrays may be attached to a bone surface and configured to apply electrical stimulation to promote bone healing. In another embodiment, the electrode arrays described herein may be configured to attach to a skin surface for peripheral nerve stimulation. In still another embodiment, the electrode arrays described herein may be configured for retinal stimulation.

In general, the devices, for example energy delivery elements, described herein and associated methods, may be configured or adapted to be placed in any internal cavity. For example, electrode arrays may be placed within a sinus cavity and configured to apply electrical stimulation to reduce polyp growth.

The energy delivery elements, as described herein and in some embodiments, may be configured to stimulate auditory neurons in a cochlea. As described herein, auditory neurons may comprise neurons with peripheral processes that synapse with inner hair cells of the cochlea, neurons with peripheral processes that synapse with outer hair cells or the cochlea, spiral ganglion neurons, or a combination of the above.

In general, the devices described herein may comprise an electrode or an electrode array attached to an outer surface of the cochlea. In some embodiments, the electrode or electrode array is configured to attach to an area of the middle ear called the promontory that overlies the outer surface of the cochlea responsible for high-frequency hearing. The electrode array delivers targeted electrical stimuli through the bony wall of the promontory to activate the spiral ganglion neurons and improve or restore high-frequency hearing. In some embodiments, the energy delivery element does not require significant structural alteration of the cochlea, such that residual hearing is preserved. In some embodiments, the energy delivery element does not require significant structural alteration of the cochlea, such that implantation is reversible. In some embodiments, the energy delivery element does not require significant structural alteration of the cochlea, such that implantation is less invasive than existing methods.

As described herein, in at least some of the embodiments, the energy delivery elements are configured to transmit electrical stimuli to auditory neurons within the cochlea (much like an intracochlear implant). However, unlike an intracochlear implant, which is inserted into the cochlea, the energy delivery elements described herein may be positioned external to the cochlea and transmit electrical stimuli through the cochlear bone (i.e., extracochlear implant). The devices described herein, which may be positioned external to the cochlea, greatly reduce the risk of one of the major complications of cochlear implantation—loss of residual hearing due to damage of the internal structures of the cochlea. Additionally, by being positioned external to the cochlea, the devices described herein may allow for future adoption of another hearing loss treatment (including the future insertion of an intracochlear implant).

In any of the embodiments described herein, an energy delivery element may comprise an electrode array, an electrical contact, an electrode, an extracochlear implant, one or more electrical conductors, or the like that is configured to deliver energy to a surface, structure, tissue, or the like.

Users or patients described herein may benefit from one or more devices described herein that are able to improve or restore high frequency while preserving residual hearing, thereby improving speech understanding.

Any of the devices described herein may be configured to substantially maintain the structural integrity and/or outer structural surface of the cochlea (e.g., does not require delamination, significant bone removal, etc.) in order to: preserve residual hearing post-implantation, prevent osteo-neogenesis post-implantation, prevent adverse tissue response post-implantation, prevent fibrotic tissue growth post-implantation, and/or reduce invasiveness of implantation. In some embodiments, any of the devices described herein may be configured to alter the mucosal layer overlying bony tissue within the middle ear cavity while keeping the bony tissue intact. In some embodiments, any of the devices described herein may be configured to selectively remove regions of the mucosal layer overlying bony tissue within the middle ear cavity while keeping the bony tissue intact.

Any of the devices described herein may be configured to be attached to tissues within the middle ear cavity. For example, in some embodiments, attachment comprises establishing and maintaining electrical communication between the device and a tissue of the middle ear cavity. In some embodiment, attachment comprises establishing and maintaining electrical communication for more than 30 days. For example, in some embodiments, attachment of the energy delivery element to a tissue within the middle ear cavity may include one or more of: adhesive, mechanical anchoring (e.g., screws), pressure (e.g., expandable materials, springs, posts, etc.), chemical application, materials or devices that promote tissue ingrowth, hook-and-loop fasteners (i.e., Velcro®), or a combination thereof.

Any of the devices described herein may be configured to be used in combination with low frequency hearing amplification. For example, the devices described herein may enhance a patient's high frequency hearing through electrical stimulation while enhancing low-frequency hearing through acoustic amplification. In another embodiment, the devices described herein may enhance a patient's high frequency hearing through electrical stimulation while enhancing low-frequency hearing through bone conduction. In another embodiment, the devices described herein may provide high-frequency speech information through electrical stimulation while enhancing low-frequency hearing with acoustic amplification. In another embodiment, the devices described herein may provide high-frequency speech information through electrical stimulation while enhancing low-frequency hearing through bone conduction.

For example, high frequency hearing may include hearing sensitivity in one or both ears of a patient in frequencies above 1 kHz, or in some cases above 1.5 kHz, or in some cases above 2 kHz, or in some cases between 1 kHz and 8 kHz, or in some cases between 1.5 kHz and 8 kHz, or in some cases between 2 kHz and 8 kHz, or in some cases between 1 kHz and 6 kHz, or in some cases between 1.5 kHz and 6 kHz, or in some cases between 2 kHz and 6 kHz, or in some cases between 1 kHz and 4 kHz, or in some cases between 1.5 kHz and 4 kHz, or in some cases between 2 kHz and 4 kHz.

Further, for example, low frequency hearing may include hearing sensitivity in one or both ears of a patient in frequencies below 1 kHz, or in some cases below 1.5 kHz, or in some cases below 2 kHz, or in some cases between 125 Hz and 2 kHz, or in some cases between 250 Hz and 2 kHz, or in some cases between 500 Hz and 2 kHz, or in some cases between 125 Hz and 1.5 kHz, or in some cases between 250 Hz and 1.5 kHz, or in some cases between 500 Hz and 1.5 kHz, or in some cases between 125 Hz and 1 kHz, or in some cases between 250 Hz and 1 kHz, or in some cases between 500 Hz and 1 kHz.

Further, for example, high frequency speech information may include speech sounds that are perceived at frequencies above 1 kHz, or in some cases above 1.5 kHz, or in some cases above 2 kHz, or in some cases between 1 kHz and 8 kHz, or in some cases between 1.5 kHz and 8 kHz, or in some cases between 2 kHz and 8 kHz, or in some cases between 1 kHz and 6 kHz, or in some cases between 1.5 kHz and 6 kHz, or in some cases between 2 kHz and 6 kHz, or in some cases between 1 kHz and 4 kHz, or in some cases between 1.5 kHz and 4 kHz, or in some cases between 2 kHz and 4 kHz.

In any of the embodiments described herein, the system may also include an acoustic amplification system that can communicate and synchronize with the extracochlear implant system for use in patients that would benefit from both electrical stimulation and acoustic amplification. In any of the embodiments described herein, the system may also be coupled with an acoustic amplification system that can communicate and synchronize with the extracochlear implant system for use in patients that would benefit from both electrical stimulation and acoustic amplification. In any of the embodiments described herein, the system may also include a bone anchored hearing device that can communicate and synchronize with the extracochlear implant system for use in patients that would benefit from both electrical stimulation and acoustic amplification. In any of the embodiments described herein, the system may also be coupled with a bone anchored hearing device that can communicate and synchronize with the extracochlear implant system for use in patients that would benefit from both electrical stimulation and acoustic amplification.

One embodiment of a bone anchored hearing device may include a piezoelectric transducer that is configured to amplify low frequencies through bone conduction. The transducer may be positioned on the cochlea, for example the promontory, in proximity to any of the energy delivery elements described herein. In some embodiments, a substrate of the energy delivery element further supports the transducer. Alternatively, in some embodiments, the energy delivery element and the transducer are on separate substrates.

The electrode array of some embodiments may be part of a system including a transmitter/receiver (e.g., implanted under the skin behind the ear, positioned external to the ear, etc.), an external microphone, power source, and processing unit (e.g., speech processor). Such devices may be configured to transform external auditory stimulus captured through a microphone into energy applied to the neurons within the cochlea, thus improving or restoring hearing. In embodiments where parts of the system are externalized, the implantable and external components may connect and communicate via the receiver/transmitter.

In some embodiments, one or more system components described herein may: deliver electrical energy to the spiral ganglion through the cochlear bone; include one or more electrode arrays, electrical stimulator, and receiver/transmitter or any combination of two out of three components; be assembled as a unitary body; be assembled in-situ, for example, with an interconnect system running through the facial recess, under the auditory canal, or through another access point (e.g., eustachian tube); may communicate wirelessly with the other implanted components; communicate wirelessly with the external hardware; be biocompatible and intended for long-term use (e.g., months to years); and/or be entirely removed post-implantation without causing additional hearing loss.

For example, in some embodiments, any of the devices described herein may comprise an antenna, for example a mid-field antenna. The antenna may eliminate the need for a lead between the energy delivery element and the external hardware. Additionally, or alternatively, any of the devices described herein may comprise a local stimulator and/or control unit.

In some embodiments, any of the devices described herein may comprise additional sensors such as, but not limited to: an accelerometer, an inertial measurement unit, or a light sensor. In some embodiments, additional sensors may be used to provide additional inputs to the device that may affect device function. For example, in some embodiments, an accelerometer may be used to detect when a user is asleep and may trigger the device to turn off when the user is asleep. Further, for example, in some embodiments, a light sensor may be used to detect when a user is asleep and may trigger the device to turn off when the user is asleep. Further, for example, in some embodiments, an inertial measurement unit may be used to detect when a user is exercising and may trigger the device to adjust the stimulation parameters.

In some embodiments, the energy delivery elements described herein may be positioned within the middle ear cavity external to the cochlea. In certain examples, the energy delivery element may make contact with the cochlear promontory and surrounding tissue. In certain examples, the energy delivery element may not make direct contact with the cochlear promontory and surrounding tissue. In some embodiments, the energy delivery element may be positioned in the middle ear anterior to the round window and posterior to the Eustachian tube. In some embodiments, the energy delivery element may be positioned on a medial wall of the middle ear. In some embodiments, the energy delivery element may be positioned on a medial wall of the middle ear overlying the basal turn of the cochlea. In some embodiments, the energy delivery element may be positioned in a round window niche. In some embodiments, the energy delivery element may make contact with a round window membrane. In some embodiments, the energy delivery element may not make direct contact with a round window membrane. In some embodiments, the energy delivery element may be positioned underneath a round window niche membrane (mucosa covering the round window niche). In some embodiments, the energy delivery element may extend into a hypotympanum. In some embodiments, the energy delivery element may extend into an epitympanum. In some embodiments, the energy delivery element may be positioned within a facial recess. In some embodiments, the energy delivery element may be positioned within a mastoid cavity. In some embodiments, the energy delivery element may be positioned near a Eustachian tube orifice. In some embodiments, the energy delivery element may contact multiple areas within the middle ear cavity simultaneously.

In some embodiments, the energy delivery elements described herein may occupy an area less than about 20 mm by about 20 mm; less than about 10 mm by about 10 mm; less than about 8 mm by about 8 mm; less than about 6 mm by about 6 mm; less than about 4 mm by about 4 mm; less than about 2 mm by about 2 mm; less than about 1 mm by about 1 mm; etc. In some embodiments, the area occupied by the energy delivery element may be chosen depending on the method of positioning within the middle ear cavity and/or desired contact with the tissue or bone (e.g., cochlear promontory) or surrounding tissue.

In some embodiments, any of the energy delivery elements described herein may have a thickness of less than about 10 mm; less than about 5 mm; less than about 2 mm; less than about 1 mm; less than about 0.5 mm; less than about 0.1 mm; between about 0.01 mm and about 10 mm; between about 0.01 mm and about 5 mm; between about 0.01 mm and about 2 mm; between about 0.01 mm and about 1 mm; between about 0.01 mm and about 0.5 mm; between about 0.1 mm and about 5 mm; between about 0.1 mm and about 2 mm; between about 0.1 mm and about 1 mm; etc. The thickness of the array or substrate may be chosen based on the anatomy of the surrounding tissue and/or cavity. The thickness of the array or substrate may be chosen to fit the space within the middle ear cavity, for example and may be personalized based on an anatomy of the subject or imaging data. The thickness of the array or substrate may be chosen based on the desired flexibility and/or conformability of the array. The thickness of the array may be representative of an overall thickness of the array or a thickness of the substrate of the array. In one embodiment, the thickness represents a maximum thickness of the overall array or the substrate.

Any of the energy delivery elements described herein may be configured to establish and maintain electrical contact with the selected tissue, for example the tissue of the cochlear promontory and surrounding structures throughout the duration of implantation.

Any of the energy delivery elements described herein may be configured to deliver electrical stimuli with spatial selectivity in order to achieve tonotopic stimulation of auditory neurons within the cochlea. In some embodiments, such stimulation is selective for the higher frequencies, for example above about 500 Hz; above about 1 kHz; above about 1.5 kHz; above about 2 kHz; etc. In some embodiments, the range of tonotopic stimulation may be chosen to reflect the needs of the patient population or personalized based on patient needs.

In some embodiments, an energy delivery element described herein may comprise between about 1 and about 1,000 individual electrical contacts; between about 1 and about 100 individual electrical contacts; between about 1 and about 50 individual electrical contacts; between about 1 and about 36 electrical contacts; between about 1 and about 25 individual electrical contacts; between about 1 and about 16 individual electrical contacts; between about 1 and about 9 individual electrical contacts; between about 1 and about 4 individual electrical contacts; between about 4 and about 100 individual electrical contacts; between about 4 and about 50 individual electrical contacts; between about 4 and about 36 individual electrical contacts; between about 4 and about 25 individual electrical contacts; between about 4 and about 16 individual electrical contacts; between about 4 and about 9 individual electrical contacts; etc. The number of individual electrode contacts may be chosen based on the desired electrical performance, area of stimulation, area of tissue contact, and/or range of frequencies to be stimulated, among other parameters.

In some embodiments, the energy delivery elements described herein may include individual electrical contacts that are not identical in geometry. For example, any combination of individual electrical contact geometry shown in FIGS. 48A-48F may be used. Further, for example, any combination of the overall geometry of array shown in FIGS. 59-64 and FIGS. 66A-67C may be used.

In some embodiments, the energy delivery elements described herein may include individual electrical contacts arranged in a geometry that enables spatially selective electrical stimulation, including but not limited to: hexagonal, radially, linear, concentric, saw-tooth, offset arrangements, or a combination thereof.

In some embodiments, the energy delivery elements described herein may include a substrate. The substrate of some embodiments may be flexible. Such flexible substrates may include or be formed of, but not be limited to: polydimethylsiloxane (PDMS), silicone, other elastomer, or similar material known to one of skill in the art. The substrate may be selected to allow the electrode array to conform to the curvature and/or uneven topography of the surface of the tissue, for example cochlear promontory.

In other embodiments, the substrate may be a rigid substrate. Such rigid substrates may include, but not limited to: printed circuit board (e.g., FR-4), complementary metal oxide silicone (CMOS) chip, polycarbonate, acrylic, or a combination thereof.

In some embodiments, one or more energy delivery elements described herein may employ non-fixed electrode contacts, including but not limited to: spring probes, leaf springs, spring coils, or a combination thereof.

A flexible or rigid material of the substrate and/or electrode type may be chosen to accommodate the curvature and/or topography of the tissue surface (e.g., cochlear promontory). In another embodiment, energy delivery elements may be organized in a mesh allowing for the mesh to conform to the curvature and/or topography of the tissue surface where individual electrodes on a mesh array would be connected by a flexible or rigid substrate. In some embodiments, holes or apertures or perforations defined by the mesh would allow for tissue integration and/or overgrowth.

In some embodiments, the electrode arrays described herein may include one or more structural components, including but not limited to: nitinol, titanium, hydrogel, stainless steel, polycarbonate, acrylic, or a combination thereof. Such structural components may be selected based on the desired shape of the array or attachment and/or desired positioning within the middle ear cavity. In some embodiments, the electrode array may be configured in a predefined curvilinear shape. In some embodiments, the electrode array may be pre-shaped such that it assumes a natural conformation that is not flat.

In some embodiments, the energy delivery elements described herein may be mechanically and/or chemically attached to the surface (e.g., of the cochlear promontory) using components and/or techniques, including but not limited to: screws, posts, undercuts, adhesives, conductive adhesives, hydroxyapatite, and/or acid. In some embodiments, additional materials that are used to attach the electrode arrays may be precisely controlled to avoid affecting the normal function of the stapes, stapes footplate, round window, tympanic membrane, and/or Eustachian tube. For example, microfluidic channels, barriers, raised sections, or other structural features may be included in the array to shield structures in the middle ear cavity, prevent the array from impacting those structures, or reduce the arrays impact on those structures.

In some embodiments, pressure may be applied to an energy delivery element against the tissue surface (e.g., cochlear promontory) to couple the array to the surface and/or to enable additional attachment mechanisms to be employed while the pressure is being applied. Such pressure-applying components may include, but are not limited to: a balloon, an expanding hydrogel, an expanding foam, a spring under tension, a deformable material, a mechanical structure (e.g., post, spring, etc.), a cover, or a combination thereof.

In some embodiments, the energy delivery element may be designed such that it can assume a conformation for delivery that is different from an implantation configuration. For example, the electrode array and/or one or more of the pressure-applying components may have a first or delivery configuration (e.g., substantially linear, compressed, etc.) and a second or expanded configuration, for example once in the middle ear cavity. The expanded configuration may be achieved by infusing a fluid into the component (e.g., gas or liquid into a balloon), swelling the component (e.g., swelling a hydrogel), releasing pressure or force on the component, unfurling the component, allowing the component to expand to its biased configuration, etc. The method of providing contact against the tissue may be chosen based on surgical access, available volume within the middle ear cavity, and/or measured impedance values across the electrode-tissue interface.

In some embodiments, the energy delivery element may be surgically implanted into the middle ear through a facial recess, through an external auditory canal, or a combination.

An energy delivery element may be designed such that the conformation for delivery has a cross-sectional area of less than about 200 mm$^2$; less than about 100 mm$^2$; less than about 50 mm$^2$; less than about 20 mm$^2$; less than about 10 mm$^2$; less than about 5 mm$^2$; less than about 2 mm$^2$, between about 2 mm$^2$ and about 10 mm$^2$, between about 2 mm$^2$ and about 200 mm$^2$; etc. Such cross-sectional area may be chosen based on the method of delivery.

In some embodiments, an energy delivery element may be integrated with new and/or existing tissue within the middle ear cavity using techniques including, but not limited to: encouraging epithelial/fibrotic/tissue growth around, over, and/or through the energy delivery element and/or placing the energy delivery element submucosally, where the integration method may be chosen based on desired degree of contact.

In some embodiments, an energy delivery element may be integrated, attached, and/or positioned within the middle ear cavity in a way that is reversible and/or can be removed without causing further hearing loss.

In some embodiments, individual electrical contact(s) may be made of a material or materials, including but not limited to: silver, gold, platinum (Pt), Pt-Iridium (Ir), coated Pt, nickel, brass, copper, metallic alloy, graphite, Titanium Nitride (TiN), Sputtered Iridium Oxide Film (SIROF), or a combination thereof. Such material(s) may be chosen based on desired electrical and/or biocompatibility requirements.

In some embodiments, individual electrical contact(s) may have features that allow the contacts to accommodate variations in tissue (e.g., cochlear promontory) curvature and/or surface topology. Such features may include, but not limited to: spring probe, leaf spring, spring coil, compressible mesh, conductive adhesive, or a combination thereof. The features may be chosen based on the desired level of tissue contact.

In some embodiments, individual electrical contact(s) may be spatially arranged in a particular geometry, including but not limited to: circles, squares, lines, spheres, cones, cylinders, bars, stars, and/or concentric circles. The geometry may be chosen to promote spatially selective electrical stimulation.

In some embodiments, individual electrical contact(s) may have different geometry than other electrical contacts within the array.

In some embodiments, individual electrical contact(s) may have an exposed surface area of less than about 25 mm$^2$; less than about 16 mm$^2$; less than about 9 mm$^2$; less than about 4 mm$^2$; less than about 2 mm$^2$; less than about 1 mm$^2$; less than about 0.5 mm$^2$; less than about 0.2 mm$^2$; less than about 0.1 mm$^2$; less than about 0.05 mm$^2$; less than about 0.01 mm$^2$; between about 200 μm$^2$ and about 2000 μm$^2$; between about 2000 μm$^2$ and about 0.05 mm$^2$; between about 2000 μm$^2$ and about 0.1 mm$^2$; between about 2000 μm$^2$ and about 0.2 mm$^2$; between about 2000 μm$^2$ and about 0.5 mm$^2$; between about 2000 μm$^2$ and about 1 mm$^2$; between about 2000 μm$^2$ and about 2 mm$^2$; between about 2000 μm$^2$ and about 4 mm$^2$; between about 0.01 mm$^2$ and about 1 mm$^2$; between about 0.01 mm$^2$ and about 2 mm$^2$; between about 0.01 mm$^2$ and about 4 mm$^2$; between about 0.01 mm$^2$ and about 9 mm$^2$; between about 0.01 mm$^2$ and about 16 mm$^2$; between about 0.01 mm$^2$ and about 25 mm$^2$; etc. The area may be chosen based on desired electrical properties.

In general, a system for improving hearing in a subject in need thereof may include an electrical stimulator and a receiver. In some embodiments, the electrical stimulator and receiver are one component; in other embodiments, the electrical stimulator and receiver are two or more components. An electrical stimulator may transmit electrical stimuli through every channel of the electrode array; every channel except one ground connection; every channel except two ground connections; or may selectively transmit electrical stimuli through one or more channels of the electrode array based on one or more personalization parameters. The number of stimulation channels may be chosen based on the desired electrical performance, stimulation mode, and/or personalization parameters.

In some embodiments, an electrical stimulator may transmit electrical stimuli through multiple electrodes simultaneously; through one electrode at a time; through all electrodes simultaneously; etc. The number of simultaneously active electrodes may be chosen based on the desired electrical performance, stimulation mode, personalization parameters, degree of high frequency hearing loss, degree of residual low frequency hearing, or a combination thereof.

In some embodiments, an electrical stimulator may utilize different stimulation modes including, but not limited to: monopolar, bipolar, tripolar, partial tripolar, multipolar, and/or common ground modes. Various modes will be further described in connection with FIGS. 16A-16C.

In some embodiments, an electrical stimulator may deliver a variety of stimulation waveforms through each channel including, but not limited to: direct current (DC), alternating current (AC), sine waves, square waves, symmetric biphasic pulses, asymmetric biphasic pulses, monophasic pulses, and/or pulse trains.

In some embodiments, an electrical stimulator may deliver current through multiple channels. In some embodiments, an electrical stimulator may deliver differential current through multiple channels to spatially shape the electrical field and/or steer the electrical current. In some embodiments, an electrical stimulator may deliver differential current through multiple channels to selectively stimulate the tonotopically arranged auditory neurons. In some embodiments, the amount of current delivered through each channel may be personalized based on one or more of: feedback from the subject, anatomy of the subject, a psychoacoustic testing of the subject, the subject's hearing loss profile, brain activity, imaging data, impedance values, or electrically elicited compound action potential data. In some embodiments, the amount of current delivered through each channel may be configured to avoid facial nerve stimulation or stimulation of anatomical structures that might cause pain, discomfort or non-auditory sensation (e.g. Jacobson's nerve, glossopharyngeal nerve, sensory nerves).

In some embodiments, an electrical stimulator may deliver between about 1 nA and about 30 mA of current through each channel; between about 1 nA and about 10 mA; between about 1 nA and about 5 mA; between about 1 nA and about 1 mA; between about 1 nA and about 0.5 mA; between about 1 nA and about 0.1 mA; between about 1 nA and about 10 μA; between about 1 nA and about 1 μA; between about 1 μA and about 30 mA; between about 1 μA and about 10 mA; between about 1 μA and about 5 mA; between about 1 μA and about 1 mA; between about 1 μA and about 0.5 mA; between about 1 μA and about 0.1 mA; between about 1 μA and about 10 μA; between about 10 μA and about 30 mA; between about 10 μA and about 10 mA; between about 10 μA and about 5 mA; between about 10 μA and about 1 mA; between about 10 μA and about 0.5 mA; between about 10 μA and about 0.1 mA; etc. The range of current may be chosen based on the desired electrical performance, stimulation mode, location of the implantable components, and/or safety of the nearby tissue.

In some embodiments, an electrical stimulator may deliver a maximum current density of about 200 mA/cm$^2$; about 100 mA/cm$^2$; about 50 mA/cm$^2$; about 10 mA/cm$^2$; about 1 mA/cm$^2$; about 100 μA/cm$^2$; about 50 μA/cm$^2$; about 10 μA/cm$^2$; etc. through each channel. The maximum current density may be chosen based on the desired electrical performance, stimulation mode, location of the implantable components, degree of high frequency hearing loss, degree of residual low frequency hearing, and/or safety of the nearby tissue.

In some embodiments, an electrical stimulator may deliver a maximum charge density of about 1 mC/cm$^2$; about 400 μC/cm$^2$; about 200 μC/cm$^2$; about 10 μC/cm$^2$; about 50 μC/cm$^2$; about 20 μC/cm$^2$; about 10 μC/cm$^2$; about 5 μC/cm$^2$; about 1 μC/cm$^2$; about 500 nC/cm$^2$; about 100 nC/cm$^2$; etc. through each channel. The maximum charge density may be chosen based on the desired electrical performance, stimulation mode, location of the implantable components, degree of high frequency hearing loss, degree of residual low frequency hearing, and/or safety of the nearby tissue.

In some embodiments, an electrical stimulator may deliver electrical stimuli in a frequency range between about 10 Hz and about 30 kHz; between about 10 Hz and about 10 kHz; between about 10 Hz and about 5 kHz; between about 10 Hz and about 2 kHz; between about 10 Hz and about 1 kHz; between about 50 Hz and about 30 kHz; between about 50 Hz and about 10 kHz; between about 50 Hz and about 5 kHz; between about 50 Hz and about 2 kHz; between about 50 Hz and about 1 kHz; between about 100 Hz and about 30 kHz; between about 100 Hz and about 10 kHz; between about 100 Hz and about 5 kHz; between about 100 Hz and about 2 kHz; between about 100 Hz and about 1 kHz; etc. The frequency range may be chosen based on the desired electrical performance, stimulation mode, degree of high frequency hearing loss, degree of residual low frequency hearing, and/or one or more personalization parameters.

In general, a system for improving hearing in a subject in need thereof may include a receiver and transmitter. One or both of the receiver and transmitter may be implanted under the skin or in the middle ear cavity. One or both of the receiver and transmitter may be made from a magnetic induction coil or an induction coil. The receiver and transmitter may be communicatively coupled via a wired connection or wirelessly. During wireless communication, the transmitter may communicate to the receiver via radio frequency, for example Bluetooth, Wi-Fi, or similar technology. The transmitter may relay power and electrical stimuli to the receiver (i.e., relayed between the external hardware and the implantable components) or may relay just electrical stimuli to the receiver (i.e., relayed between the external hardware and the implantable components).

In general, a system for improving hearing of a subject in need thereof may include external hardware. The external hardware may capture auditory information (e.g., via a microphone) and convert to electrical stimuli (e.g., via a speech processor). The external hardware may transmit electrical stimuli to the implantable components (e.g., via a transmitter). The external hardware may provide power to the implantable components (e.g., via a power source). For example, the external hardware may include an electrical stimulator, receiver, transmitter, speech processor, power source, microphone, or any combination of the components. The external hardware may include additional components depending on the method of electrical stimulation. Alternatively, one or more of the components may be internally positioned and/or implanted, for example in the middle ear cavity. For example, a receiver and/or electrical stimulator may be positioned internally and/or implanted in the middle ear cavity.

In some embodiments, the external hardware may be assembled as a unitary body. In some embodiments, the hardware may be pre-assembled or assembled in-situ, for example, with an interconnect system whereby the hardware may be modular, connecting through a series of leads and connectors that may be assembled during the course of the implantation process.

One or more external hardware components may communicate wirelessly or via a wired connection with one or more other external components. One or more external hardware components may communicate wirelessly or via a wired connection with one or more implantable hardware components.

Any of the components described herein may be biocompatible and/or intended for long-term use, for example thirty days to months to years.

Any of the components described herein may be worn comfortably on the skin of the user including, but not limited to: the scalp, behind the ear, in-ear, eyes (spectacles), and/or wrist.

Any of the components described herein may be non-body worn with form factors including, but not limited to: handheld and/or carrying case.

Any of the components described herein may communicate with a range of devices via radio frequency or another wireless communication protocol. These devices may include: an extracochlear or intracochlear implant system implanted in the same ear or the opposite ear; an acoustic amplification device being used in the same or opposite ear; one or more peripheral electronics (e.g., mobile device, televisions, external microphones, wearable device, etc.); and/or broadband communication infrastructure (e.g., Wi-Fi, 3G, 4G, 5G, Bluetooth, etc.).

Any of the components described herein may have a weight less than about 200 g; less than about 100 g; less than about 80 g; less than about 60 g; less than about 40 g; less than about 20 g; less than about 10 g; between about 10 g and about 200 g; etc. Such weight may be chosen to improve the form factor for usability.

Any of the components described herein may have a shape, arrangement, or placement that is designed to promote discreetness of the system.

In general, a system for improving hearing of a subject in need thereof may include a speech processor. The speech processor may be configured to convert audio data from the microphone to electrical signals that can be transmitted to the implantable components. In some embodiments, the speech processor may utilize different stimulation modes including, but not limited to: monopolar, bipolar, tripolar, partial tripolar, multipolar, and/or common ground modes, as will be described in further detail in connection with FIGS. 16A-16C. In some embodiments, the speech processor may be programmable in order to tailor the performance to the patient. In some embodiments, the speech processor may be reprogrammed to improve the performance for the patient. In some embodiments, the speech processing algorithm may be personalized based on one or more of: feedback from the subject, anatomy of the subject, a psychoacoustic testing of the subject, a subject's hearing loss profile, brain activity, imaging data, impedance values, electrically elicited compound action potential data, or a combination thereof. In some embodiments, the speech processor may be replaced with updated components over time without requiring re-implantation of the implantable components.

In general, a system for improving hearing of a subject in need thereof may include a power source. In some embodiments, the power source may supply power to both the external and internal hardware. In some embodiments, the power source may supply power to only the external hardware. In some embodiments, the power source may supply power wirelessly via the transmitter to the internal hardware including the receiver. In some embodiments, the power source may comprise one or more single-use batteries. In some embodiments, the power source may comprise one or more rechargeable batteries. In some embodiments, the power source may last for about 48 hours with constant use without running out of charge; may last about 24 hours; may last about 18 hours; may last about 12 hours; may last about 6 hours; may last about 3 hours; between about one hour and about 50 hours; etc. The power requirements may be chosen based on the requirements of the patient and/or selected components and their location and functionality.

In general, a system for improving hearing of a subject in need thereof may include a microphone. In some embodiments, the microphone may be able to detect frequencies between about 20 Hz and about 20 kHz; between about 20 Hz and about 10 kHz; between about 20 Hz and about 8 kHz; between about 20 Hz and about 6 kHz; between about 200 Hz and about 20 kHz; between about 200 Hz and about 10 kHz; between about 200 Hz and about 8 kHz; between about 20 Hz and about 6 kHz; between about 500 Hz and about 20 kHz; between about 500 Hz and about 10 kHz; between about 500 Hz and about 8 kHz; between about 500 Hz and about 6 kHz; between about 1 kHz and about 20 kHz; between about 1 kHz and about 10 kHz; between about 1 kHz and about 8 kHz; between about 1 kHz and about 6 kHz; etc. The frequency range of the microphone may be chosen based on the desired range of hearing improvement or restoration. In some embodiments, a system for improving hearing may comprise more than one microphone or multiple microphones.

In another example of the system, the external components may be integrated with the implantable components and the entire system may be implanted.

In general, a method of improving hearing in a subject in need thereof may include attaching an energy delivery element to the tissue, for example a cochlear promontory. Attaching an energy delivery element to the cochlear promontory may be performed without penetrating the cochlea. Once attached, the method may include delivering electrical stimulation through bone to the neurons of the cochlea. Further once attached, the method may include delivering electrical stimulation through bone to the neurons of the basal turn of the cochlea.

In some embodiments, a method may generally include personalizing the pattern of electrical stimulation across the electrode array based on one or more of: feedback from the subject, an anatomy of the subject, a psychoacoustic testing of the subject, a subject's hearing loss profile, brain activity, imaging data, impedance values, electrically elicited compound action potential data, or a combination thereof.

In general, a method of improving hearing in a subject in need thereof may include positioning an energy delivery element against the tissue, for example a promontory of the cochlea, without penetrating the cochlea. Not penetrating the cochlea or minimally processing the cochlea, in various embodiments, may preserve or not substantially impact residual hearing.

Figure 1:
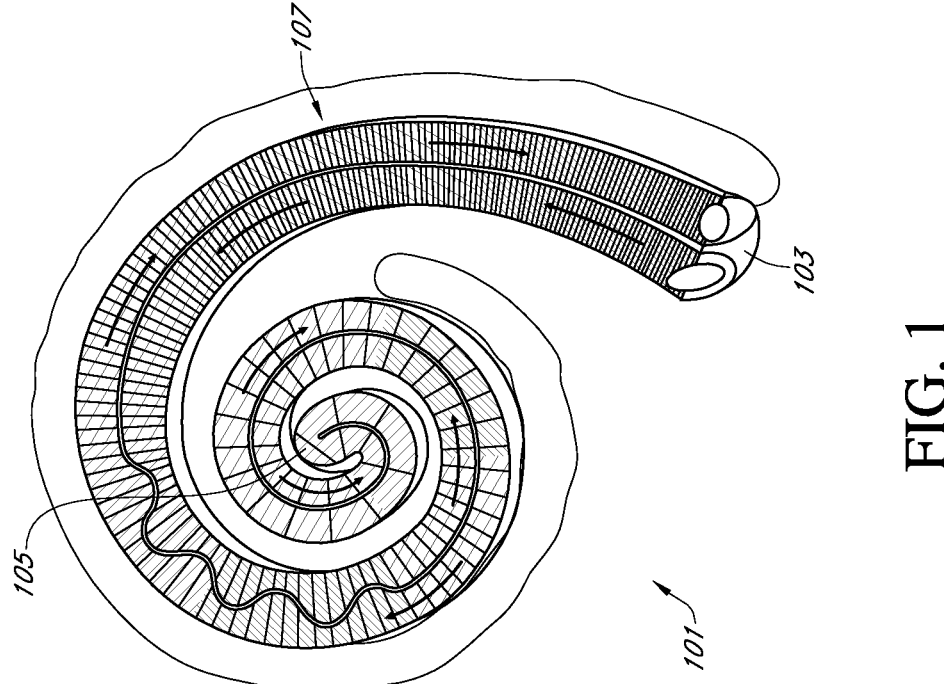
FIG. 1 shows the tonotopic arrangement of a cochlea.

FIG. 1 depicts a cross-sectional view of a human cochlea 101 with its tonotopic regions of frequency reception labeled. The highest frequencies (about 20 kHz) are generally registered by neurons positioned at the base 103 of the cochlea near the oval and round windows. Progressing down the length of spiral towards the apex 105, the neurons of the cochlea 101 instead become increasing attuned to lower frequencies, down to about 200 Hz. In many embodiments, the implant as described herein is adapted to target "higher" frequencies, and therefore the corresponding tonotopic regions 107 of the cochlea. In some embodiments, the energy delivery elements described herein target the tonotopic region of about 1 kHz or higher (i.e., about 1 kHz to about 20 kHz). In other embodiments, the energy delivery elements described herein target the tonotopic region of about 1.5 kHz to about 20 kHz, about 2 kHz to about 20 kHz, about 4 kHz to about 20 kHz, about 1 kHz to about 8 kHz, about 1.5 kHz to about 8 kHz, about 2 kHz to about 8 kHz, about 1 kHz to about 6 kHz, about 1.5 kHz to about 6 kHz, or about 2 kHz to about 6 kHz.

FIG. 2 depicts a block diagram of a device 200 for extracochlear stimulation. In many embodiments, the device 200 comprises an external component 210 and an internal implanted component 240. The external component 210 can comprise, in various embodiments, an external casing with or without controls 212, a directional microphone 214, a first external component processing module 216, a power source 218 (e.g., a rechargeable high-density battery), a power amplifier 220, and an external wireless power and data transmitter/receiver 224. In some embodiments, the external component 210 can additionally comprise an electric acoustic stimulation (EAS) module 226 for simultaneous acoustic amplification for residual hearing. The internal implanted component 240 can comprise, in various embodiments, a stimulator casing 242, one or more multiplexing control units 244 and 246, at least one extracochlear stimulating energy delivery element 248 (e.g., electrode), a stimulation pulse generator 250, a second internal component processing module 252, a return energy delivery element 254 (e.g., electrode), and an internal wireless power and data transmitter/receiver 256. In many embodiments, the external wireless power and data transmitter/receiver 224 is in wireless communication with the internal wireless power and data transmitter/receiver 256 such that external transmitter/receiver 224 can send electronic power and signals to the internal transmitter/receiver 256 and that the internal transmitter/receiver 256 can return various signals to the external transmitter/receiver 224.

In various embodiments, the external casing 212 provides structural rigidity and support to the external component 210, housing and organizing at least a portion of its other components. In some embodiments, the external casing 212 also comprises various controls. These controls can be analog or digital buttons, switches, or dials across various embodiments that can communicate one or more changes in parameters (e.g., perceived volume, etc.) to the device 200. In other embodiments, the device 200 can be in electronic communication with an alternate or additional set of controls on a separate control device (e.g., a handheld remote) or a user computing device (e.g., a mobile computing device, wearable, etc.). The directional microphone 214 detects auditory impulses (i.e., sounds) from the environment, generates a corresponding electrical signal (i.e., a first auditory electrical signal), and sends the first auditory electrical signal to the external component processing module 216 in many embodiments. In some embodiments, the directional microphone 214 can be positioned within the external casing 212 such that, when considering the positioning of the external component 210 as a whole on a user's head, the directional microphone 214 preferably detects sounds from a given orientation relative to the user (e.g., from the front and/or same said of the head of the device's 200 positioning) and avoids detecting other sounds (e.g., sounds internal to the user's body).

In many embodiments, the directional microphone may be able to detect frequencies between 20 Hz and 20 kHz; between 20 Hz and 10 kHz; between 20 Hz and 8 kHz; between 20 Hz and 6 kHz; between 200 Hz and 20 kHz; between 200 Hz and 10 kHz; between 200 Hz and 8 kHz; between 20 Hz and 6 kHz; between 500 Hz and 20 kHz; between 500 Hz and 10 kHz; between 500 Hz and 8 kHz; between 500 Hz and 6 kHz; between 1 kHz and 20 kHz; between 1 kHz and 10 kHz; between 1 kHz and 8 kHz; between 1 kHz and 6 kHz; where the frequency range of the microphone may be chosen based on the desired range of hearing improvement or restoration, a degree of high frequency hearing loss of the patient, a degree of residual low frequency hearing of the patient, or a combination thereof.

The first external component processing module 216 comprises at least one processor and at least one memory storing machine-readable instructions that are executable by the processor to perform a variety of methods across numerous embodiments. The at least one processor and at least one memory can be considered a programmable microcontroller in some embodiments. In various embodiments, the first processing module 216 can receive an auditory electrical signal from the directional microphone 214 whereupon the first processing module 216 can execute machine-readable instructions for a speech coding algorithm stored on the at least one memory. The first processing module 216 can use the speech coding algorithm to operate on the first auditory electrical signal in a variety of ways. For example, the instructions can include for detecting patterns in the first auditory electrical signal indicative of speech and generating from at least one of the detected patterns an extracochlear stimulation signal. Exemplary patterns include, but are not limited to: pitch patterns of a predetermined range of frequency and/or duration indicative of speech in one or more languages; pitch patterns indicative of phonemes common to one or more languages; a rate of occurrence of the afore-mentioned pitch patterns indicative of multiple words of one or more languages; etc. The extracochlear stimulation signal can be adapted to take any form, analog or digital, capable of instructing an internal implanted component 240 of the device 200 to electrically stimulate the neurons of a prede-termined frequency range of the cochlea of a user from an external surface of the cochlea. Across many embodiments, the extracochlear stimulation signal can instruct the internal implanted component 240 to stimulate the cochlea in a variety of modes, including but not limited to: monopolar, bipolar, tripolar, partial tripolar, multipolar, and/or common ground modes. In some embodiments, especially those wherein at least one of the first auditory electronic signal and extracochlear stimulation signal is a digital signal, the gen-eration of the extracochlear stimulation signal can be con-sidered to be performed by a digital signal processor of the first processing module 216.

In some embodiments, the first processing module 216 can further comprise a Bluetooth connectivity module that allows for the communication of the first processing module 216 to other elements of the device 200 and/or to additional user devices (not shown) via the Bluetooth communication protocol. For example, the Bluetooth connectivity module can, in some embodiments, enable communication between the first processing module 216 and the directional micro-phone 214, various controls located on an additional user device (e.g., a smartphone, tablet, remote, wearable, etc.), to various elements of the internal implanted component 240 of the same ear, and/or to various elements of an external or internal implanted component in the other ear of a user. In other embodiments, an alternative wireless communication protocol can be employed (e.g., Wi-Fi, cellular 3G, 4G, 5G, Zigbee, etc.). In these embodiments, the Bluetooth connec-tivity module can be replaced by an appropriate module allowing for the alternate wireless communication protocol.

Furthermore, in some embodiments, various elements of the first processing module 216, including, but not limited to, its speech coding algorithm, can be updated or repro-grammed to modify its performance. It can be updated in order to tailor or improve its performance for a user in certain embodiments, and in many embodiments, the updated programming can be provided via the Bluetooth or alternate network made accessible by the Bluetooth connec-tivity module.

In many embodiments, the external component comprises a power source 218 such as a rechargeable high-density battery which can provide the user the dual convenience of lower operating costs, as the battery can be recharged, as well as an infrequent need to recharge the battery, as it is high-density. One of skill in the art will appreciate the various types of batteries available as the power source 218 including, but not limited to: lithium ion, lithium iron phosphate, and lithium-polymer batteries. In alternative embodiments, other battery types can be employed without deviating from the scope of this disclosure. In some embodi-ments, the power supply may last for about 48 hours with constant use without running out of charge; in certain examples, may last about 24 hours; in certain examples, may last about 18 hours; in certain examples, may last about 12 hours; in certain examples, may last about 6 hours; in certain examples, may last about 3 hours; or between about one hour and about 50 hours; or between about one hour and about 100 hours; where the power requirements may be chosen based on the requirements of the user.

The external component 210 can comprise a power ampli-fier 220 in many embodiments. The power amplifier 220 serves to boost the amplitude (e.g., voltage or current) of a received electrical signal for transmitting it elsewhere (e.g., to the internal implanted component 240 via the external wireless power and data transmitter/receiver 224). In various embodiments, the signals boosted by the power amplifier 220 can be one or more of an extracochlear stimulation signal received from the first processing module 216 and/or a second auditory electrical signal from an optional electric acoustic stimulation (EAS) module 226 for simultaneous acoustic amplification for residual hearing, as described in further detail elsewhere herein. Optionally, external compo-nent 210 may be further electrically connected with a bone conduction hearing device.

In some embodiments, the device 200 can optionally comprise an electric acoustic stimulation (EAS) module 226. Either using the directional microphone 214 or provid-ing a separate microphone of its own (not shown), the EAS module 226 detects sounds from the environment and gen-erates a second auditory electrical signal which can be amplified by the power amplifier 220, as described above. A speaker (not shown) positioned near or in the outer ear of a user can then play the optionally boosted second auditory electrical signal aloud, allowing for any remaining or residual natural hearing ability to detect the sound more easily. In some embodiments, the EAS module 226 is adapted to detect sounds of about 1 kHz or less, alternatively of about 1.5 kHz or less, and alternatively of about 2 kHz or less in frequency.

In many embodiments, the device 200 can comprise an external wireless power and data transmitter/receiver 224. This transmitter/receiver 224 may be configured to transmit a variety of signals, including those received from the power amplifier 220 and/or external component processing module 216, including, but not limited to, extracochlear stimulation signals, and wirelessly communicating them to an internal wireless power and data transmitter/receiver 256. A variety of wireless communication protocols can be employed for the communication of data signals (e.g., Wi-Fi, Bluetooth, cellular 3G, 4G, 5G, Zigbee, etc.) In further embodiments, the external wireless power and data transmitter/receiver 224 is also capable of transmitting electronic power wire-lessly to the internal wireless power and data transmitter/receiver 256. In these embodiments, this element allows the internal implanted component 240 to be electronically pow-ered without the need for a separate power supply (which would be medically inconvenient for an implanted device in some embodiments) or a wired connection to the external component 210 which can increase installation operation time, cost, and invasiveness, in certain embodiments. In some embodiments, one or both of the external and internal wireless power and data transmitter/receiver 224 and 256 can be an induction coil, such as a magnetic induction coil. In alternative embodiments, the external and internal wire-less power and data transmitter/receiver 224 and 256 can be replaced by a wired connection.

As described above, the internal implanted component 240 comprises an internal wireless power and data trans-mitter/receiver 256 that can receive electronic power and various electronic signals from the external wireless power and data transmitter/receiver 256. The internal transmitter/receiver 256, in many embodiments, is adapted to adequately transmit received power throughout at least a portion of the internal implanted component 240 in order to operably power it. When the internal transmitter/receiver 256 receives an extracochlear stimulation signal, it can send it to the internal component processing module 252 for further processing. In embodiments wherein the external and internal wireless power and data transmitter/receiver 224 and 256 can be replaced by a wired connection, the wired connection can directly connect one or both of: the power amplifier 220 or first processing module 216 to the second internal component processing module 252.

The second internal component processing module 252 can comprise at least one processor in communication with at least one memory storing machine-readable instructions executable by the processor that allow the processor to perform various tasks. In some embodiments, the second processing module 252 can be considered to comprise a control unit, a read-write memory, and record capabilities. In many embodiments, the machine-readable instructions stored on the memory instruct the processor to receive an extracochlear stimulation signal from the internal wireless power and data transmitter/receiver 256 and accordingly activate a stimulation pulse generator 250 to provide current to at least one extracochlear stimulating energy delivery element 248 in the mode determined by the extracochlear stimulation signal. The second processing module 252 is responsible for the control of the at least one return energy delivery element 254 that can be switched on or off. The purpose of the return electrode 254 in many embodiments, is to limit lateral current spread from the at least one extracochlear stimulating energy delivery element 248 to allow for more targeted neural stimulation and tonotopic selectivity.

In many embodiments, the second processing module 252 can also store data in its memory. For example, it can store data regarding all or a subset of extracochlear stimulation signals it has received. In other embodiments, the second processing module 252 can also store whether it successfully executed a given extracochlear stimulation signal with or without further data identifying various error conditions. Additional or alternative types of data can be stored in the record capabilities in alternative embodiments. Data stored in the record capabilities of the second processing module 252 can be communicated to the first processing module 216 via the internal wireless power and data transmitter/receiver 256.

Upon receiving an appropriate signal from the second processing module 252, a stimulation pulse generator 250 produces an electric charge according to the signal and transmits it to at least one extracochlear stimulating energy delivery element 248 via one or more multiplexing control units 244 and 246. The one or more multiplexing control units 244 and 246 are adapted to appropriately distribute the charge produced by the stimulation pulse generator 250 to the at least one extracochlear stimulating energy delivery element 248. In embodiments featuring more than one extracochlear stimulating energy delivery element 248, the one or more multiplexing control units 244 and 246 can distribute the charge to two or more extracochlear stimulating energy delivery elements 248 in order to provide various modes of stimulation to the cochlear including, but not limited to: monopolar, bipolar, tripolar, partial tripolar, multipolar, and/or common ground modes.

In various embodiments, the at least one extracochlear stimulation energy delivery element 248 can comprise silver, gold, platinum (Pt), Pt-Iridium (Ir), coated Pt, nickel, brass, copper, metallic alloy, graphite, and/or SIROF. In various embodiments, the at least one extracochlear stimulating energy delivery element 248 can have a variety of geometries, including but not limited to: circles, squares, lines, spheres, cones, cylinders, bars, stars, and/or concentric circles, where the geometry may be chosen to promote spatially selective electrical stimulation. In some embodiments, each extracochlear stimulating energy delivery element 248 can have different geometry than other electrical contacts within the array. In further embodiments, each extracochlear stimulating energy delivery element 248 can have an exposed surface area less than about 25 mm$^2$; less than about 16 mm$^2$; less than about 9 mm$^2$; less than about 4 mm$^2$; less than about 2 mm$^2$; less than about 1 mm$^2$; less than about 0.5 mm$^2$; less than about 0.2 mm$^2$; less than about 0.1 mm$^2$; less than about 0.05 mm$^2$; less than about 0.01 mm$^2$; between about 200 μm$^2$ and about 2000 μm$^2$; between about 2000 μm$^2$ and about 0.05 μm$^2$; between about 2000 μm$^2$ and about 0.1 μm$^2$; between about 2000 μm$^2$ and about 0.2 μm$^2$; between about 2000 μm$^2$ and about 0.5 μm$^2$; between about 2000 μm$^2$ and about 1 mm$^2$; between about 2000 μm$^2$ and about 2 mm$^2$; between about 2000 μm$^2$ and about 4 mm$^2$; between about 0.01 mm$^2$ and about 1 mm$^2$; between about 0.01 mm$^2$ and about 2 mm$^2$; between about 0.01 mm$^2$ and about 4 mm$^2$; between about 0.01 mm$^2$ and about 9 mm$^2$; between about 0.01 mm$^2$ and about 16 mm$^2$; between about 0.01 mm$^2$ and about 25 mm$^2$; where the area may be chosen based on desired electrical properties.

The internal implanted component 240, in many embodiments, comprises a stimulator casing 242 that is configured to hold, retain, etc. at least in part, one or more implanted components of the system (e.g., control unit, pulse generator, etc.). For example, the stimulator casing 242 comprising one or more components therein may be positioned behind the ear. In many embodiments, the stimulator casing 242 can be made of an elastomeric material such as, but not limited to: polydimethylsiloxane (PDMS) or silicone. By having some flexibility due to its elastomeric composition, in some embodiments, the stimulator casing 242 can contort, bend, or flex to conform to the curvature or uneven topography of the surface on which it is positioned (e.g., temporal bone surface or cavity created in temporal bone).

Figure 3:
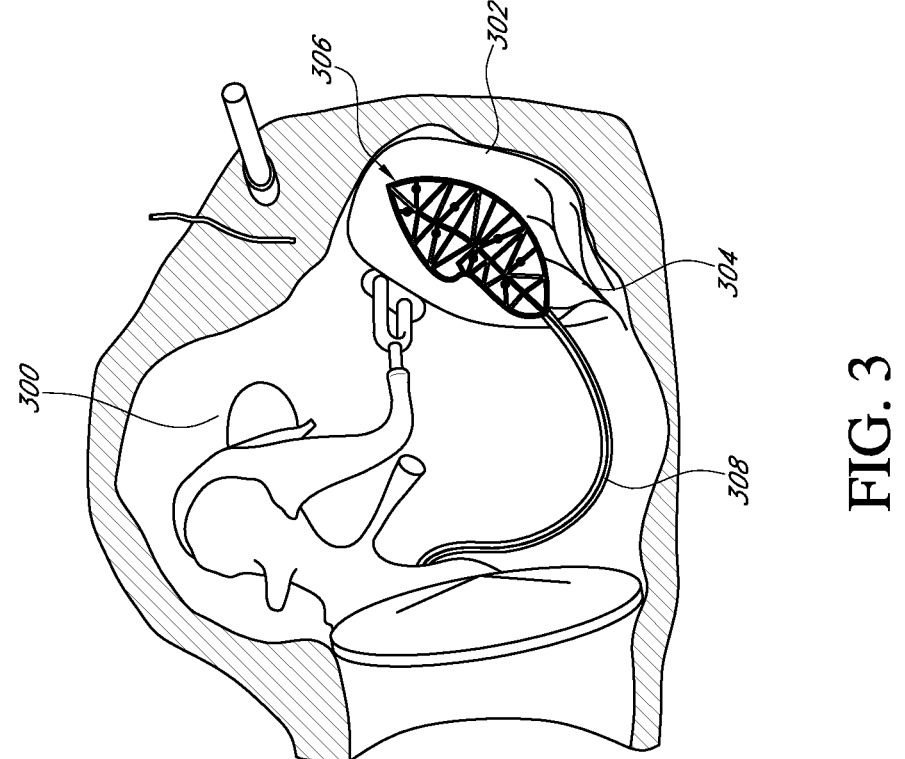
FIG. 3 shows one embodiment of a device comprising a multi-channel electrode array coupled to the cochlear promontory.
Figure 79:
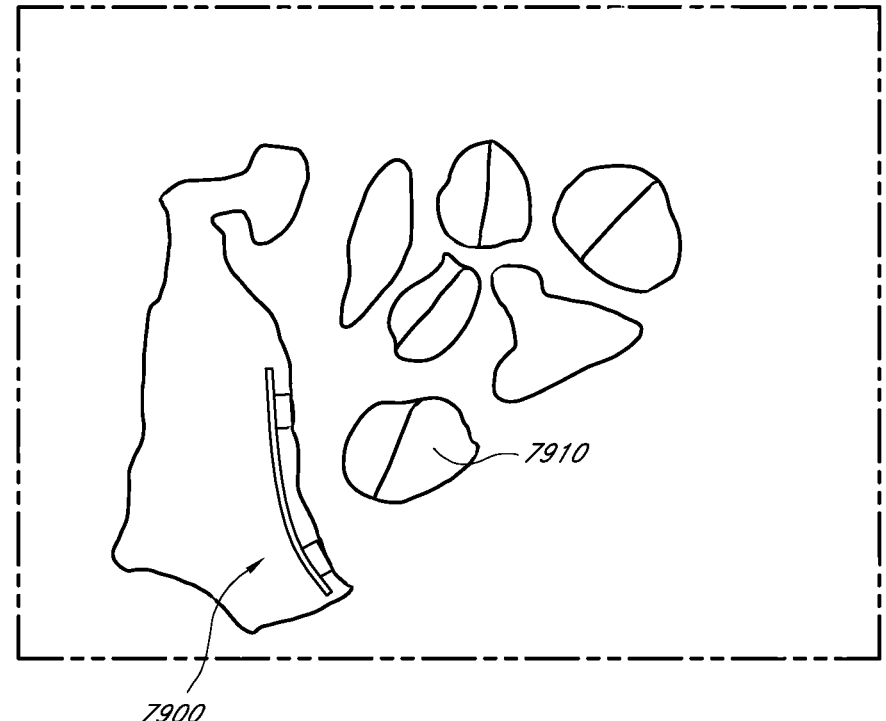
FIG. 79 shows an image of an energy delivery element conforming to a promontory of a cochlea that overlies the basal turn of a cochlea.

FIG. 3 shows an anatomical cross-sectional view of a middle ear cavity 300 having an embodiment of a subset of an implanted portion 302 of a device for extracochlear stimulation attached on the promontory 304 of the middle ear 300. The promontory 304, in the human ear, overlies the basal turn of the cochlea, the portion of the cochlea responsible for high-frequency hearing. In this embodiment, the implanted portion 302 comprises an energy delivery element 306, for example comprising electrodes, that allows for various modes of stimulation. A lead 308 connects the energy delivery element 306 to other components (not shown) of the implanted portion 302. FIG. 79 shows an anatomical cross-sectional view of a cochlear promontory with an energy delivery element 7900 conformed to the surface of the promontory which is overlying the basal turn of the cochlea 7910. The energy delivery element may be positioned such that electrical contacts are positioned both inferiorly and superiorly to the basal turn as shown in the figure. The energy delivery element may also be positioned such that electrical contacts are positioned both anteriorly and posteriorly to the basal turn. This positioning may be optimized for current steering or shaping the electric field to selectively stimulate auditory neurons within the basal turn.

Figure 4:
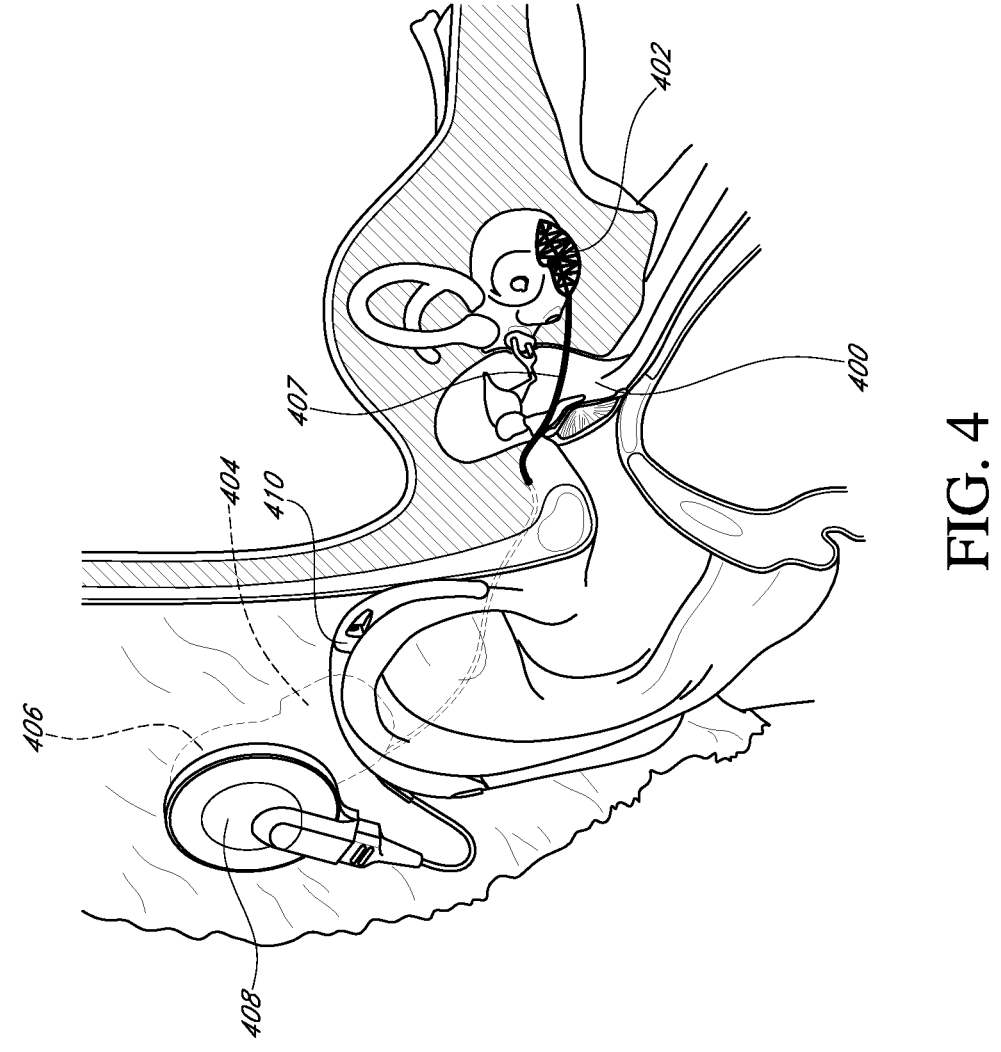
FIG. 4 shows another embodiment of an energy delivery element positioned against the cochlear promontory and connected to an implanted stimulator.

FIG. 4 shows another embodiment of an energy delivery element 402 positioned against the cochlear promontory in the middle ear cavity 400. In this embodiment, the implanted energy delivery element 402 is connected to an implanted stimulator 404 with an induction coil 406 (i.e., an embodiment of an internal wireless data and power transmitter/receiver) via a lead 407. This implanted stimulator 404 can itself be connected wirelessly and/or transcutaneously with external hardware 408 comprising a directional microphone 410. The external hardware 408, using the directional microphone 410, can collect external sound and generate a corresponding extracochlear stimulation signal that is transmitted to the implanted stimulator 404, which in turn, produces an electrical stimulation that is delivered to an extracochlear surface via the implanted extracochlear energy delivery element 402 to improve or restore hearing. In the embodiment of FIG. 4, the external hardware 408 can also provide wireless electric power to the implanted stimulator and extracochlear energy delivery element.

Figure 5:
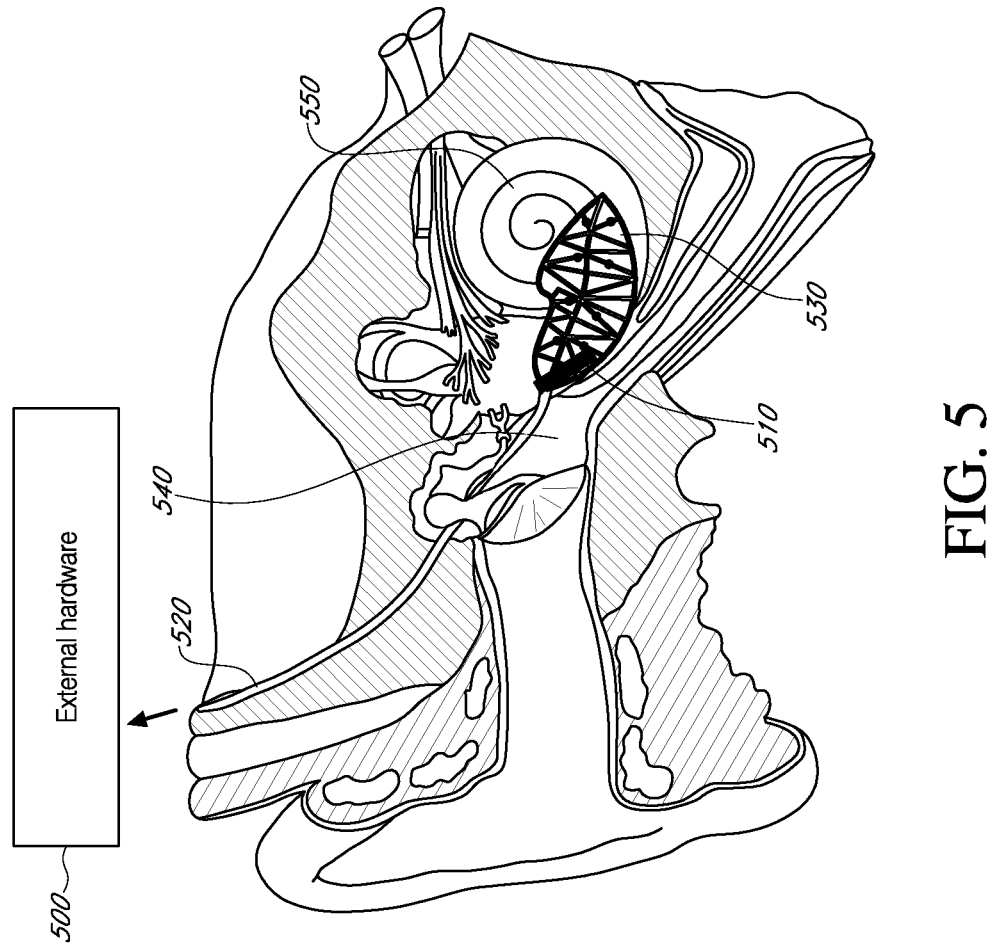
FIG. 5 shows a method of delivering an energy delivery element through a mastoid approach, such that the array is attached to a stimulator via a cable routed through the facial recess.

FIG. 5 shows a facial recess (posterior tympanotomy) method of implant delivery. Any of the components, for example electrode arrays, described herein may be delivered through the facial recess. The method includes creating an incision proximal to the postauricular crease to expose the mastoid cortex of the temporal bone. A canal is drilled through the facial recess of the temporal bone to access the middle ear cavity and thus the cochlea. At least a subset of the internal components, for example the electrode array 530 can then be situated in the middle ear cavity 540. The receiver and stimulator (not shown) of the implanted components can be implanted elsewhere in the patient's body, such as the position depicted in FIG. 4. The energy delivery element 530 can be electrically coupled via lead 520 through a local control unit 510 (similar to control unit 244 of FIG. 2) to the receiver and stimulator, which is in turn in electronic communication with external hardware 500 (e.g., microphone, speech processor, transmitter, etc.). Alternatively, as one of skill in the art will appreciate, any of the embodiments described herein may include a local control unit (e.g., in the middle ear cavity, proximal to the electrode array but separate from the receiver) or an external control unit (e.g., implanted behind the ear, positioned externally behind the ear, receiver located with the control unit externally, etc.). In some embodiments, the receiver and stimulator can be in wireless electronic communication with the external hardware 500. Energy delivery element 530 is attached or coupled to an external surface of the cochlea 550, using any of attachment methods described elsewhere herein. Alternatively, in other embodiments, the control unit 510 comprises the receiver/stimulator.

Figure 75:
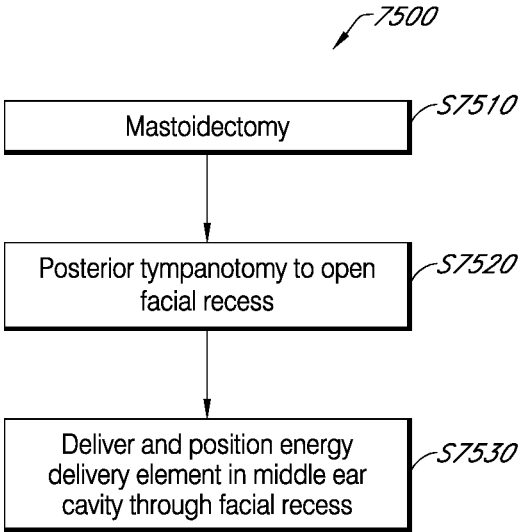
FIG. 75 shows one embodiment of a method of delivering an energy delivery element through a facial recess approach.

One method 7500, as shown in FIG. 75, of delivering an energy delivery element through a facial recess includes: performing a mastoidectomy at block S7510; performing a posterior tympanotomy to open facial recess at block S7520; and delivering and positioning an energy delivery element in a middle ear cavity through the facial recess at block S7530. As appreciated by one of skill in the art, any of the method steps may be performed in any order or combined.

Figure 76:
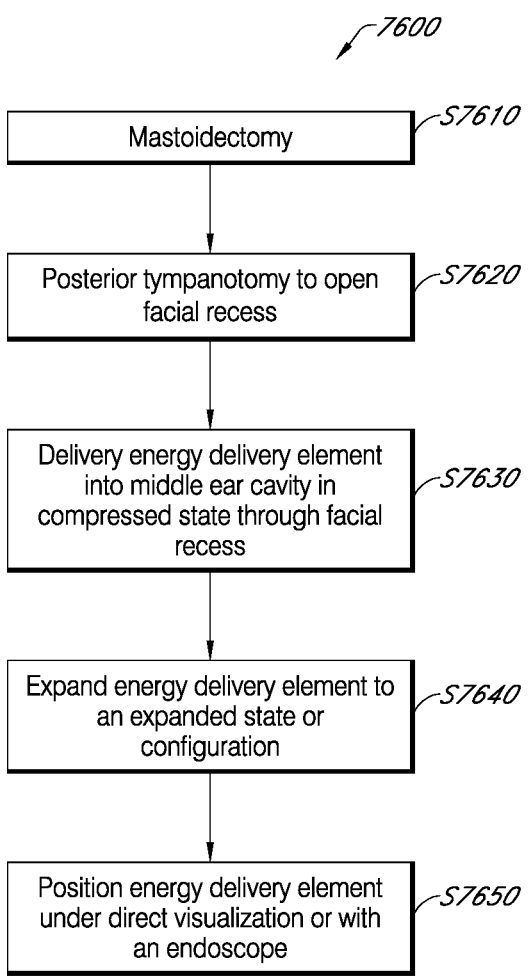
FIG. 76 shows another embodiment of a method of delivering an energy delivery element through a facial recess approach.

Another method 7600, as shown in FIG. 76, of delivering an energy delivery element through a facial recess includes: performing a mastoidectomy at block S7610; performing a posterior tympanotomy to open facial recess at block S7620; delivering an energy delivery element into the middle ear cavity in a compressed state through the facial recess at block S7630; expanding the energy delivery element to an expanded state or configuration at block S7640; and positioning an energy delivery element under direct visualization or with an endoscope at block S7650. As appreciated by one of skill in the art, any of the method steps may be performed in any order or combined.

In some embodiments, performing a mastoidectomy comprises a surgical procedure of the temporal bone that opens postauricular air cells by removing the thin bony partitions between them. Each mastoidectomy may be unique because of the variable pneumatization patterns of the temporal bone.

In some embodiments, performing a posterior tympanotomy comprises opening a window from the mastoid to the middle ear between the facial nerve and chorda tympani to access the middle ear cavity.

Figure 50:
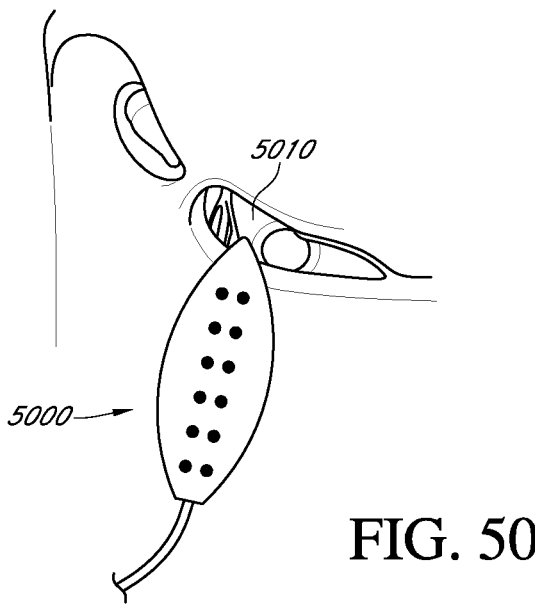
FIG. 50 shows a typical facial recess approach with an energy delivery element in an expanded configuration.
Figure 51:
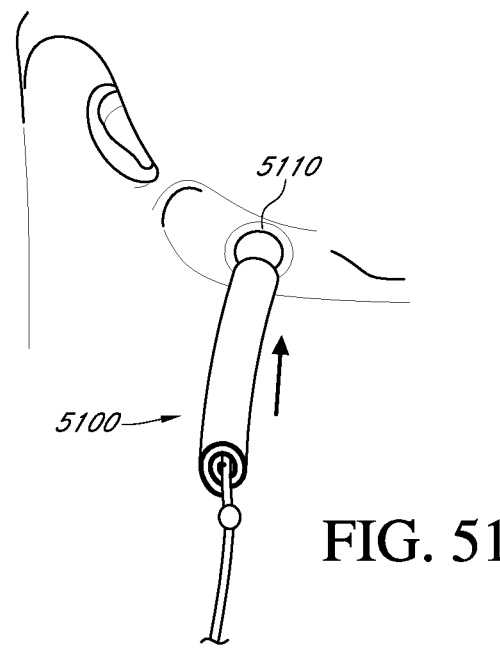
FIG. 51 shows a minimally invasive facial recess approach with an energy delivery element in a compressed configuration.

In some embodiments, facial recess access may be achieved using a minimally invasive approach. FIG. 50 shows a typical facial recess approach with an energy delivery element 5000 in an expanded configuration. As shown in FIG. 50, a typical facial recess opening size ranges from about 3 mm to about 5 mm in width. However, as shown in FIG. 51, using a minimally invasive facial recess approach enables delivery of an energy delivery element 5100 in a compressed configuration, as described elsewhere herein, and the facial recess opening size to range from about 0.5 mm to about 3 mm, up to a 90% reduction in opening size. The reduced facial recess opening size reduces the risk of facial or chorda tympani nerve injury and reduces the surgical time needed to expose the facial recess.

Figure 6:
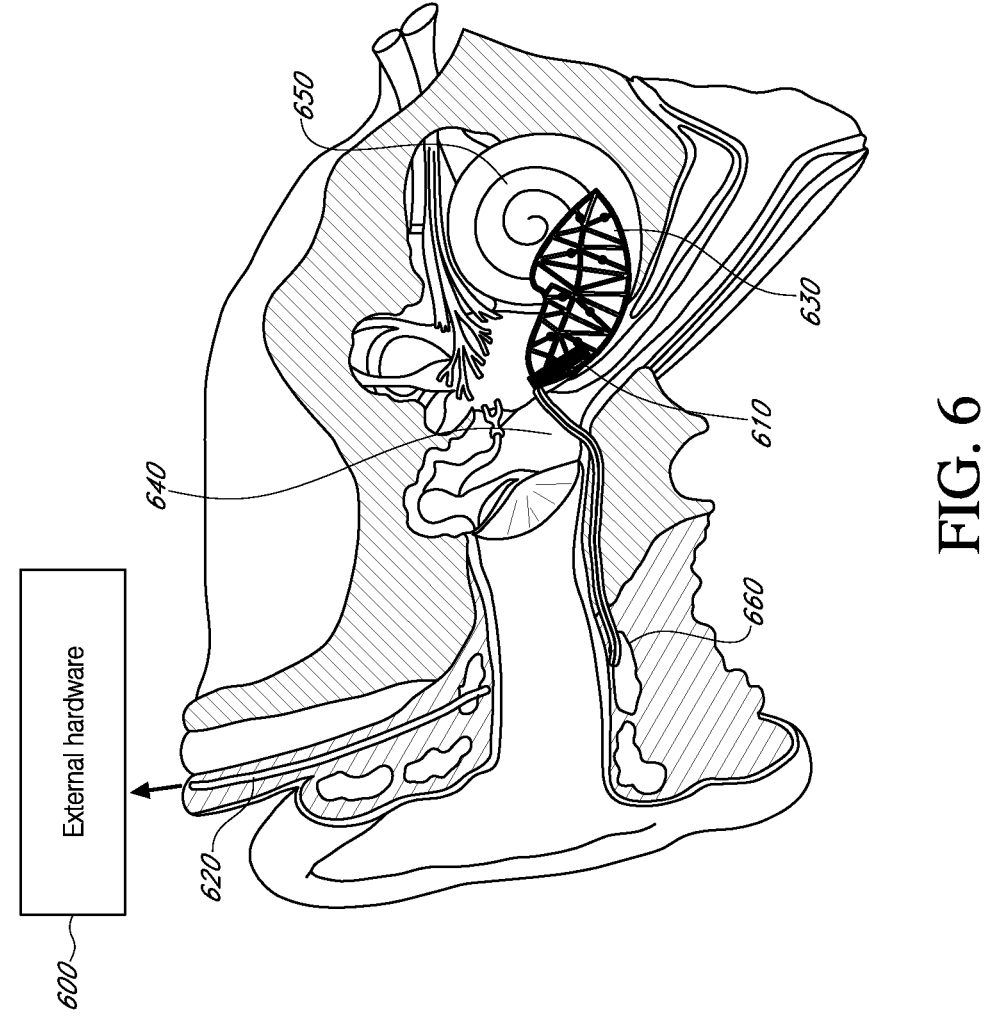
FIG. 6 shows one embodiment of an energy delivery element attached to a stimulator via a cable routed through a transcanal approach and connected to a stimulator located behind the ear.

FIG. 6 shows a transcanal (also known as Veria) method of implant delivery. Any of the components, for example energy delivery element 630, described herein may be delivered through a transcanal approach 660. The method includes an endaural or retroauricular incision and elevation of the tympanomeatal flap 766 (shown in FIG. 7) to expose the middle ear cavity 640. Optionally, the method may further include drilling a canal through the external auditory canal for lead 620 placement between subsets of the internal hardware and, in some embodiments, the external hardware 600 (e.g., microphone, speech processor, transmitter, etc.). In some embodiments, lead 620 may include local return electrodes. Lead 620 may electrically couple the external hardware 600 to the implanted components, for example receiver/stimulator (not shown), a local control unit 610, and energy delivery element 630. In some embodiments, the receiver/stimulator can be in wireless electronic communication with the external hardware 600. Energy delivery element 630 is attached or coupled to an external surface of the cochlea 650, using any of attachment methods described elsewhere herein. Alternatively, in other embodiments, the control unit 610 comprises the receiver/stimulator.

Figure 7:
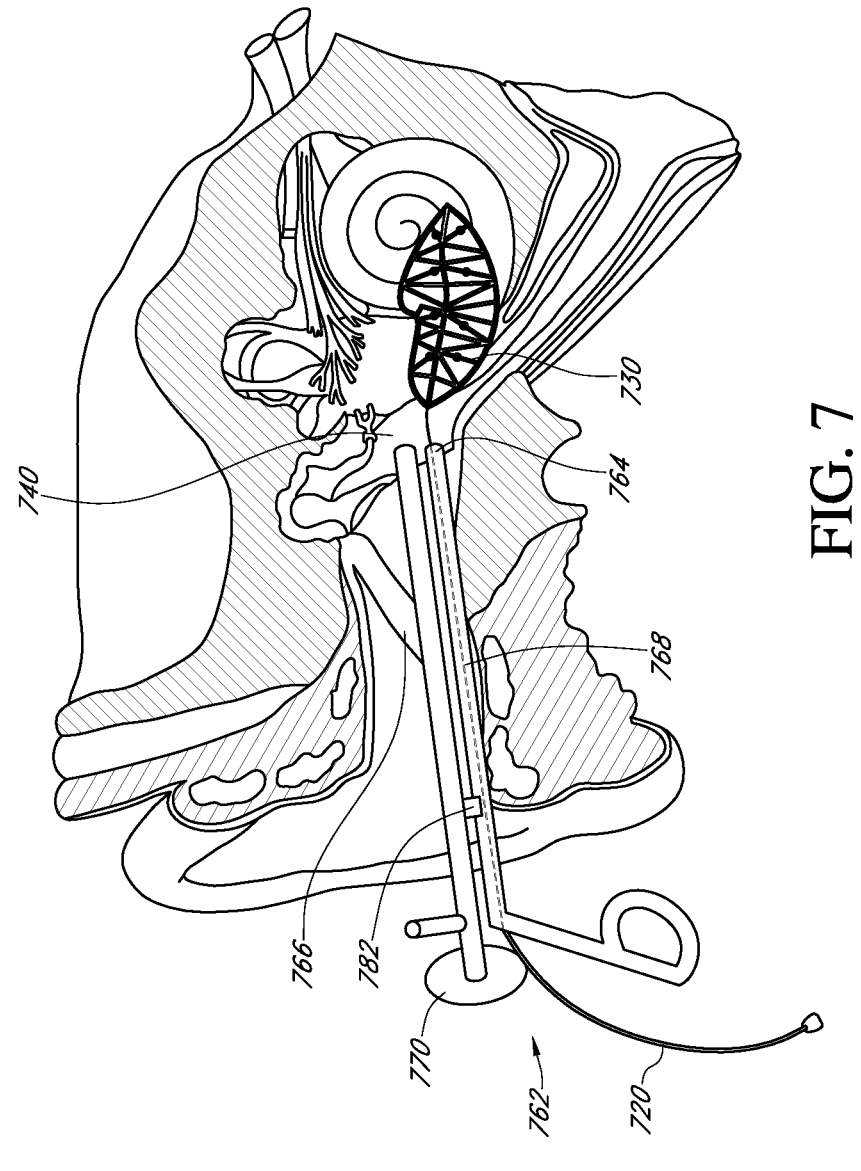
FIG. 7 shows another embodiment of an energy delivery element that is delivered to the middle ear and cochlear promontory through a transcanal approach.

In some embodiments of FIG. 6, a delivery system 770 may be used to deliver one or more implantable or internal components, for example energy delivery element 730, into the middle ear cavity 740, as shown in FIG. 7. The delivery system 770 allows for the energy delivery element 730 to be conformed for delivery through a catheter or instrument that is passed through the opening created surgically between the ear canal and the bony wall of the ear canal. This delivery system 770 allows for lead 720 to connect the energy delivery element 730 to the receiver/stimulator (not shown), which in this embodiment may be implanted post auricularly or worn as part of the external componentry. The catheter may include an elongate body 768 having a proximal end 762 and distal end 764 and defining a lumen. The electrode array or other internal components may be inserted into the catheter at a proximal end 762 and then advanced, for example using a pusher or plunger, to the distal end 764 for positioning in the middle ear cavity 740. Alternatively, catheter 770 may include a hinge 782, such that at least a portion of the elongate body 768 of the catheter opens about hinge 782 to release the electrode array 730 or other internal components into the middle ear cavity 740.

In still other embodiments, any of the internal components described herein may be delivered through the nose via the eustachian tube that connects the middle ear to the upper part of the throat behind the nose (the sidewall of the nasopharynx). In variations of this delivery method, any portion of this passageway may be dilated, for example using a dilator balloon or the like, before or during component delivery to the middle ear cavity.

Figure 72:
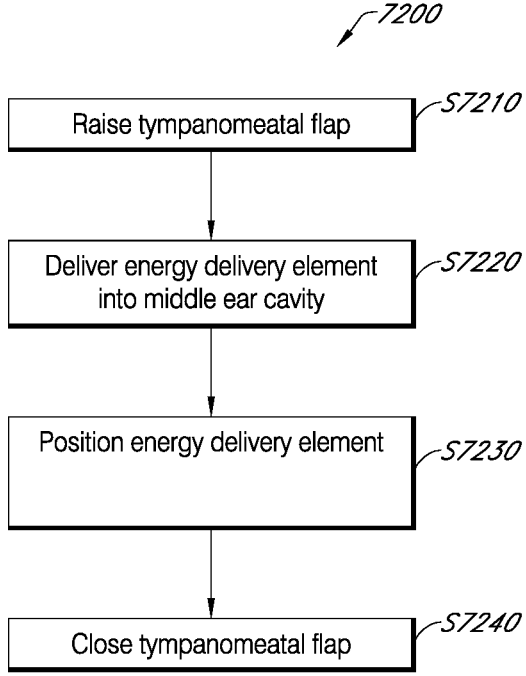
FIG. 72 shows one embodiment of a method of delivering an energy delivery element through a transcanal approach.

One embodiment of a transcanal method 7200, as shown in FIG. 72, for delivering an energy delivery element includes: raising a tympanomeatal flap at block S7210; delivering, using any of the tools and/or energy delivery element configurations described elsewhere herein, an energy delivery element into the middle ear cavity at block 57220; positioning an energy delivery element at block 57230; and closing the tympanomeatal flap at block 57240. As appreciated by one of skill in the art, any of the method steps may be performed in any order or combined.

In some embodiments, positioning an energy delivery element comprises positioning the element either under direct visualization or with an endoscope. Additionally, or alternatively, positioning the energy delivery element comprises using one or more locating features of the device. For example, a locating feature may include a concave section, a bevel, a raised edge, or the like.

Figure 73:
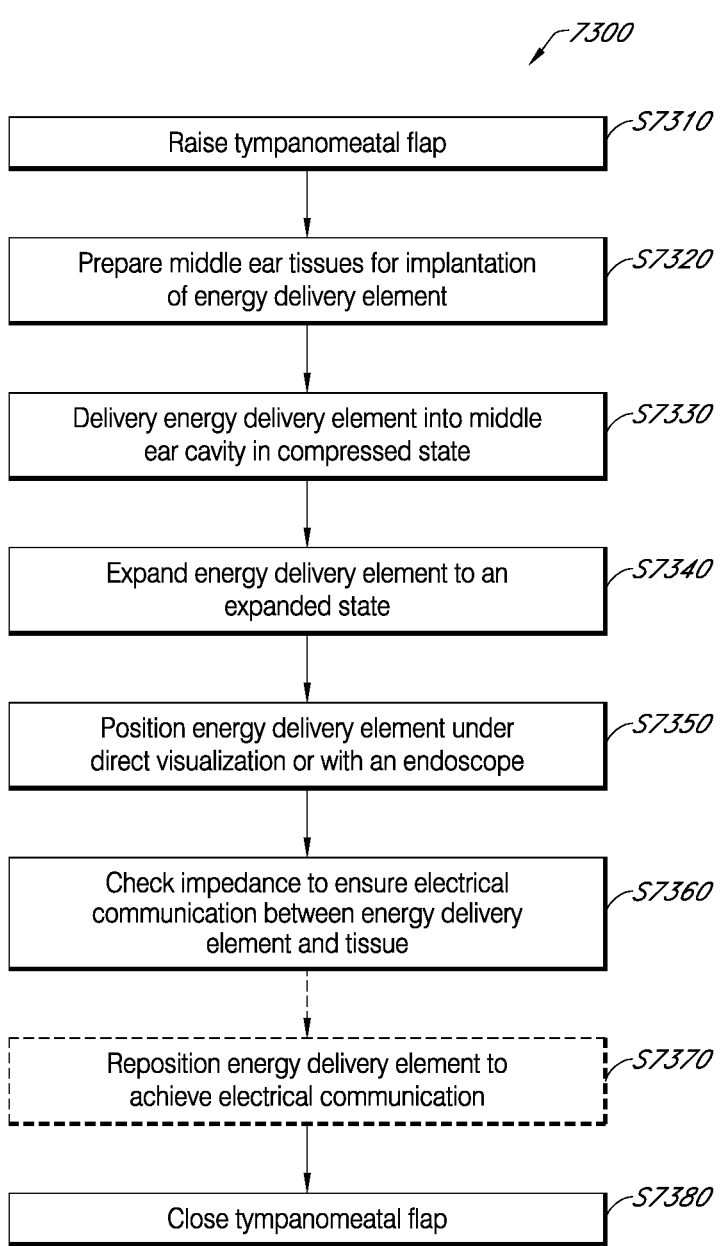
FIG. 73 shows another embodiment of a method of delivering an energy delivery element through a transcanal approach.

Another embodiment of a transcanal method 7300, as shown in FIG. 73, for delivering an energy delivery element includes: raising a tympanomeatal flap at block 57310; preparing (using any of the methods described elsewhere herein) one or more middle ear tissues for implantation of an energy delivery element at block 57320; delivering an energy delivery element into middle ear cavity in a compressed state at block 57330; expanding, actively or passively, the energy delivery element to an expanded state or configuration at block 57340; positioning the energy delivery element under direct visualization or with an endoscope at block 57350; checking impedance to ensure electrical communication between energy delivery element and tissue at block 57360; optionally (shown in dashed lines), repositioning the energy delivery element to achieve electrical communication at block S7370; and closing the tympanomeatal flap at block 57380. As appreciated by one of skill in the art, any of the method steps may be performed in any order or combined.

In some embodiments, checking impedance comprises connecting the energy delivery element to an impedance measurement tool or an interface that connects to a computer that is configured to show impedance across the electrode contacts. The impedance measurement tool may be a simple sterile tool that is provided with each energy delivery element that could be positioned within the surgical field in wireless communication with the implantable stimulator (connected to the electrode). Such tool would be configured to display electrode impedances and, optionally, a level of interpretation (e.g., a visual indicator showing that the electrode is positioned for optimal impedance).

Figure 74:
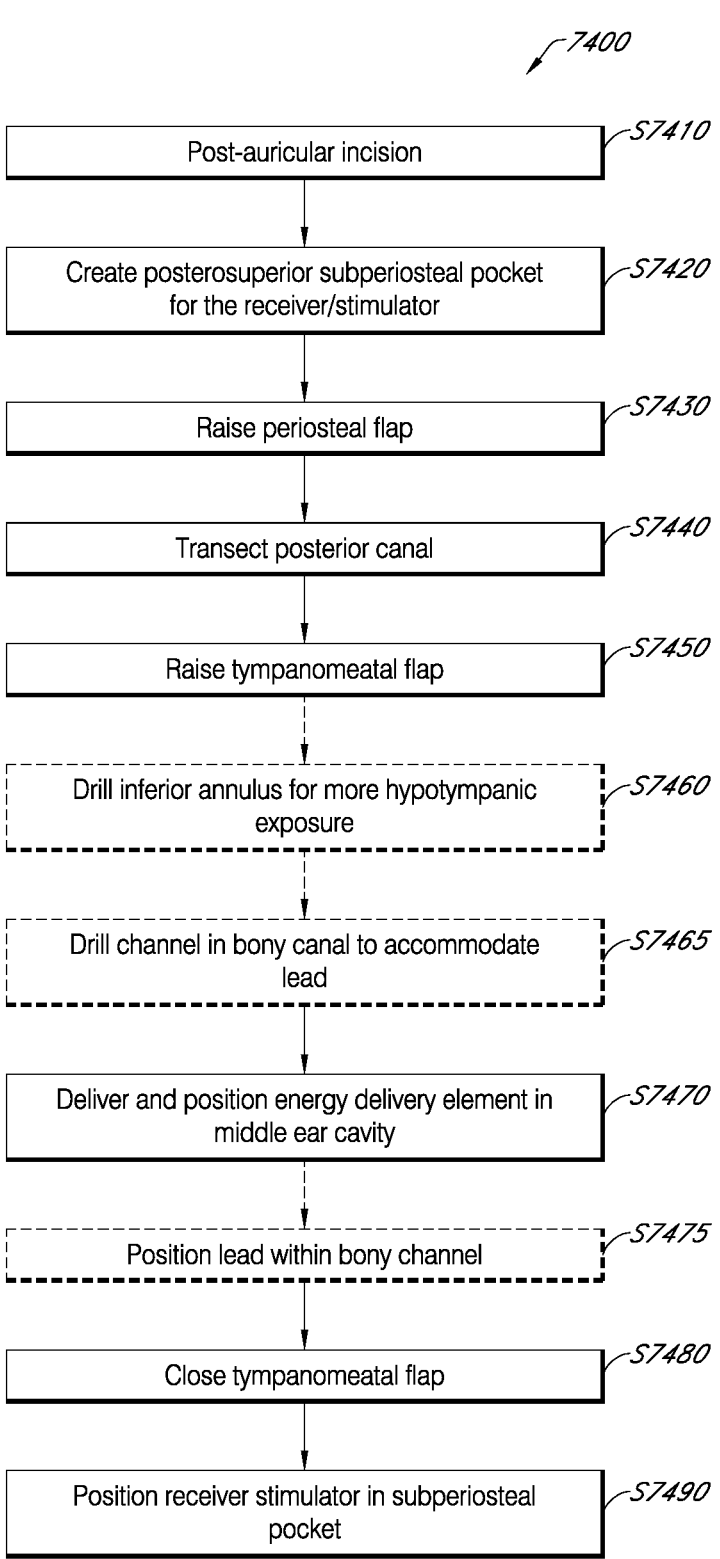
FIG. 74 shows another embodiment of a method of delivering an energy delivery element through a transcanal approach.

Another embodiment of a transcanal method 7400, as shown in FIG. 74, for delivering an energy delivery element includes: creating a post-auricular incision at block S7410; creating a posterosuperior subperiosteal pocket for the receiver/stimulator at block S7420; raising a periosteal flap at block 57430; transecting a posterior canal at block 57440; raising a tympanomeatal flap at block 57450; drilling an inferior annulus for increased hypotympanic exposure at block 57460; drilling a channel in a bony canal to accommodate lead at block 57465; delivering and positioning an energy delivery element in a middle ear cavity at block 57470; positioning lead within the channel at block 57475; closing the tympanomeatal flap at block 57480; and positioning a receiver stimulator in subperiosteal pocket at block 57490. As appreciated by one of skill in the art, any of the method steps may be performed in any order or combined.

Figure 77:
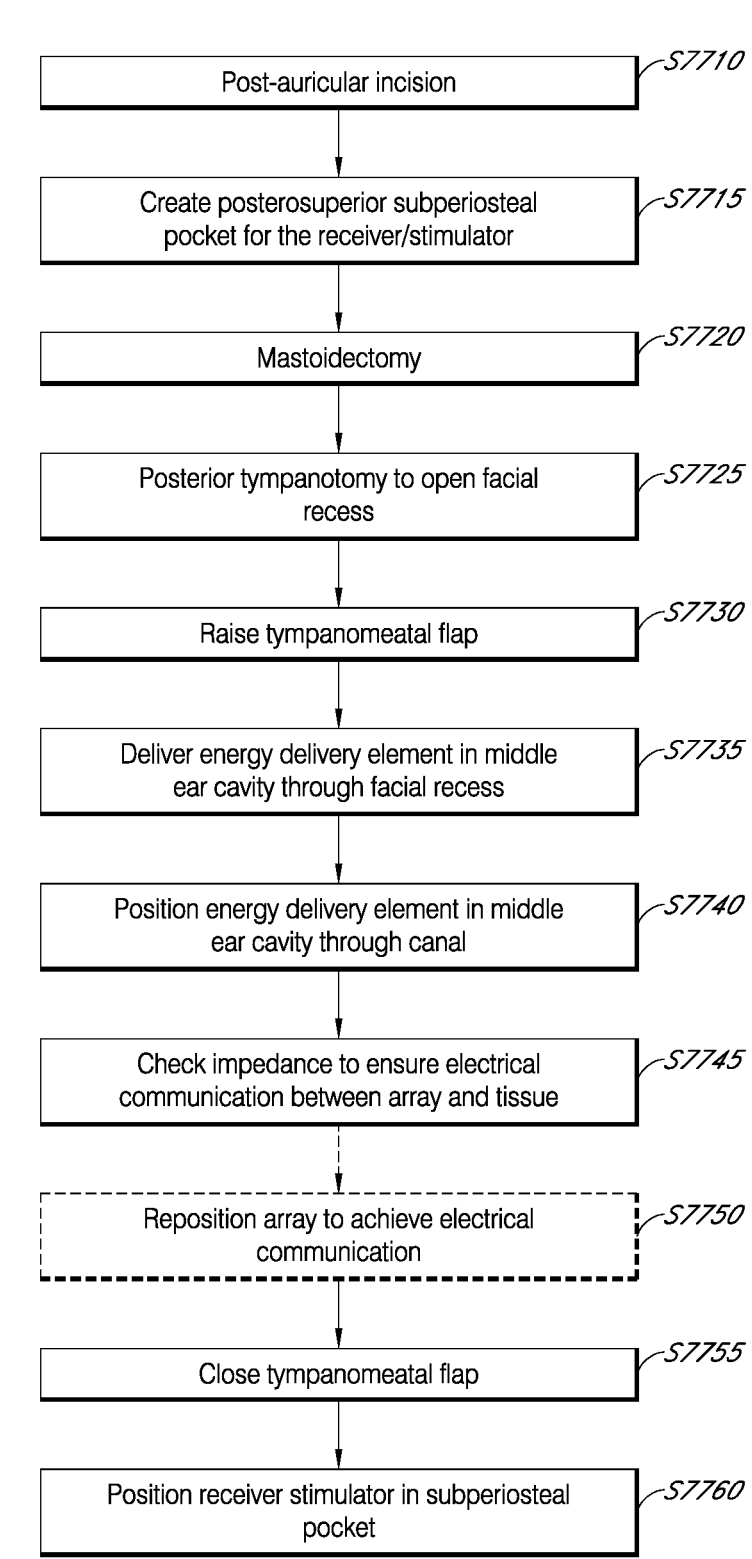
FIG. 77 shows another embodiment of a method of delivering an energy delivery element through a facial recess approach.

A method 7700, as shown in FIG. 77, of delivering an energy delivery element using a combined facial recess and transcanal approach includes: creating a post-auricular incision at block 57710; creating a posterosuperior subperiosteal pocket for the receiver/stimulator at block 57715; performing a mastoidectomy at block 57720; performing a posterior tympanotomy to open a facial recess at block 57725; raising a tympanomeatal flap at block S7730; delivering an energy delivery element into the middle ear cavity through the facial recess at block 57735; positioning the energy delivery element in the middle ear cavity through a canal at block 57740; checking impedance, as described above, to ensure electrical communication between energy delivery element and tissue at block 57745; optionally (shown using dashed lines), repositioning the energy delivery element to achieve electrical communication at block 57750; closing a tympanomeatal flap at block 57755; and positioning a receiver stimulator in subperiosteal pocket at block 57760. As appreciated by one of skill in the art, any of the method steps may be performed in any order or combined.

Figure 8:
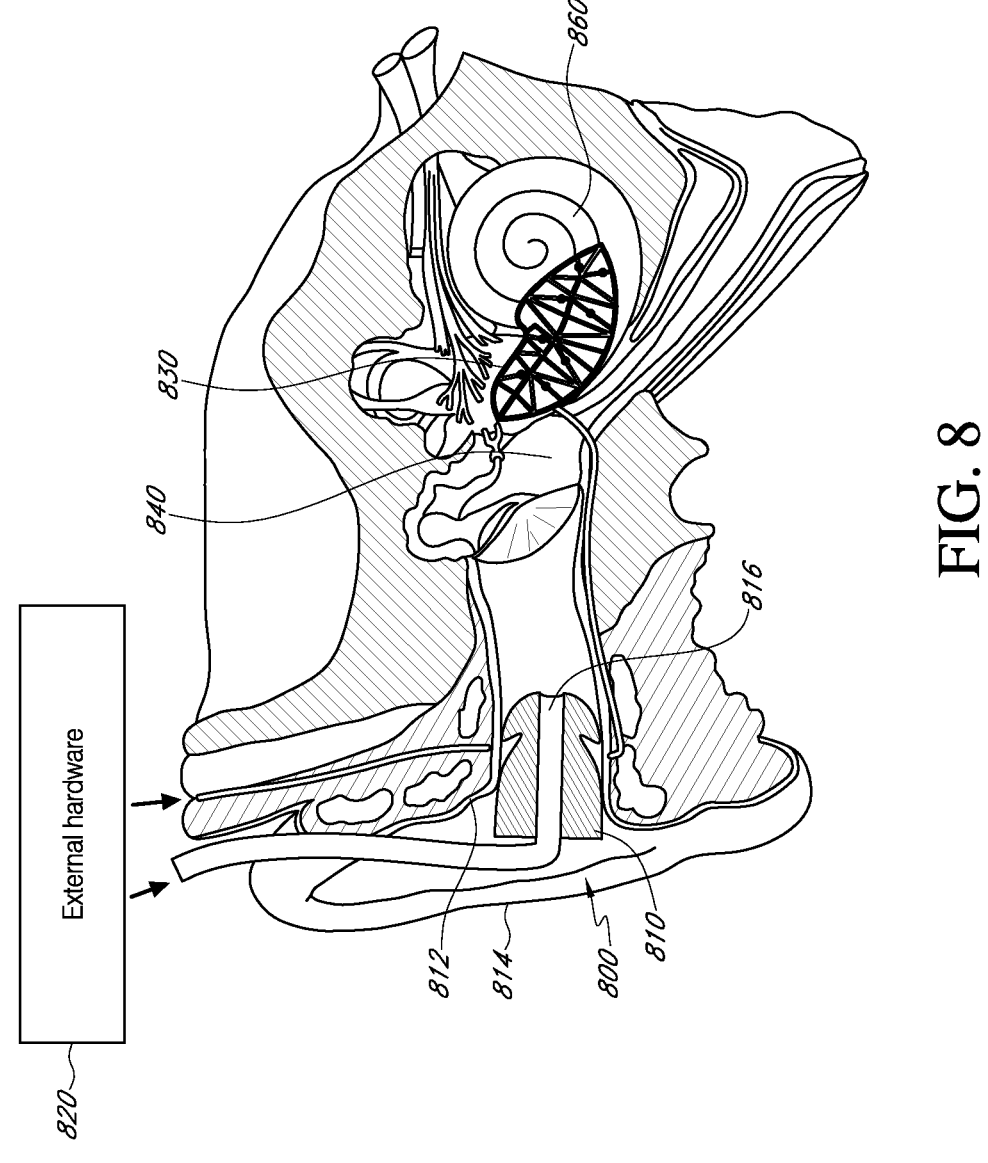
FIG. 8 shows a combination of an energy delivery element for electrical stimulation of high frequencies with acoustic sound wave amplification of lower frequencies.

In some embodiments, as shown in FIG. 8, a system for improving hearing in a subject in need thereof may include an acoustic amplifier 800 of one or more frequency ranges, as described above. For example, in some embodiments, the energy delivery element 830 may be positioned and configured to stimulate high frequency hearing while the acoustic amplifier 800 may be configured to amplify lower frequency ranges. Such acoustic amplifier 800 may be used with any of the device or system embodiments described herein. The acoustic amplifier 800 may comprise an occluding member or plug 810 positioned in an external meatus 812 of the ear 814. The occluding member 810 may define a passageway 816 through which acoustic waves are delivered into the middle ear cavity 840 in synchrony with the electrical stimulation provided by an energy delivery element 830 positioned on an external surface of the cochlea or in a middle ear cavity. Energy delivery element 830 and acoustic amplifier 800 are electrically coupled to external hardware 820, including a receiver/stimulator, speech processor (e.g., to determine sounds for amplification versus electrical stimulation via the electrode array), microphone, etc.

Figure 9A:
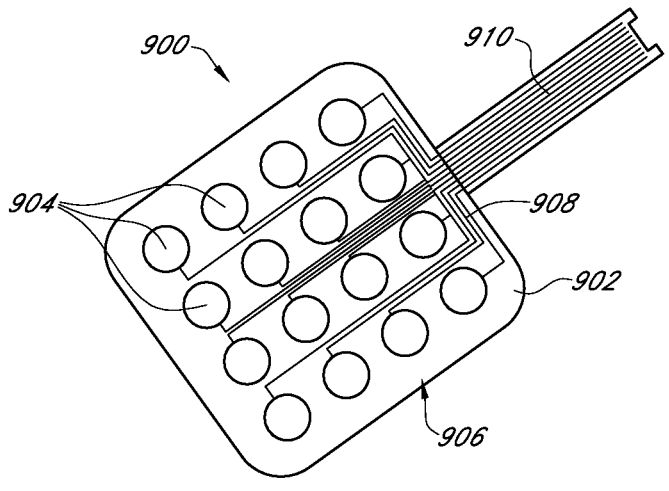
FIG. 9A shows a perspective view of a configuration of electrodes on an array surface.
Figure 9B:
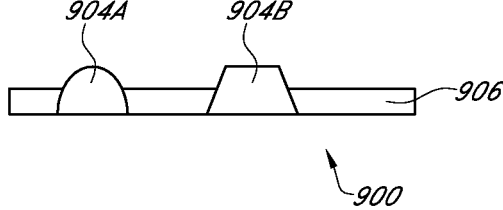
FIG. 9B shows a side view of two different shapes of an energy delivery element.
Figure 9C:
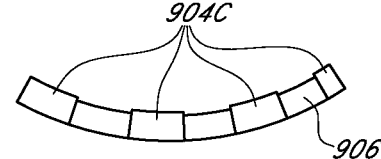
FIG. 9C shows a side view of a flexed configuration of at least part of an energy delivery element.

FIGS. 9A-9C show various views of one embodiment of an energy delivery element 900 for a device for extracochlear stimulation. FIG. 9A shows a view of the surface of the energy delivery element 900 adapted for contact with an external surface of the cochlea in a middle ear. As defined herein, the surface for contact with the external surface of the cochlea will be referred to as the "front" side or "top" side or surface 902 of the electrode array 900. In many embodiments, the front side 902 can feature one or more exposed electrode heads 904 secured in or on a substrate 906. In some embodiments the substrate 906 is made of an elastomeric material, such as PDMS or silicone, in order to allow the electrode array 900 to contort, bend, or flex to conform to the curvature or uneven topography of the surface on which it is placed (e.g., the cochlear promontory). In other embodiments, the substrate 906 can comprise various structural components forming internal structures (not shown) to provide additional support and/or to affect the desired shape of the energy delivery element 900. These internal structures can comprise materials including, but not limited to: nitinol, titanium, hydrogel, stainless steel, polycarbonate, acrylic, or a combination thereof, where the internal structures may be chosen based on the desired shape of the array or attachment and/or desired positioning within the middle ear cavity. In further embodiments, the substrate 906 can comprise a rigid substrate, including but not limited to: FR-4, CMOS chip, polycarbonate, acrylic materials, or a combination thereof.

In the embodiment of FIG. 9A, the electrodes heads 904 can comprise silver, gold, platinum, Pt—Ir, coated Pt, nickel, brass, copper, metallic alloy, graphite, Titanium Nitride (TiN) and/or SIROF. In certain embodiments, the electrode heads 904 are platinum-iridium electrodes. Furthermore, in this embodiment, the electrode heads 904 have a fixed shape. In various embodiments, the electrode heads 904, individually, in subsets, or as a whole, can each have a flat, sloped, concave, or convex shape, in addition to an overall geometry of circles, squares, lines, spheres, cones, cylinders, bars, stars, and/or concentric circles, where the geometry may be chosen to promote spatially selective electrical stimulation, in order to maximize contact with the promontory as appropriate. The electrode heads 904 can be arranged in various patterns across different embodiments, including, but not limited to, hexagonal, radially, linear, concentric, saw-tooth, rectilinear, and/or offset arrangements. In the embodiment of FIG. 9A, the electrode heads 904 are arranged in a linear grid. In other embodiments, the electrode heads 904 can be arranged in radial patterns and uneven clusters. Furthermore, in alternative embodiments, non-fixed electrode contacts, including but not limited to: spring probes, leaf springs, or spring coils, where the material of the substrate and electrode type, may be chosen to accommodate the curvature and topography of the external surface of the cochlea. In still further alternative embodiments, electrodes or substrates configured with sharp features (e.g., spikes, barbs, protrusions, tissue piercing elements, etc.) may be used to couple the energy delivery element to an external surface of the cochlea. In additional embodiments, the electrode heads 904 can be coated in various materials to promote biological compatibility and/or integration. For example, the electrode heads 904 can be coated with hydroxyapatite to promote ossification and thus integration with the promontory surface.

In many embodiments, each electrode head 904 can be powered by at least one electrode connector 908. Though depicted in FIG. 9A for clarity, the electrode connectors 908 are internal to substrate 906 and therefore insulated from each other and the biological environment of the cochlear surface, in many embodiments. The electrode connectors 908, in many embodiments, congregate or are bundled to at least partially comprise a lead 910 that connects the energy delivery element 900 to other components of the device such as a multiplex control unit and/or a pulse stimulation generator of FIG. 2.

FIG. 9B shows a profile view in cross-section of a portion of one embodiment of an energy delivery element 900. Two electrode heads 904A and 904B are shown at least partially embedded in a substrate 906, as described herein. In this example, electrode head 904A has a domed or convex shape while electrode head 904B has a flat head. As described herein, the electrode heads 904 can take various shapes (see, e.g., FIGS. 48A-48F).

FIG. 9C shows a profile view in cross-section of a portion of another embodiment of an energy delivery element 900. In this embodiment, the substrate 906 has a convex shape in order to maximize contact with the cochlear surface. Additionally, the electrode heads 904C can also have a convex shape to similarly maximize contact.

Figure 10A:
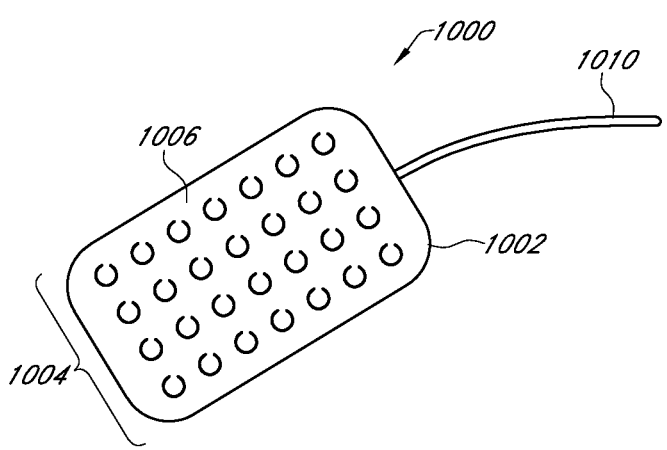
FIG. 10A shows a front view of another embodiment of an electrode configuration of an energy delivery element.
Figure 10B:
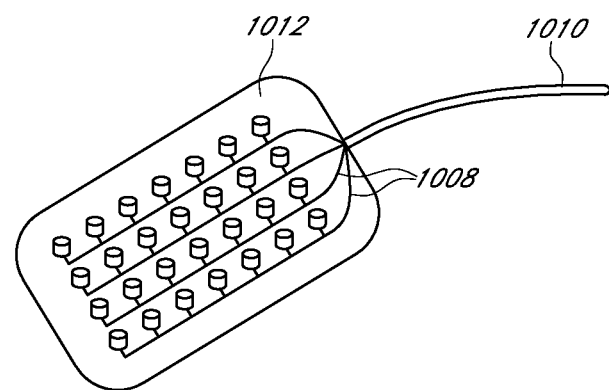
FIG. 10B shows a back view of the embodiment of FIG. 10A.
Figure 10C:
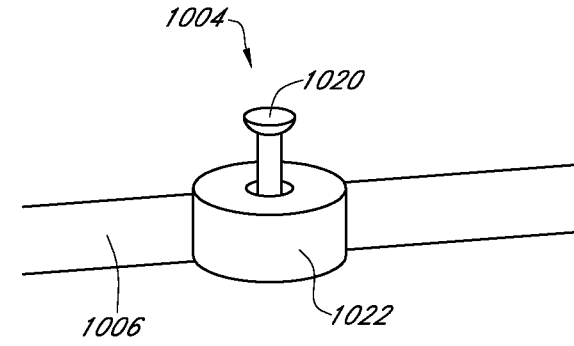
FIG. 10C shows a zoomed-in view of the embodiment of FIG. 10A.

FIGS. 10A-10C show various views of another embodiment of an energy delivery element 1000 of a device for extracochlear stimulation. FIG. 10A shows a perspective view of a front side 1002 of the energy delivery element 1000 that comprises a plurality of electrode heads 1004 embedded in or on a substrate 1006. As described herein, the substrate 1006 can comprise an elastomeric or rigid material, as described herein elsewhere herein. In the embodiment of FIG. 10A, the electrode heads 1004 are non-fixed electrode contacts shown in more detail in FIG. 10C and are arranged in a linear grid. FIG. 10B shows a perspective view of a back side 1012 of one embodiment of the electrode array 1000 that is shown as partially transparent in order to illustrate the electrode connectors 1008 that at least partially comprise a lead 1010, as described herein.

FIG. 10C shows a zoomed-in view of one embodiment of a non-fixed electrode contact 1004. In this embodiment, the electrode contact 1004 comprises a electrode contact pogo pin 1020 supported by a spring (not shown) stored within a pin housing 1022. The electrode contact pogo pin 1020 is electrically conductive and capable of delivering electrical stimulation to a biological surface (e.g., the promontory of the middle ear), and thus can comprise various materials appropriate for doing so, including, but not limited to: platinum-iridium alloys, as well as other electrode materials as described herein. Because the pogo pin 1020 is supported on a spring, the pogo pin 1020 is capable of moving within a certain range, determined by the spring, in towards and out from the substrate 1006. Therefore, in embodiments where the substrate 1006 is insufficiently flexible to exactly match the contours of the cochlea, the spring-loaded pogo pin 1020 can thus extend or compress as needed in order to maintain contact with the biological surface. The pin housing 1022 provides structural support for the spring and protects it from the biological surface.

Figure 11A:
FIGS. 11A-11C show various steps of a method of energy delivery element attachment that comprises implanting the array in the submucosal space underlying the cochlea promontory.
Figure 11B:
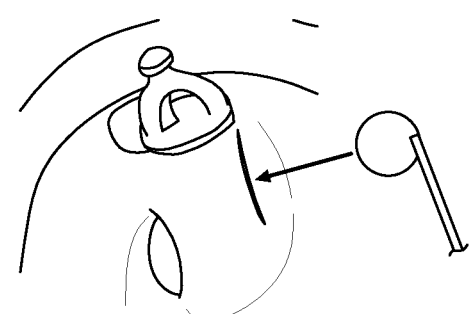
Figure 11C:
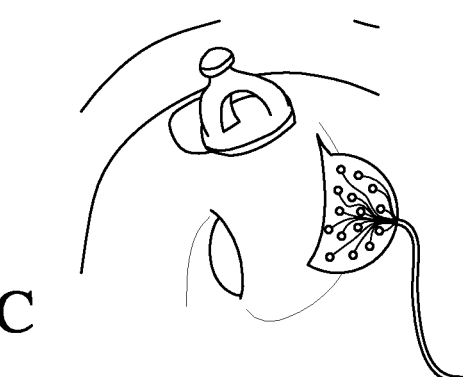

FIGS. 11A-11C show a method of electrode array delivery and/or attachment to an external surface of the cochlea. Turning to FIG. 11A, the method includes opening or accessing a submucosal cavity of a promontory of a cochlea. Such opening or access may be achieved by cutting or creating an incision in a surface of the submucosa. As shown in FIG. 11B, the method includes preparing the cavity in the submucosa. Preparing may include, for example, inserting a rigid body (e.g., template tool) into the cavity, sliding a tool through the cavity (e.g., to remove debris or obstructions), and/or removing or withdrawing the rigid body or tool from the cavity. The rigid body may be shaped and sized such that it has dimensions only slightly larger than that of the energy delivery element that will be inserted into the cavity. The method further includes, as shown in FIG. 11C, inserting an energy delivery element into the cavity with the electrodes facing downward toward the cochlea. The method may further include verifying an impedance or contact of the energy delivery element against the cochlear surface and, optionally, adjusting a positioning of the electrode array when the impedance measurements determine that one or more of the energy delivery elements are not fully coupled to the cochlear surface to delivery stimulation. In some embodiments, the method includes sealing the cavity after the energy delivery element is positioned therein, for example with glue, one or more sutures, a tissue growth promoting hormone, etc.

Figure 12:
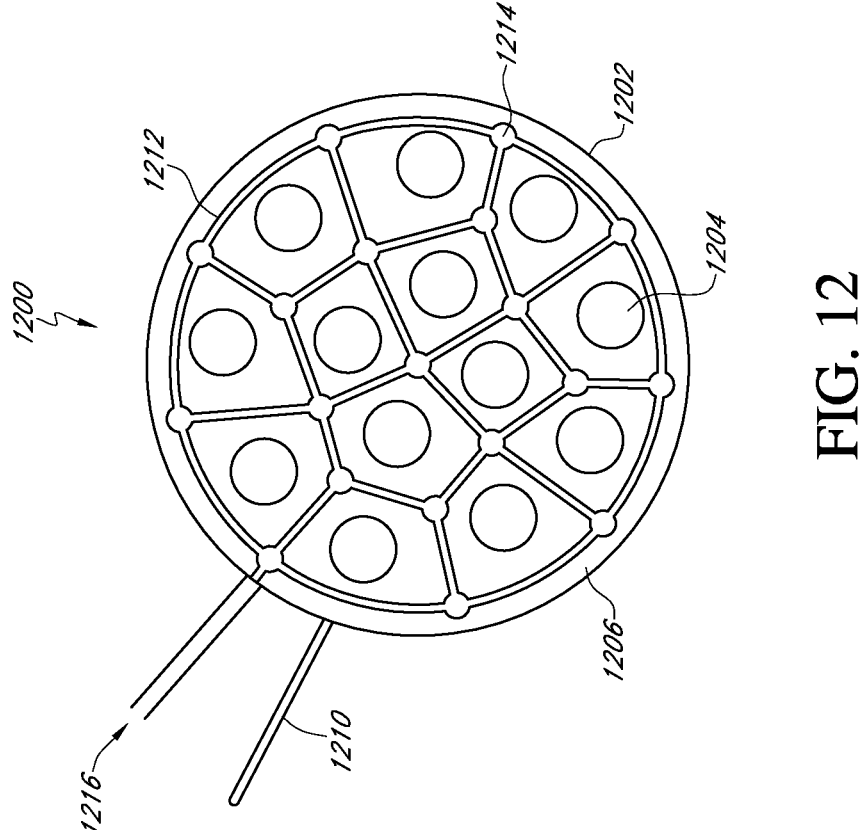
FIG. 12 shows another method of energy delivery element attachment that comprises a capillary network of adhesive and associated device structure.

FIG. 12 shows a view of a front side of one embodiment of an energy delivery element 1200 for a device for extracochlear stimulation. In this embodiment, the energy delivery element 1200 comprises a plurality of exposed electrode heads 1204 embedded in a radial pattern in a substantially circular substrate 1206. The electrode heads 1204 and substrate 1206 can comprise various materials, as described herein. A lead 1210 can connect the electrode array 1200 to other components (not shown) of the device. as described herein. FIG. 12 shows the electrode array 1200 as partially transparent in order to depict a series or web of hollow capillary tubes or microchannels 1212 that run throughout the interior of the substrate 1206. At various locations along the web of capillary tubes or microchannels 1212, such as at a vertex where two or more tubes 1212 meet, a perforation or pore 1214 is present in a front side 1202 or tissue facing side of the array, connecting the capillary tubes 1212 to the exterior surface of the array 1200. In some embodiments, the system of capillary tubes 1212 and perforations 1214 allow for the use of an adhesive during an implantation procedure of the array 1200. For example, while the array 1200 is temporarily held in place by physical force (e.g., a surgeon's tool, an inflated balloon, deformable material, spring, pillar, etc.) on the biological surface to which it is to be attached, a tool or pipette or catheter 1216 can deliver a quantity of adhesive into the capillary tubes 1212 such that adhesive spills out of the perforations 1214 and onto the biological surface. When the adhesive dries or cures, the array 1200 will then be secured to the surface by the adhesive, and the temporary force can be removed. In certain embodiments, the adhesive can comprise cyanoacrylate although other adhesives can be used across many embodiments, for example bone wax, bone cement, or bioceramics, such as bioactive glass, tricalcium silicate, or calcium phosphate. In some embodiments, the adhesive may be cured using one or more of: ultraviolet light, heat, or an accelerant. Alternatively, or additionally, curing of the adhesive may be activated by laser light.

Figure 13:
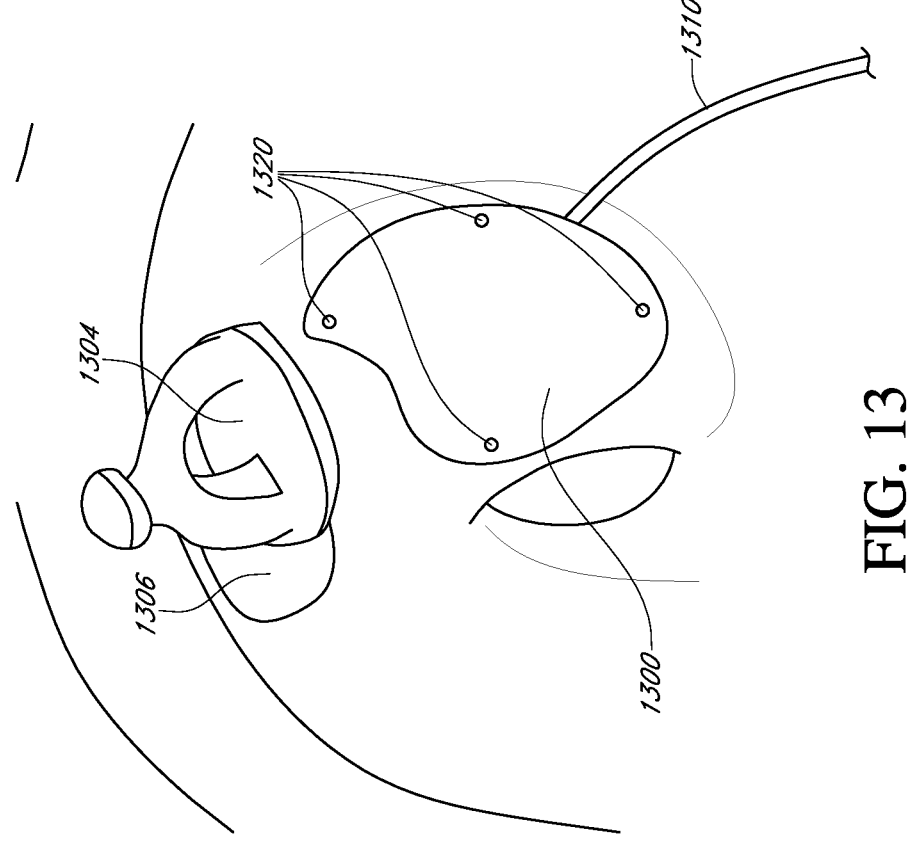
FIG. 13 shows one embodiment of an energy delivery element that is sized and shaped to cover the cochlear promontory while not interfering with the stapes or stapes footplate.
Figures 14A, 14B, 14C, 14D:
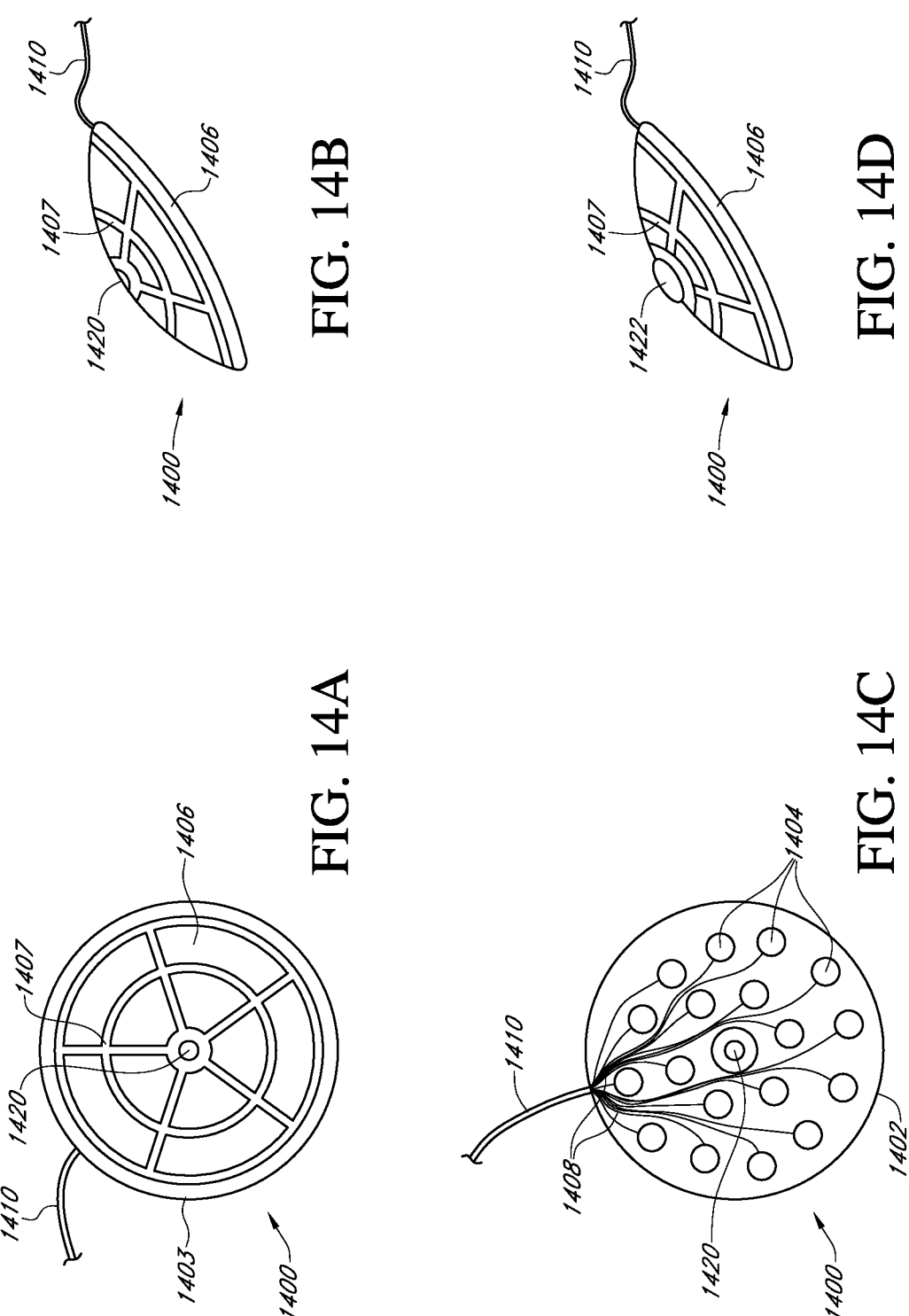
FIG. 14A show a perspective view of a back side of an energy delivery element.
FIG. 14B shows a perspective side view of the embodiment of FIG. 14B without the fixation screw.
FIG. 14C shows a view of the front side 1402 of the embodiment of FIG. 14A, that is configured to contact at least a portion of a cochlea.
FIG. 14D shows a perspective side view of the embodiment of FIG. 14B with the presence of the fixation screw through an aperture.

FIG. 13 illustrates the placement of another embodiment of an energy delivery element 1300 over an external surface of the cochlea. In various embodiments, the energy delivery element 1300 may be circular, oval, or irregularly shaped but may avoid interference with other structures within the middle ear. In particular, the energy delivery element may not interfere with the stapes 1304 or stapes footplate 1306. In the embodiment of FIG. 13, the energy delivery element 1300 has a characteristic shape that accommodates for the stapes footplate while maximizing contact with the surface of the promontory. Furthermore, the energy delivery element 1302 can be secured to the cochlea by one or more mechanical fixtures 1320 (e.g., fixation screws) that traverse at least a portion of the energy delivery element 1300 into the tissue, in some embodiments. In the particular embodiment of FIG. 13, four fixation screws 1320 are present along the perimeter of the back face of the electrode array 1300. Other numbers and positions of fixation screws 1320 are possible in alternative embodiments. A lead 1310 can connect the array 1300 to other components of the device as described herein FIGS. 14A-14D show various views of another embodiment of an energy delivery element 1400 for extracochlear stimulation. FIG. 14A show a perspective back view of a back side 1403 of the energy delivery element 1400 comprising a substrate 1406 that is shown as partially transparent in order to depict a supporting internal structure 1407. The internal structure 1407, in various embodiments, can comprise materials including, but not limited to: nitinol, titanium, hydrogel, stainless steel, polycarbonate, or acrylic, and can have a shape, pattern, or arrangement (e.g., a radial web as shown in FIG. 14A) chosen based on the desired shape of the array or attachment and/or desired positioning within the middle ear cavity. The internal structure 1407 can assist in supporting the electrode array 1400 in conforming to the surface of the cochlea in order to maximize its contact with the electrodes 1404 on the front side 1402 of the array

1400. In the embodiment of FIGS. 14A-14D, the array 1400 defines an aperture 1420 (e.g., may be centrally located, peripherally, or otherwise) that traverses the thickness of the substrate 1406. The aperture 1420, in this embodiment, is adapted to receive a singular fixation screw 1422 that secures the array 1400 to the cochlea. In the view offered by FIG. 14A, the fixation screw 1422 is absent from the array 1400. A lead 1410 can connect the array 1400 to other components of the device, as described herein. FIG. 14B shows a perspective side view of the array 1400, similarly lacking the fixation screw 1422 and showing the substrate 1406 as partially transparent in order to illustrate the internal structure 1407. From this perspective, the convex shape of the substrate 1406 is visible.

FIG. 14C shows a view of the front side 1402 of the array 1400 that comprises a plurality of exposed electrode heads 1404 arranged radially about the aperture 1420. The substrate 1406 in FIG. 14C is depicted as partially transparent in order to reveal the electrode connectors 1408, as described herein. In some embodiments, the front side 1402 of the array has a convex shape of the same or different curvature of the back side 1403 in order to maximize contact of the electrode heads 1404 to the cochlear surface. FIG. 14D shows a perspective side view of the array 1400 similar to the view of FIG. 14B except that FIG. 14D depicts the presence of the fixation screw 1422 through aperture 1420.

Figures 15A, 15B, 15C:
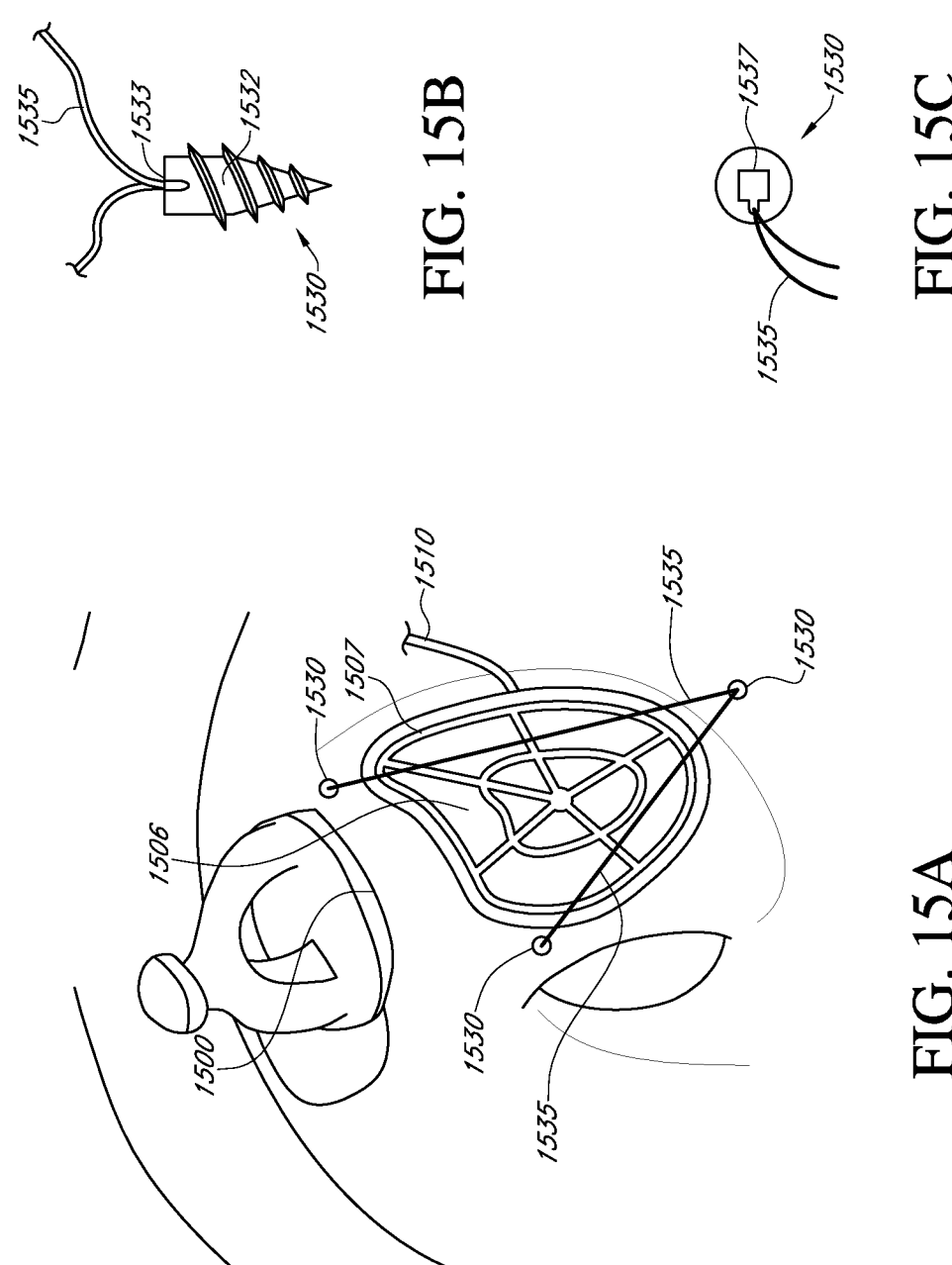
FIG. 15A shows another embodiment of an energy delivery element that is secured via suture anchors to a promontory surface of a cochlea.
FIG. 15B shows one embodiment of a suture anchor for use with the embodiment of FIG. 15A.
FIG. 15C shows a top view of the suture anchor of FIG. 15B depicting a polygonal drive.

FIG. 15A shows yet another embodiment of an energy delivery element 1500 that is secured using suture anchors 1530 that are placed just beyond the promontory surface in areas that are known to be safe to insert screws, such as the hypotympanum. To each suture anchor 1530, a suture 1535 comprising an absorbable nylon or elasticated material can be threaded, and the suture anchors 1530 are placed such that, once the energy delivery element 1500 is placed over the cochlear surface, the suture 1535 can be secured taut between the suture anchors 1530 and over the energy delivery element 1500 in order to hold the energy delivery element 1500 in place and to apply pressure on it, thus improving the electrical contact for the electrodes (not shown) of the energy delivery element 1500. In the embodiment of FIG. 15A, three suture anchors 1530 with one suture 1535 is used, although any number of suture anchors 1530 and sutures 1535 can be employed. In some embodiments, the system of the suture anchors 1530 and sutures 1535 can used as a temporary mechanism for securing the energy delivery element 1500 to the promontory to be replaced by a more permanent system. In some embodiments, the suture anchors 1530 and sutures 1535 are employed while adhesive cures or while the energy delivery element 1500 becomes osseo-integrated. In other embodiments, the system of suture anchors 1530 and sutures 1535 can be utilized as a permanent mechanism for securing the energy delivery element 1500 to the cochlea. In the example of FIG. 15A, the substrate 1506 of the energy delivery element 1500 is depicted as partially transparent in order to show a supporting internal structure 1507, as described herein. FIG. 15B shows a profile view of a suture anchor 1530 having a screw body 1532 with a suture 1535 passing through and/or secured to its top 1533. FIG. 15C shows a top view of a suture anchor 1530 depicting a square drive 1537. In alternative embodiments, other drive types (e.g., flathead, Phillips, etc.) can be employed without deviating from the scope of this disclosure.

Figure 16A:
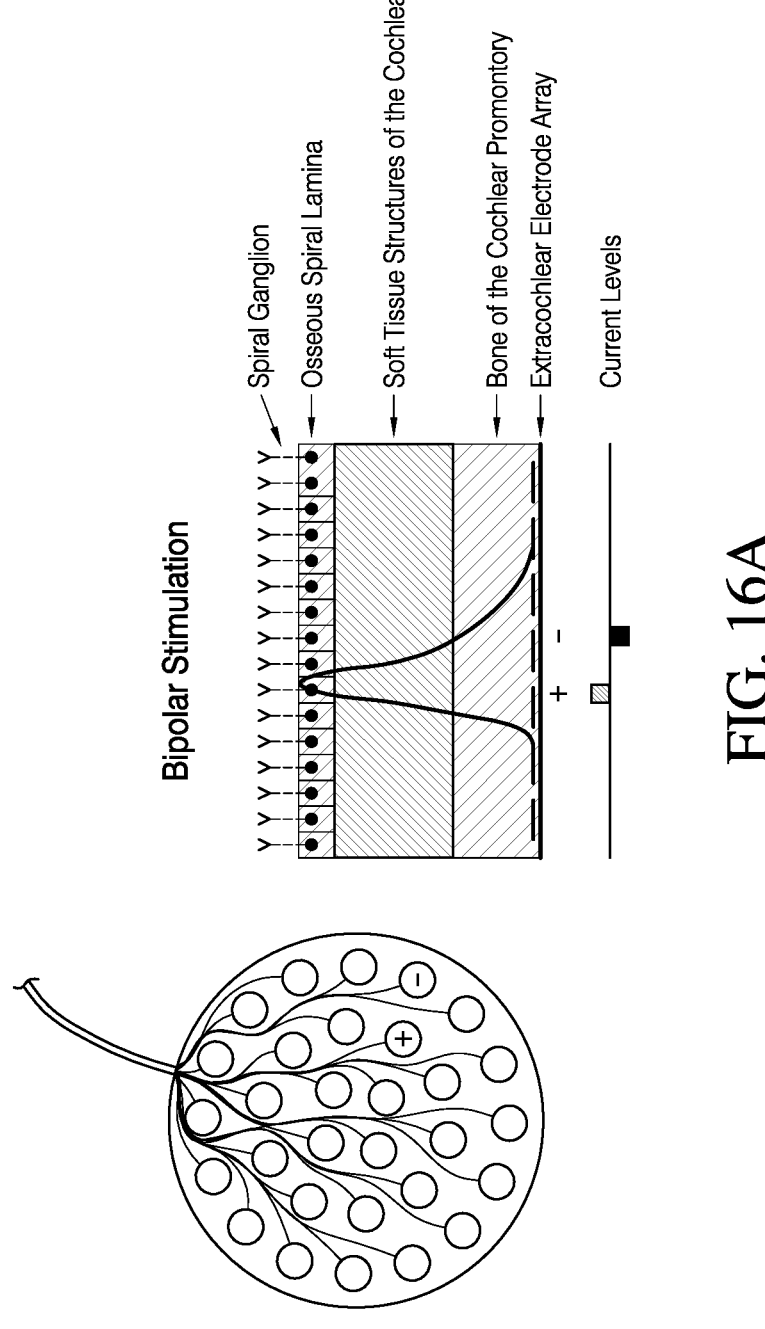
FIG. 16A shows a bipolar stimulation mode of an energy delivery element to optimize for tonotopic stimulation and restoration of hearing outcomes.
Figure 16B:
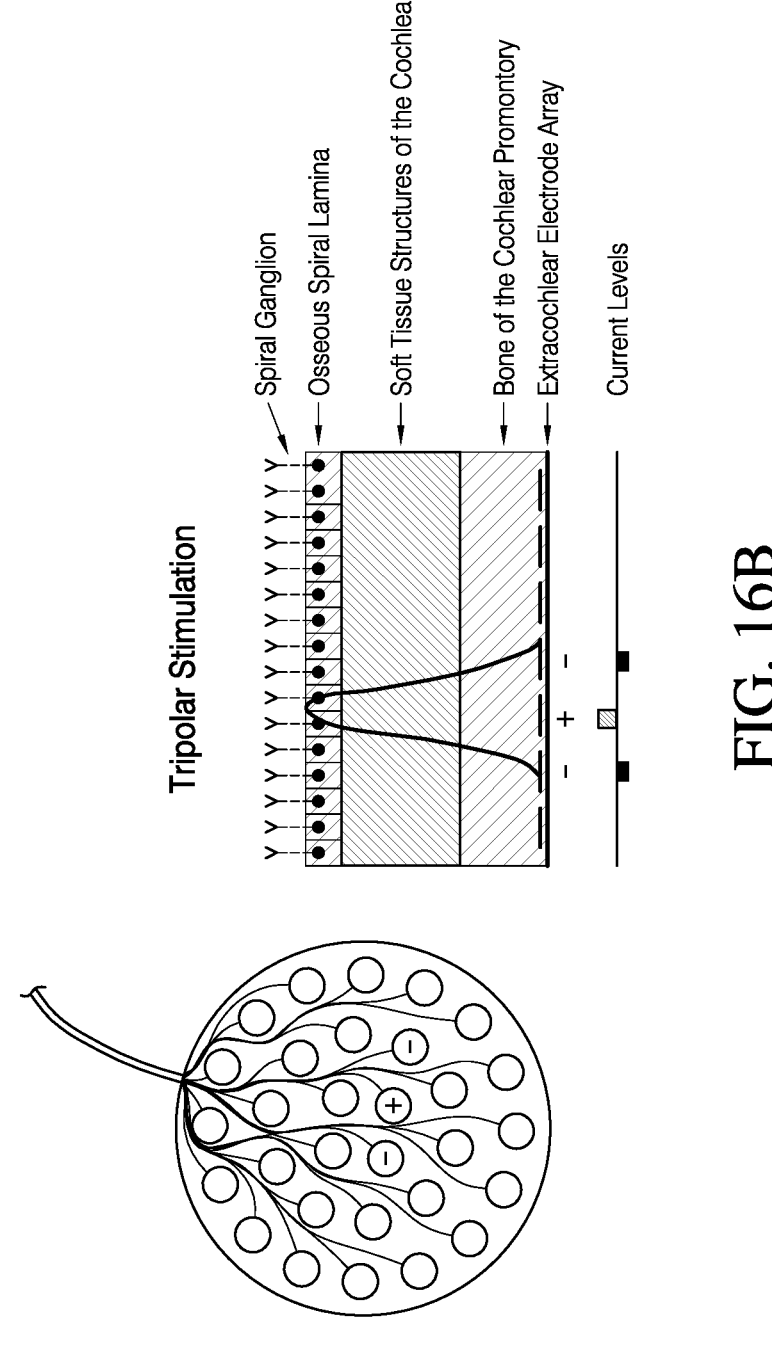
FIG. 16B shows a tripolar stimulation mode of an energy delivery element to optimize for tonotopic stimulation and restoration of hearing outcomes.
Figure 16C:
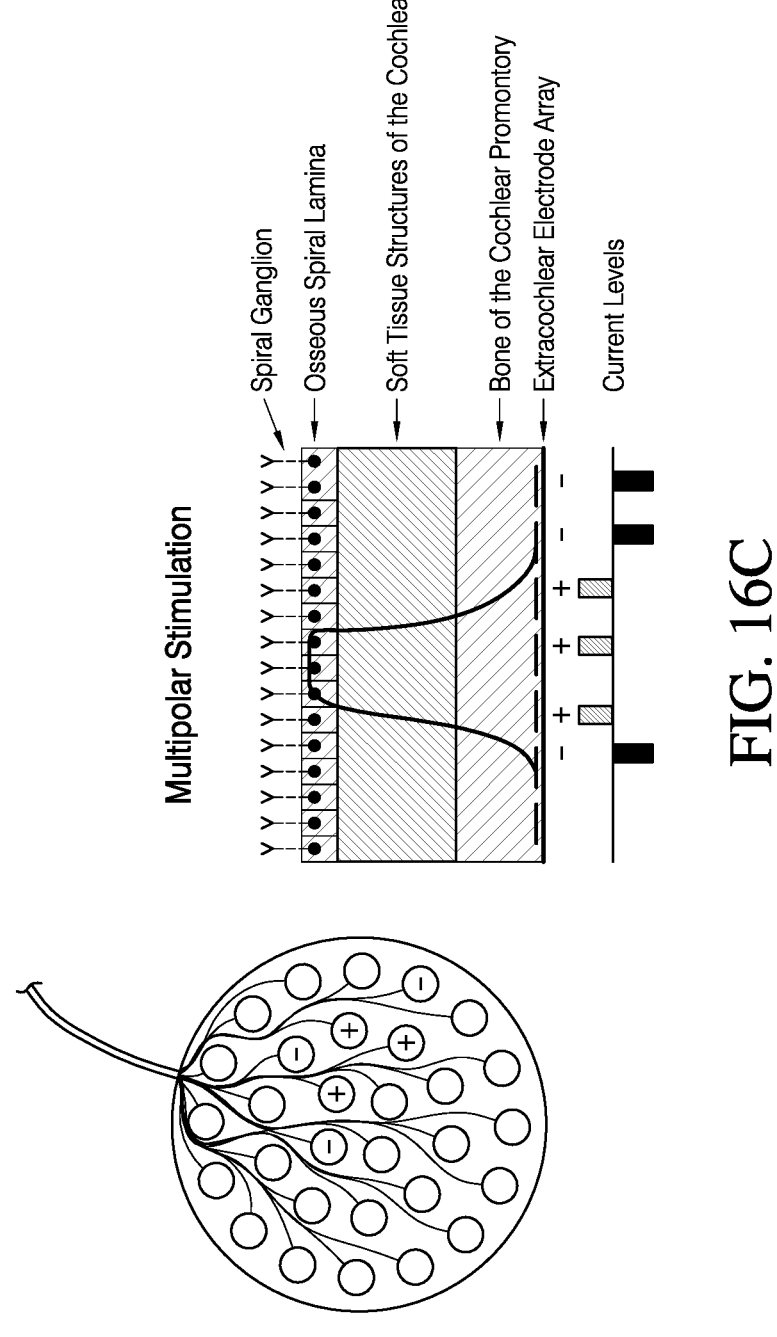
FIG. 16C shows a multipolar stimulation mode of an energy delivery element to optimize for tonotopic stimulation and restoration of hearing outcomes.

In FIGS. 16A-16C, various modes of extracochlear stimulation are depicted with both a view of the front side of an embodiment of an energy delivery element and a corresponding graph showing the strength of current across various tissues of the cochlea in proper anatomical sequence from a secured energy delivery element in contact with the cochlea. As shown in FIG. 16A, in bipolar stimulation, one electrode serves as the anode and another serves as the cathode with balanced charge which provides a narrow peak of current having a longer tail towards the cathode. As shown in FIG. 16B, in tripolar stimulation, there is one anode and two cathodes with negative charge split equally or differentially between the two cathodes which allows for a more even current distribution along the linear dimension of the three electrodes. As shown in FIG. 16C, in multipolar stimulation, a combination of electrodes can be used as cathodes or anodes with varying levels but net balanced charge. These stimulation modes can be used to shape the current spread from the electrode(s) to the target, resulting in selected neuronal activation. The choice of stimulation mode or combination of stimulation modes will be optimized for the desired outcome of hearing improvement or restoration and speech perception.

Figure 17B:
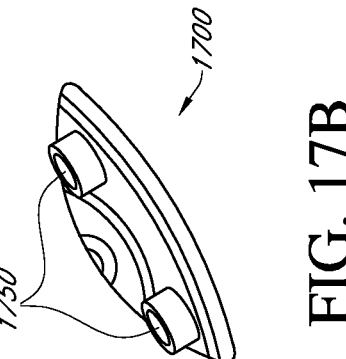
FIG. 17B shows a side view of the energy delivery element of FIG. 17A.
Figure 17A:
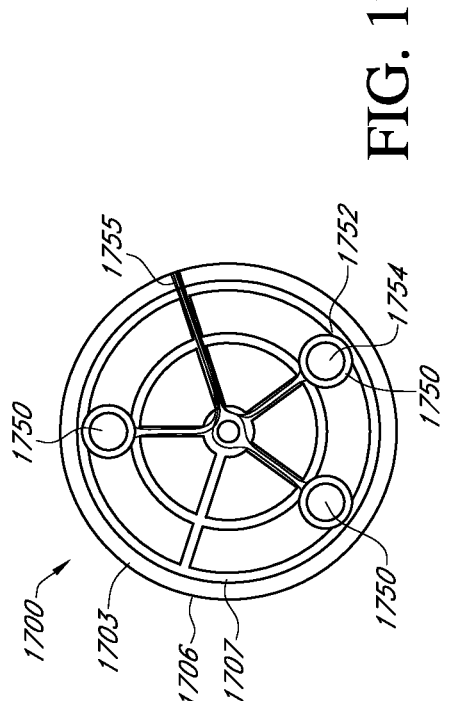
FIG. 17A shows a view of a back side of an energy delivery element configured to magnetically steer current to specific neurons to be activated tonotopically.
Figure 17C:
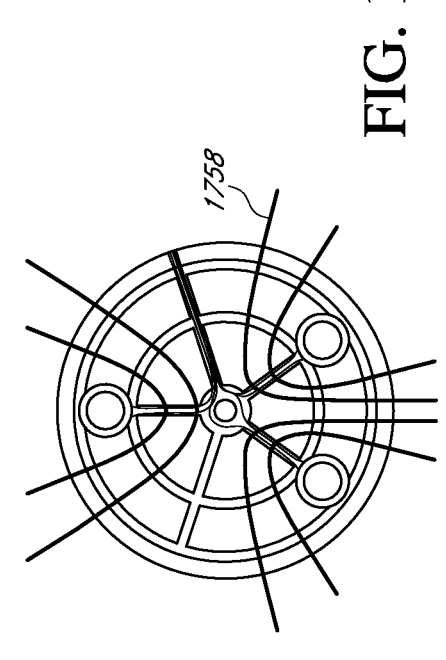
FIG. 17C shows a similar view of the embodiment of FIG. 17A but with a representation of a magnetic field drawn about each electromagnet.

FIGS. 17A-17C depict various views of another embodiment of an energy delivery element 1700 for extracochlear stimulation that employs electromagnets 1750 to steer the applied current to specific portions of the energy delivery element 1700. FIG. 17A shows a view of a back side 1703 (i.e., facing away from a target tissue surface) of the array 1700. Three electromagnets 1750 are spaced radially around the substrate 1706 on the back side 1703. In some embodiments, the electromagnets 1750 can comprise a conductive coil 1752 wound about a ferromagnetic core 1754, and the electromagnets 1750 can be connected to one or more control and/or power supplies by electromagnet leads 1755. FIG. 17B shows a side view of the energy delivery element 1700 showing the relative positions of the electromagnets 1750 with regards to the height and shape of a convex array 1700. FIG. 17C shows a similar view of the embodiment of the energy delivery element 1700 but with a representation of a magnetic field 1758 drawn about each electromagnet 1750. In the embodiment of FIGS. 17A-17C, three electromagnets 1750 are employed, although any number of electromagnets (e.g., one or more) can be employed in alternative embodiments. In further embodiments, the electromagnets 1750 are worn externally on and around the ear where the device is implanted. However, the one or more electromagnets can be independently turned on or off and/or vary in the intensity of their magnetic field simultaneously across many embodiments. The electromagnets 1750 are operated in sync with the delivery of electrical stimulus through the electrodes (not shown) to the cochlea so that the current can be actively steered and/or focused toward specific neurons to be activated for tonotopicity. In the embodiment of FIGS. 17A-17C, the substrate 1706 of the array 1700 is shown as partially transparent for the purposes of illustrating a supporting internal structure 1707, as described herein.

Figure 18B:
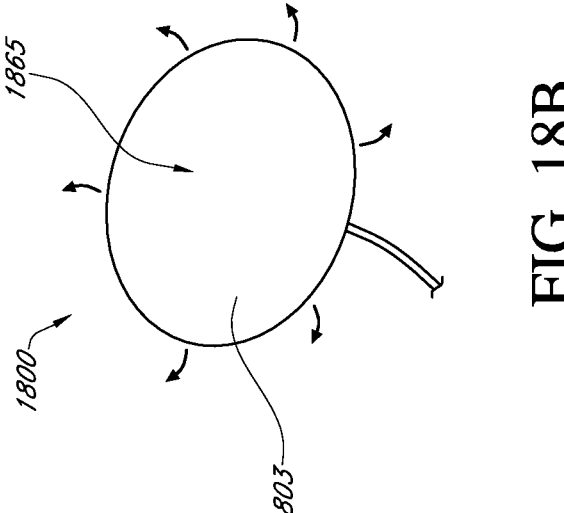
FIG. 18B depicts a pressure force being applied to the energy delivery element of FIG. 18A to secure the element to a cochlea.
Figure 18A:
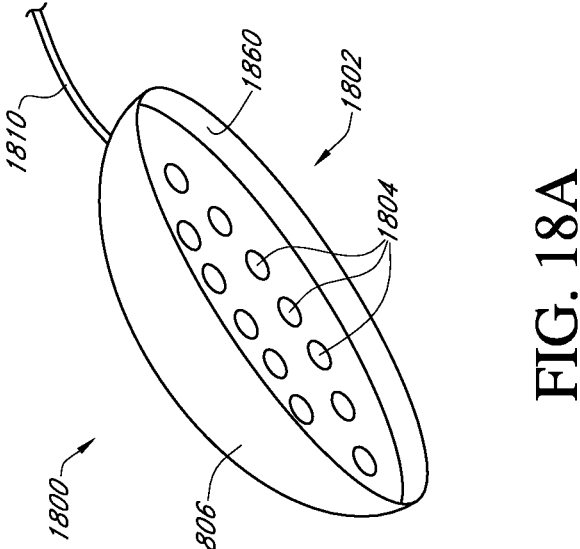
FIG. 18A shows an energy delivery element having a cup-like shape for suctioning to a cochlea surface.

FIGS. 18A and 18B show another embodiment of an energy delivery element 1800 for providing extracochlear stimulation that can utilize a suction force to remain secured to a surface of the cochlea. As show in the perspective view of FIG. 18A, the energy delivery element 1800 comprises a silastic or other flexible, airtight material as a substrate 1806 that is formed into a cup-like shape with a steeper pitch than that of the cochlea, in this embodiment. A plurality of electrodes 1804 can be arranged in a variety of patterns, as described herein, on a front side 1802 (tissue contacting side) of the cup-like shape. In this embodiment, the edge of substrate 1806 of the front side 1802 can feature a bevel or flange 1860 that lines the perimeter of the array 1800 and is adapted to improve the airtight seal of the array 1800 when secured to the cochlea. A lead 1810 can connect the array 1800 to other components of the device, as described herein. FIG. 18B depicts a pressure force 1865 being applied to the back 1803 of the flexible substrate 1806 during an implantation procedure that forces out the air within a volume of the cup-like shaped array 1800 when positioned on the target tissue. In some embodiment, the target tissue (e.g., cochlea) may be prepared, for example to be smoothed and/or to have few or no surface irregularities, as described elsewhere herein. This removal of air creates a pressure differential that can result in the exterior air pressure within the middle ear to stick the energy delivery element 1800 to the cochlea. A variety of tools can be used to apply the pressure 1865 to the substrate 1806, including, but not limited to, a stylet; compress (e.g., comprising gauze, cotton, etc.); an absorbent pad, such as a pledget (e.g., comprising one or more of: polytetrafluoroethylene (PTFE), polypropylene, polyethylene terephthalate, etc.); etc.

Figure 19B:
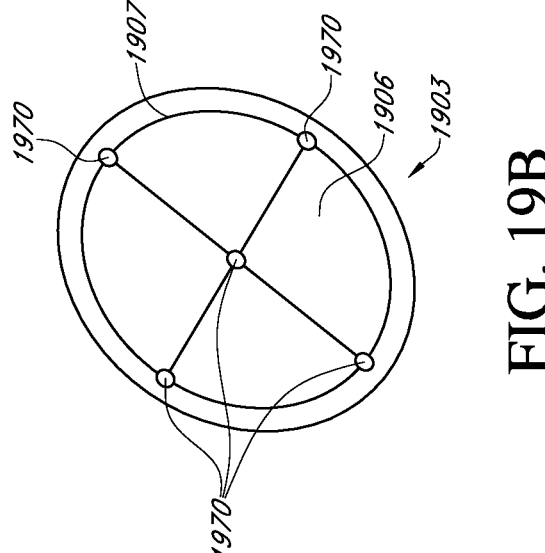
FIG. 19B shows a back view of the energy delivery device of FIG. 19A.
Figure 19A:
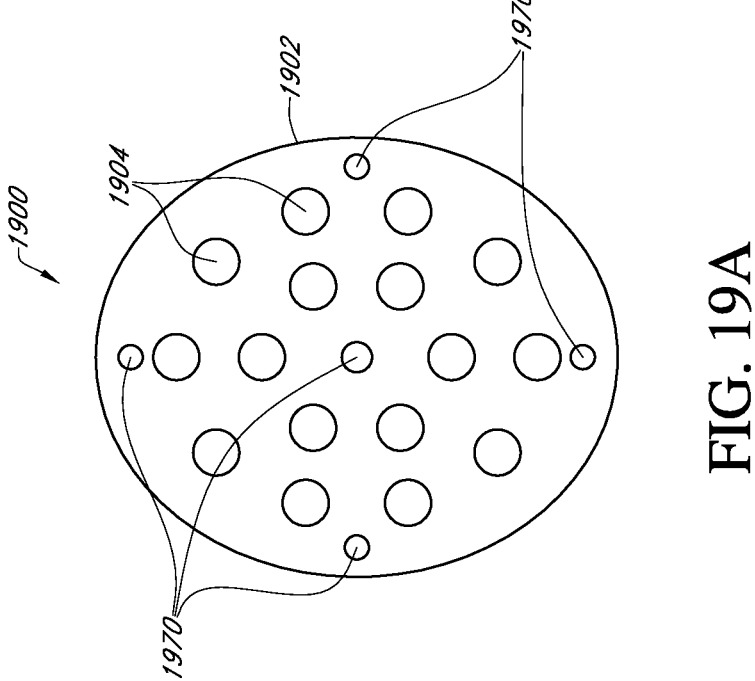
FIG. 19A shows a front view of another embodiment of an energy delivery element attachable to a cochlear promontory using a hydroxyapatite scaffold.

FIGS. 19A and 19B show a front and back view, respectively, of another embodiment of an energy delivery element 1900 for extracochlear stimulation. As shown in FIG. 19A, a front side 1902 (tissue contacting side) of the energy delivery element 1900 may comprise a plurality of exposed electrode heads 1904 arranged in a pattern, as described herein. At one or more locations on the front side 1902, one or more anchoring posts 1970 can be distributed around or on the surface. The anchoring posts 1970 can be coated in a tissue growth factor, such as hydroxyapatite, which promotes bone growth, in order to foster integration of the posts 1970 into the biological surface. FIG. 19B shows a view of a back side 1903 of the array 1900 in which the substrate 1906 is depicted as partially transparent in order to show a supporting internal structure 1907, as described herein. In some embodiments, the anchoring posts 1970 can be secured to the internal structure 1907 for additional structural support.

Figure 20:
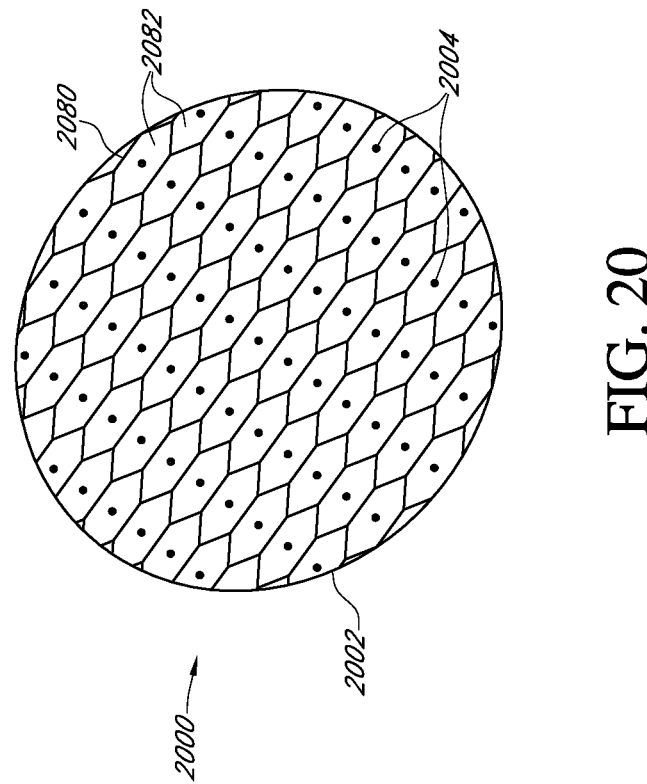
FIG. 20 shows another embodiment of an electrode array having each stimulating electrode surrounding by a return electrode.

FIG. 20 shows a front view of another embodiment of an energy delivery element 2000 for providing extracochlear stimulation that comprises a hexagonal or honeycomb-shaped return electrode 2080 that surrounds each stimulating electrode head 2004 of the electrode array 2000. As described herein, the return electrode 2000, by providing a common ground, can limit the lateral spread (i.e., the spread in the direction of the plane of the front side 2002 of the array 2000 when secured to the cochlea) of the delivered charge of a given stimulating electrode head 2004 to the area of its cell 2082 created by the surrounding return electrode 2080. By constraining the spread of the delivered stimulating charge, the energy delivery element 2000 can more selectively and accurately deliver charge tonotopically to the extracochlear surface than embodiments that allow the charge to travel according to the natural resistance of the biological surface. In various embodiments, the activation or other operations of the return electrode 2080 can be synchronized or coordinated with the one or more stimulating electrode heads 2004. In many embodiments, the return electrode 2080 can be switched on or off.

Figures 21A, 21B, 21C, 21D:
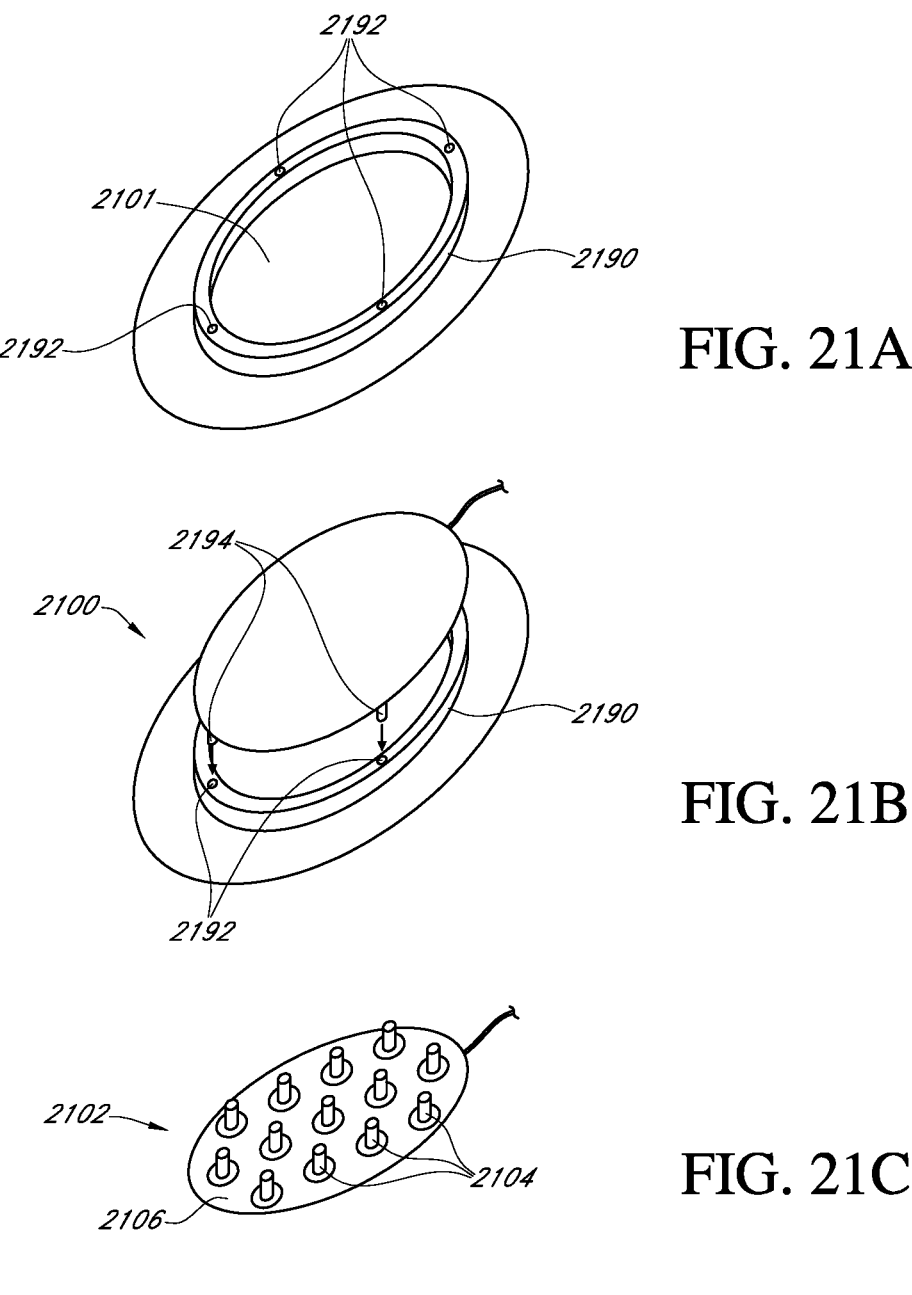
FIG. 21A shows a perspective view of an embodiment of a jig attached to a cochlea.
FIG. 21B shows an embodiment of a substrate being inserted onto the jig of FIG. 21A.
FIG. 21C shows a front side of the substrate of FIG. 21B comprising energy delivery elements comprising electrode contact pogo pins.
FIG. 21D shows a cross-sectional view of the energy delivery elements of FIG. 21C extending to an external surface of a cochlea.

FIGS. 21A-21D show various views of another embodiment of an energy delivery element 2100 during various stages of implantation on a promontory surface 2101. In the embodiment of FIGS. 21A-21D, the energy delivery element 2100 can comprise a detachable frame or jig 2190 that is secured first to the prepared target surface 2101 with adhesive 2199 or with another attachment means, as described herein (e.g., screws). FIG. 21A shows a perspective view of an embodiment of a frame 2190 attached to the cochlea 2101. The frame 2190 is designed to conform to the geometry of the target tissue 2101 and could have a variety of shapes, including, but not limited to: circular, oval, rectangular, square, or irregular. The faces of the frame 2190 that attach to the target surface 2101 can comprise a variety of surface features or textures, such as a bevel, that are adapted to allow the frame 2190 to match the contour of the target surface 2101 and allow for maximum surface area contact. In some embodiments, adhesive 2199 could be applied to the frame 2190 during manufacturing and sealed with a film coating removed just prior to insertion or adhesive could be applied outside of the body just prior to insertion. In other embodiments, the energy delivery element may be manufactured with a film coating that is configured to be removed just prior to application of the array on the external surface of the cochlea. In many embodiments, the frame 2190 further comprises one or more connectors 2192 that allow for the subsequent attachment of the substrate 2106 of the array 2100 that feature the electrode heads 2104. In the embodiment of FIGS. 21A-21D, the connectors 2192 comprise one or more holes positioned on the exposed surface of the frame 2190 that receive and lock with pins 2194 that extend from the substrate 2106. In some embodiments, the pins 2194 can be barbed or a mechanical locking and release mechanism can otherwise be present on one or both of: the substrate 2106 or frame 2190 to ensure the substrate 2106 is securely attached to the frame 2190. FIG. 21B shows an embodiment of the substrate 2106 being inserted onto the frame 2190. FIG. 21C shows a front side 2102 of an embodiment of the substrate that comprises electrode contact pogo pins 2104, such as ones similar to those of FIGS. 10A-10C. As shown in the cross-sectional view of FIG. 21D, the electrode contact pogo pins 2104 are configured to extend down to reach the external surface 2101 of the target surface to maintain good electrical contact despite the height of the frame 2190.

Figures 22A, 22B:
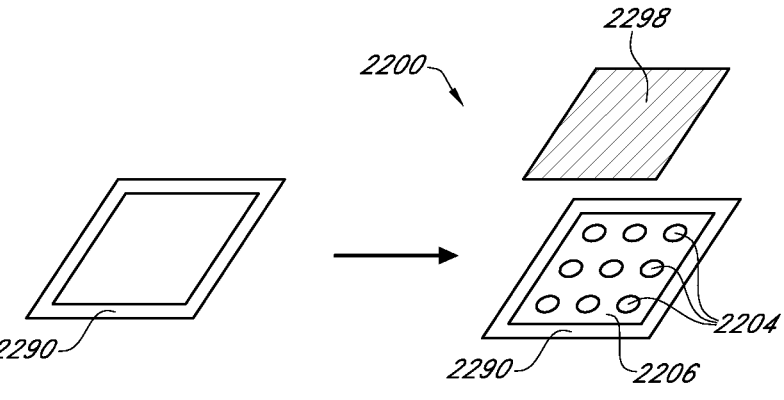
FIGS. 22A-22B show another method, and associated array, for positioning the energy delivery element on a frame attached to a cochlear promontory. The frame is shown in FIG. 22A and the energy delivery element is shown attached to the frame in FIG. 22B.

FIGS. 22A and 22B show an alternative embodiment wherein the jig or frame 2290 of energy delivery element 2200 is first secured to the cochlear surface (e.g., with adhesive or screws), and subsequently, the substrate 2206 comprising the exposed electrode heads 2204 can then be placed inside the frame 2290. FIG. 22A shows the frame 2290 attached without the inserted substrate 2206; FIG. 22B shows the substrate 2206 (shown with partial transparency to depict the electrode heads 2204) inserted inside the frame 2290. In many embodiments, the substrate 2206 is adapted to have a geometry that fits tightly against the walls of the frame 2290 so as to prevent or limit lateral movement of the substrate 2206 within the frame. In the embodiment of FIGS. 22A and 22B, the frame 2290 and substrate 2206 are shown with a square or rectangular shape although other shapes can be employed without departing from the scope of the invention, as described herein. In some embodiments, a cap 2298 can be secured on top of the frame 2290 over the substrate 2206 in order to prevent the substrate from falling out or moving within the frame 2290. In some embodiments, the cap 2298 is adapted to push-fit inside a receiving mechanism of the frame 2290. In other embodiments, the cap 2290 can be secured with an adhesive or other mechanism (e.g., screws).

Figures 23A, 23B:
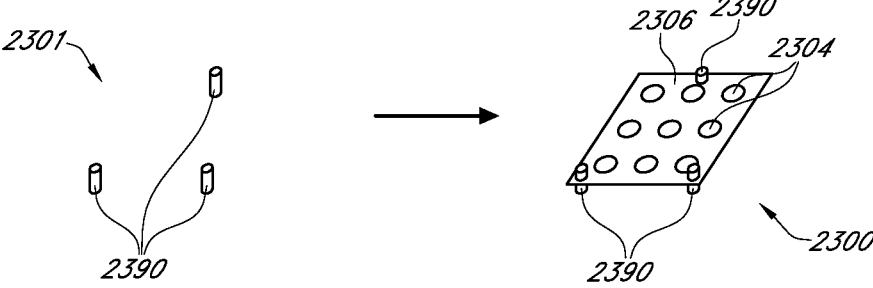
FIGS. 23A-23B show another method, and associated array, for positioning the energy delivery element on one or more posts coupled to a cochlear promontory.

FIGS. 23A and 23B show another alternative embodiment for an energy delivery element 2300 for extracochlear stimulation. In this embodiment, one or more supporting pegs or posts 2390 can be secured first to the cochlea 2301. Subsequently, a substrate 2304 comprising exposed electrode heads 2306 can be secured to the posts 2390. FIG. 23A shows the supporting posts 2390 secured to the cochlea 2301 without the substrate 2306; and FIG. 23B shows the subsequent attachment of the substrate 2304. In various embodiments, the supporting posts 2390 can be secured to the cochlea 2301 by adhesive or screws, although other attachment mechanisms can be used. In some embodiments, the substrate 2306 is adapted to couple to the supporting posts 2390 by push-fit mechanical mechanisms. In other embodiments, the substrate 2306 can be secured to the supporting posts 2390 by adhesive, glue, or another mechanism. In FIG. 23B, the substrate 2306 is shown as partially transparent in order to depict the electrode heads 2304.

Figure 24A:
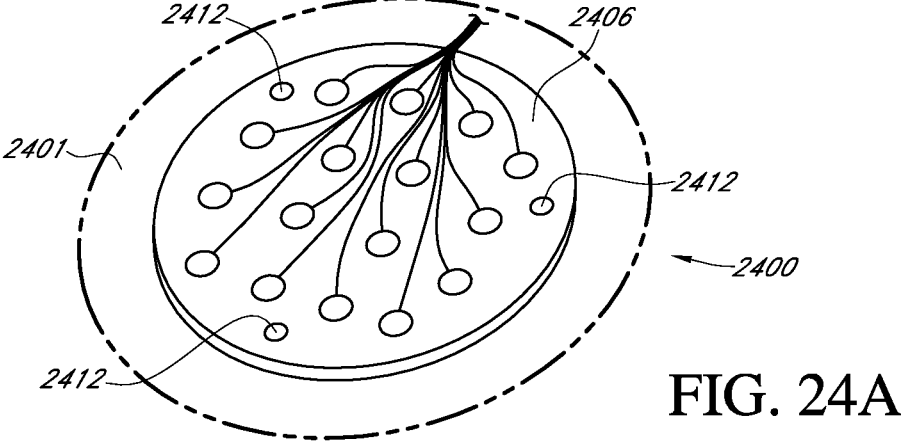
FIGS. 24A-24B show another method, and associated array, for adhesively attaching the energy delivery element to a cochlear promontory.
Figure 24B:
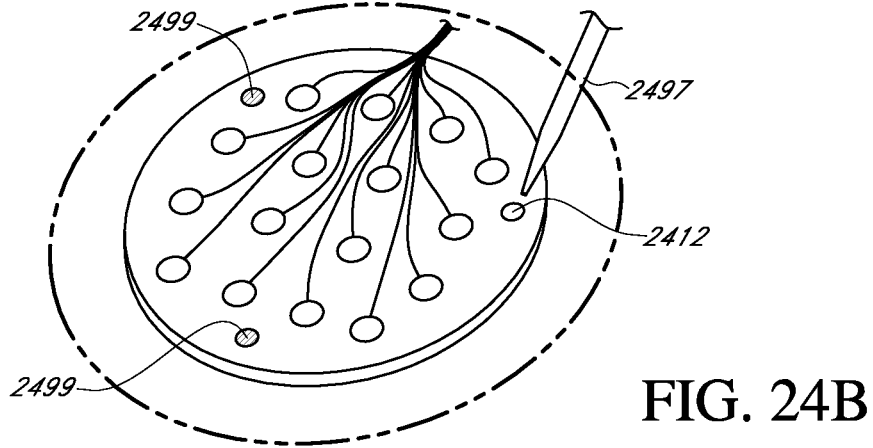

FIGS. 24A-24B depict steps for a method for implanting an embodiment of an electrode array 2400 on an external surface 2401 of a cochlea. the surface of the cochlea 2401 is first prepared (using any of the method described elsewhere herein) to maximize subsequent adhesion of the array 2400. The preparation can comprise any one or more of: cleaning, acid treatment, drying, roughening, cutting operations, as well as any others as described elsewhere herein. For example, the preparation can include roughening of the surface, removal of overlying mucosa, and/or removal of any irregularities. Once the surface is prepared, the energy delivery element 2400 is then positioned tightly against the cochlea 2401 such that no air should be present between the energy delivery element 2400 and the cochlea 2401. In the embodiment of FIGS. 24A-24B, the energy delivery element 2400 comprises adhesive wells 2412 which can be channels or shafts that traverse the thickness of the substrate 2406 of the array 2400. In FIGS. 24A and 24B, the array 2400 is shown as partially transparent in order to illustrate various details. In FIG. 24B, the array 2400 is then secured to the cochlea 2401 by filling the adhesive wells 2412 with adhesive 2499, for example, cyanoacrylate, with an adhesive applicator 2497. Although three adhesive wells 2412 are shown in a radial arrangement near the edge of the substrate 2406 in the embodiment of FIGS. 24A-24B, any number of adhesive wells 2412 in various arrangements can be used in other embodiments without deviating from the scope of this disclosure.

Figure 25A:
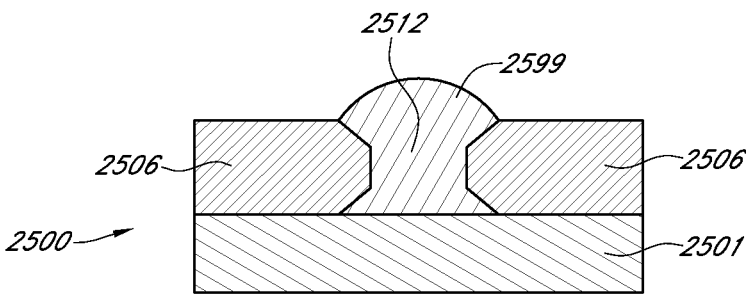
FIG. 25A shows a zoomed-in view of an attachment point between an energy delivery element and a surface of a cochlear promontory.
Figure 25B:
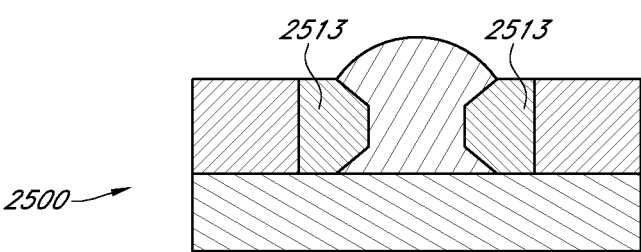
FIG. 25B show a zoomed-in view of another attachment point between an energy delivery element and a surface of a cochlear promontory.
Figure 25C:
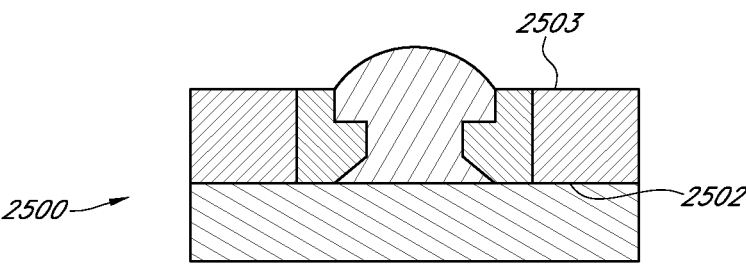
FIG. 25C show a zoomed-in view of another attachment point between energy delivery element and a surface of a cochlear promontory.

FIGS. 25A-25C show a cross-sectional view of embodiments of adhesive wells 2512 (such as those of FIGS. 24A-24B) of an energy delivery element 2500. FIG. 25A shows the profile of an adhesive well 2512 in a substrate 2506 having been filled with adhesive 2599 to attach the substrate 2506 to the external surface 2501 of the cochlea. FIG. 25B shows the same adhesive well 2512 but highlights the trapezoidal shape 2513 of the cross-section of the wall of the adhesive well 2512. By having a bevel or funnel shape on both the front 2502 and back sides 2503 of the substrate 2506, there is a greater surface area for which adhesive to adhere, thus strengthening the connection between the array 2500 and the external surface 2501 of the cochlea. FIG. 25C shows an alternative embodiment of an adhesive well 2512 wherein the bevel of the front side 2502 has a different shape from the bevel of the back side 2503 of the substrate 2506 to further augment the strength of the connection. For example, a diameter of the bevel of the front side 2502 may be greater than, less than, or equal to a diameter of the bevel of the back side 2503.

Figure 26A:
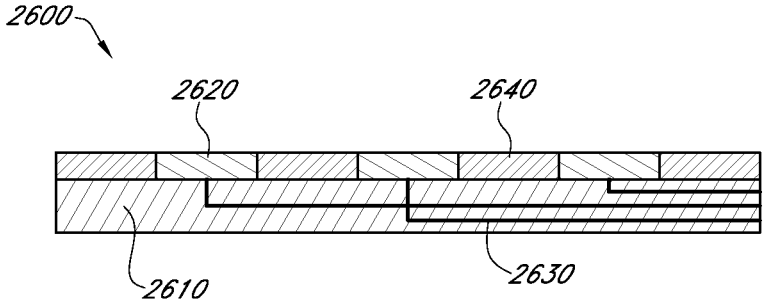
FIG. 26A shows another method, and associated array, for adhesively attaching the energy delivery element to a cochlear promontory, the energy delivery element shown in an unadhered state.
Figure 26B:
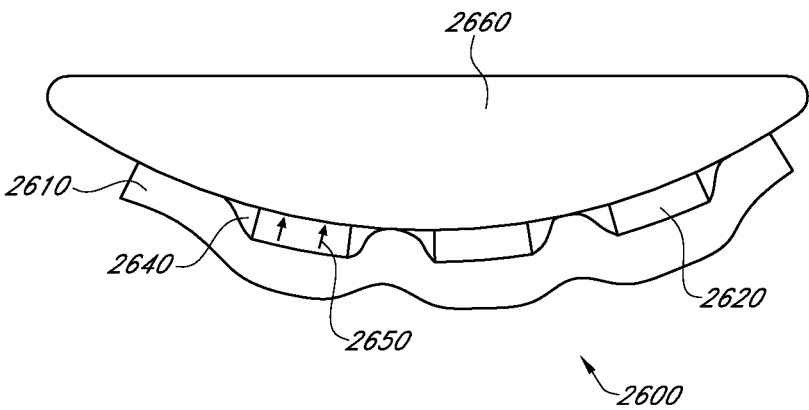
FIG. 26B shows the energy delivery element of FIG. 26A in an adhered state.

FIGS. 26A-26B show an energy delivery element in an unadhered state and an adhered state, respectively. As shown in FIG. 26A, the energy delivery element 2600 comprises a substrate 2610 and one or more electrodes 2620 disposed in or on the substrate 2610. The substrate 2610 includes the electrical contacts 2630 therein for each electrode or sets of electrodes. The substrate may be formed of or comprise: polymeric silicone, silicone elastomer, polyurethane, siloxane copolymers, or combinations, variations, or suitable substitutes thereof. In between one or more electrodes 2620, there may be grooves, microchannels, perforations, or otherwise adhesive deposits, as shown in FIG. 26A. Such grooves, microchannels, perforations, or otherwise adhesive deposits may be continuous throughout the array or may have distinct sections or lengths. Over time, the adhesive deposits 2640 dry and then shrink or contract, as shown in FIG. 26B, resulting in increased pressure, as shown by arrows 2650, of the energy delivery element 2600 against an external surface of the cochlea 2660, for example a promontory of the cochlea. For example, the adhesive compound may be specially formulated to shrink as it cures, bringing the substrate 2610 between electrodes 2620 closer to the promontory surface 2660. The increased downward pressure of the electrode on the promontory surface, as the adhesive cures, is configured to increase conductive properties of the electrodes and correct for any imperfections in the surface or inconsistencies in the application of the array during implantation.

FIGS. 27A-27D show various views of an alternative energy delivery element 2700. As shown in FIGS. 27A-27D, the substrate 2710 of the energy delivery element 2700 comprises a conformable wire, for example formed of or comprising polymeric silicone, silicone elastomer, polyurethane, siloxane copolymers, or combinations, variations, or suitable substitutes thereof. The electrodes 2720 are attached to the substrate 2710 and electrically connected therethrough, for example there may be electrical contacts 2722 to each electrode or to sets of electrodes. The electrodes 2720 of the energy delivery element 2700 may be substantially circumferential or semi-circular to allow for electrical contact in any orientation or only on one side of the coil, respectively. The energy delivery element may have a substantially linear delivery configuration, as shown in FIG. 27D, such that the array can be introduced and withdrawn through a catheter 2730 or through a blind orifice. Once deployed, the energy delivery element 2700 assumes a second deployed configuration having a coil-like configuration, as shown in FIG. 27A. The deployed configuration conforms or is configured to conform to an external surface 2740 of the cochlea, for example a promontory of the cochlea, as shown in FIG. 27C. The energy delivery element 2700 may be electrically connected via lead 2724 to the receiver/stimulator, either locally or positioned external to the middle ear cavity. In some embodiments, one or more portions of the array are at least partially encased in a casing. The casing may be inert and/or conductive. In some embodiments, once the array is positioned on an external surface of the cochlea, it may be secured temporarily, semi-permanently, or permanently with bioabsorbable packing or adhered with cyanoacrylate or a one-sided sheet of adhesive, for example. In one embodiment, the electrode array, as shown and described in FIGS. 27A-27D, may be used for acute testing (e.g., to determine ideal array placement, to determine degree of hearing deficiency, etc.), such that it could be withdrawn through a tympanostomy tube or in a submucosal plane along the ear canal without requiring the patient to undergo another surgery.

Figure 29A:
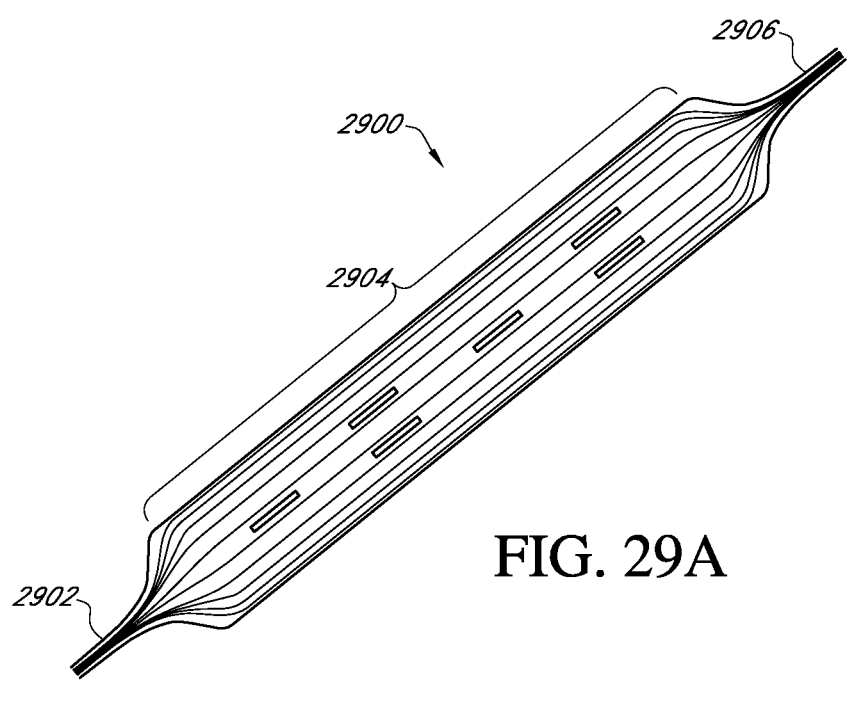
FIG. 29A shows a top view of a cable that is configured to connect an extracochlear electrode array to a stimulator/receiver.
Figure 29B:
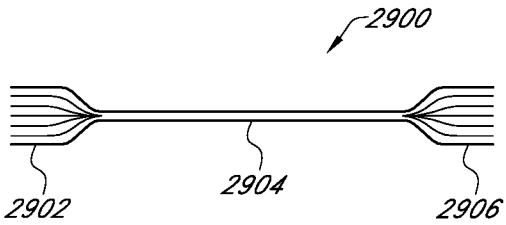
FIG. 29B shows a side view of the cable of FIG. 29A.
Figure 29C:
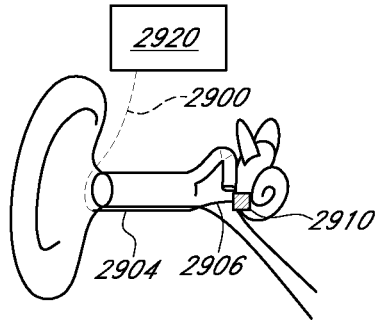
FIG. 29C shows an implanted view of the cable of FIG. 29A.

FIGS. 29A-29C show various views of one embodiment of a cable or lead 2900 that electrically connects an energy delivery element 2910 positioned in the middle ear cavity to a stimulator/receiver 2920 positioned, for example, externally and/or post auricularly, as shown in FIG. 29C (similar to the delivery method of FIGS. 6-7). As shown best in FIGS. 29A-29B, the lead 2900 transitions from a first section 2902 to an intermediate section 2904 to a second section 2906. In some embodiments, first section 2902 may be substantially cylindrical. In some embodiments, the intermediate section 2904 may be substantially planar or have a flat ribbon configuration. In some embodiments, the second section 2906 may be substantially cylindrical. Alternatively, depending on the desired configuration, patient anatomy, delivery method, etc. any one or more of: the first, intermediate, or second section may be substantially cylindrical or substantially planar. Optionally, in some variations, any of the sections, for example the intermediate section may define one or more perforations 2908 to enable, for example, tissue ingrowth, adhesion, or soft tissue bridge formation from either side of the ribbon over time, avoiding the issue of tissue dehiscence. The benefit of a substantially ribbon-like configuration of the intermediate section would be for implantation along the ear canal where typically implanting a cylindrical cable along the length of the canal results in extrusion. The substantially ribbon-like configuration enables the cable to lie flat along an arc of the canal or to conform to the ear canal. Although described in connection with the ear canal, one of skill in the art will appreciate that the cable design shown and described in FIGS. 29A-29C may be employed with any of the energy delivery elements described elsewhere herein.

Figure 30:
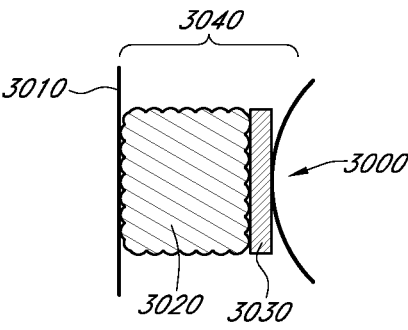
FIG. 30 shows an embodiment of a device that is configured to expand and apply pressure to an electrode array against a cochlear promontory.
Figure 31:
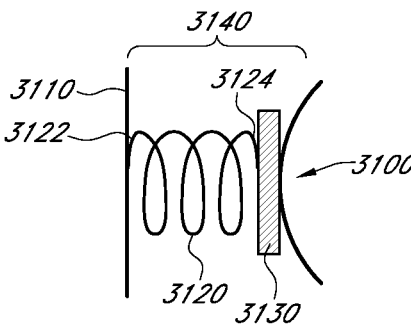
FIG. 31 shows an embodiment of a spring-based device that is configured to apply pressure to an electrode array against a cochlear promontory.
Figure 32:
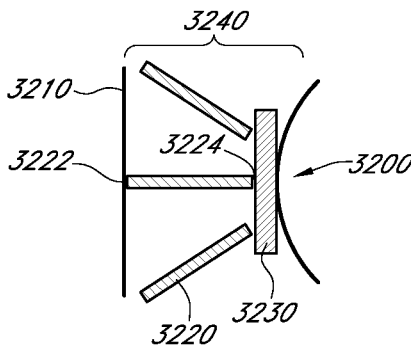
FIG. 32 shows an embodiment of a device comprising one or more posts that are configured to apply pressure to an energy delivery element against a cochlear promontory.

For any of the energy delivery element embodiments described herein, the energy delivery element may maintain contact with an external surface of the cochlea via a pressure-based mechanism, as shown in FIGS. 30-32. The pressure-based mechanisms described herein may be temporary or permanent or long-term. In temporary embodiments, the pressure is applied until the energy delivery element is attached to an external surface of the cochlea, for example via mechanical fixation, tissue ingrowth, or the like. After such attachment, the pressure is relieved/removed. In permanent or long-term embodiments, the pressure is applied as a means of securing the energy delivery element to an external surface of the cochlea, such that mechanical fixation of the electrode array to an external surface of the cochlea is unneeded or at least optional. In any of these embodiments, an external surface of the cochlea may be unmodified or minimally modified, for example by acid treatment, tissue growth factor treatment, adhesive application, mucosa disruption, drying the external surface of the cochlea, selectively drilling the cochlea to increase impedance at targeted locations, etc.

Turning now to FIG. 30 which shows a scaffold or deformable material 3020, for example a deformable polymer, sponge (e.g., gelatin), fibrin glue, hydrogel, or balloon. Consistent with either temporary or long-term use, the deformable material may, in some embodiments, be biodegradable. The deformable material 3020, during insertion, has a first unexpanded configuration and once positioned in the middle ear cavity 3040, a second expanded configuration. The deformable material is configured to be positioned in the middle ear cavity 3040 between a wall 3010 of the middle ear cavity and the energy delivery element 3030, such that the deformable material 3020, in an expanded configuration, applies pressure to the energy delivery element 3030 against an external surface of the cochlea 3000 to enable electrical stimulation of the neurons in the cochlea 3000. In some embodiments, the deformable material 3020 may expand to substantially fill the middle ear cavity 3040.

In another embodiment, as shown in FIG. 31, one or more springs 3120 are positioned in the middle ear cavity 3140 to apply pressure to the energy delivery element 3130 against an external surface of the cochlea 3100 to enable electrical stimulation of the neurons of the cochlea 3100. The spring

3120 may be positioned such that a first end or portion 3122 of the spring 3120 contacts a wall 3110 of the middle ear cavity 3140 and a second end or portion 3124 of the spring 3120 contacts the energy delivery element 3130. The spring 3120 may be delivered to the middle ear cavity 3140 in an uncompressed or elongated configuration and then it may assume a compressed configuration when positioned between a wall 3110 of the middle ear cavity 3140 and the energy delivery element 3130.

In another embodiment, as shown in FIG. 32, one or more elongate pillars 3220 may positioned in the middle ear cavity 3240 to apply pressure to the energy delivery element 3230 against an external surface of the cochlea 3200 to enable electrical stimulation of the neurons of the cochlea 3200. The one or more elongate pillars 3220 may be positioned such that a first end or portion 3222 contacts a wall 3210 of the middle ear cavity 3240 and a second end or portion 3224 contacts the energy delivery element 3230. The first and second ends may be atraumatic and/or unmodified in some embodiments; in other embodiments, the first end 3222 may comprise a barb or anchor such that is at least partially penetrates the wall 3210 of the middle ear cavity. In some embodiments, the second end 3224 includes features (e.g., hooks, fasteners, magnets, etc.) that enable the second end 3224 to couple to the energy delivery element, thereby securing the pillar to the energy delivery element. In some embodiments, the pillars 3220 may be coupled to one another at their first ends 3222 or second ends 3224 via a hub such that the pillars 3220 are collapsible about the hub, for example for delivery, and expandable once inside the middle ear cavity 3240.

Figure 28A:
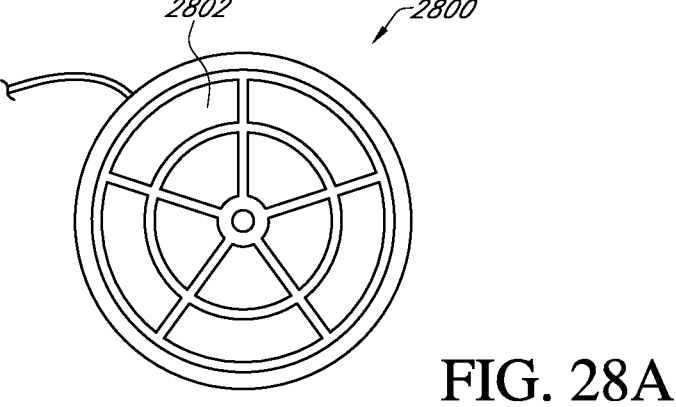
FIG. 28A shows a bottom view (cochlea contact side) of an energy delivery element that includes one or more elongate pillars to apply pressure to the energy delivery element.
Figure 28B:
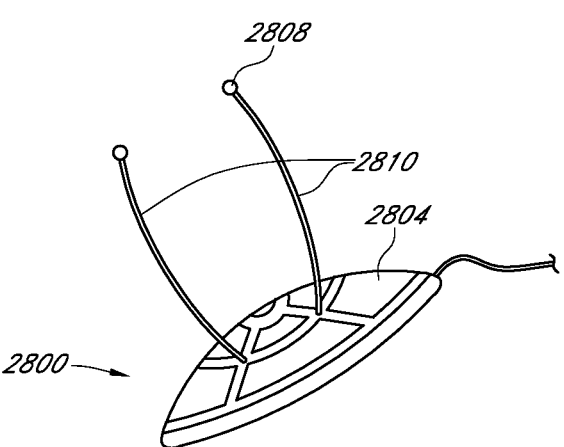
FIG. 28B shows a top view of the element of FIG. 28A, showing the one or more elongate pillars.

FIGS. 28A-28B show another embodiment of one or more elongate pillars 2810 to apply pressure to an energy delivery element 2800 to ensure electrical contact between the electrodes and an external surface of the cochlea. In this embodiment, the pillars 2810 may be semi-rigid, for example formed of or comprising a shape memory alloy, for example, Nitinol, Stainless Steel, or similar material. The one or more pillars 2810 may be secured to a first side 2804 of the energy delivery element 2800 opposite a second side 2802 that is in contact with the cochlear surface. Optionally, the one or more pillars 2810 may further include one or more projections that are configured to push against one or more walls of the middle ear cavity, securing the array and applying counter-pressure to ensure electrical contact of the electrodes with the cochlear surface. One or more free ends 2808 of the pillars 2810 may either be atraumatic, for example comprising feet, or barbed to anchor into a tissue or bone structure of the middle ear cavity.

Figure 33A:
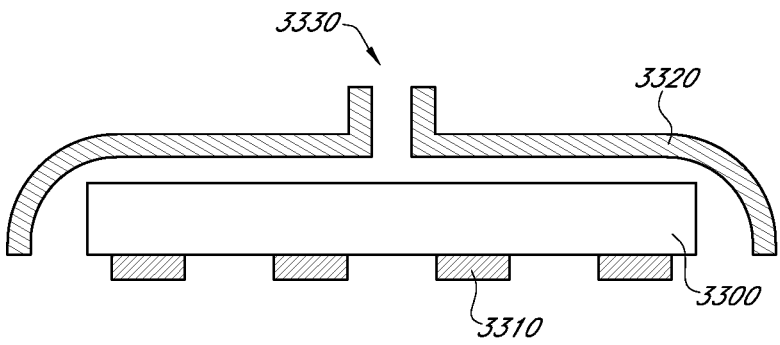
FIGS. 33A-33C show various embodiments of a housing configured to maintain an adhesive at least partially around or on an energy delivery element for adhering the energy delivery element to an external surface of the cochlea.
Figure 33B:
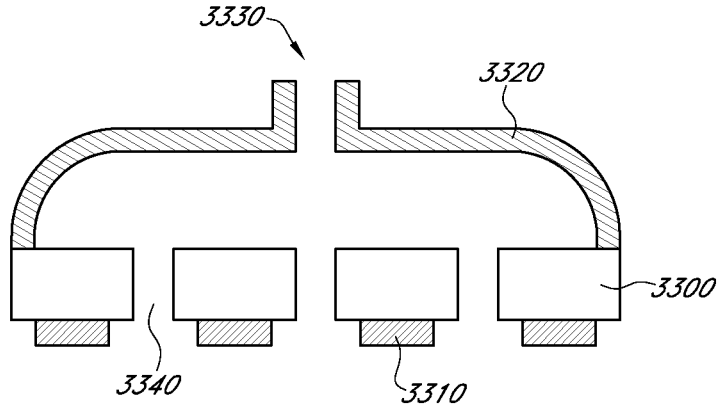
Figure 33C:
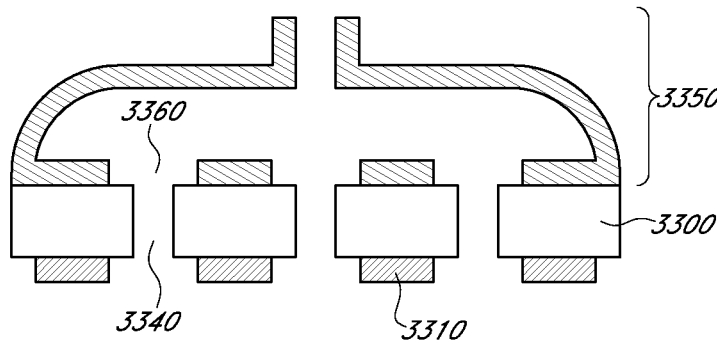

FIGS. 33A-33C show various embodiments of a housing configured to maintain an adhesive at least partially around or on an energy delivery element for adhering the energy delivery element to an external surface of the cochlea. As used herein, a bony surface may comprise or include the promontory bone or a mucosa overlying the promontory bone. As shown in FIG. 33A, housing 3320 at least partially covers or encloses an energy delivery element having substrate 3300 comprising one or more electrodes 3310 integrated into or on the substrate 3300. Housing 3320 defines an injection port 3330 through which adhesive is introduced to adhere the energy delivery element to an external surface of the cochlea. The housing 3320 is configured to be positioned at least partially over or around the substrate and retain an adhesive that is injected through the injection port 3330 to adhere the substrate to the bony surface. In some embodiments, as shown in FIG. 33B, the substrate defines apertures, microchannels, etc. 3340 through which adhesive flows and adheres to the bony surface, for example a promontory of the cochlea, to further secure the array to the bony surface. Still further, in some embodiments, as shown in FIG. 33C, the adhesive is contained in a packet 3350, for example a blister packet, such that disruption of the packet 3350 causes apertures 3360 to be formed in the packet 3350 which release adhesive through one or more apertures 3340 defined by the substrate to contact the bony surface and adhere the array to the bony surface.

Figures 34A, 34B, 34C:
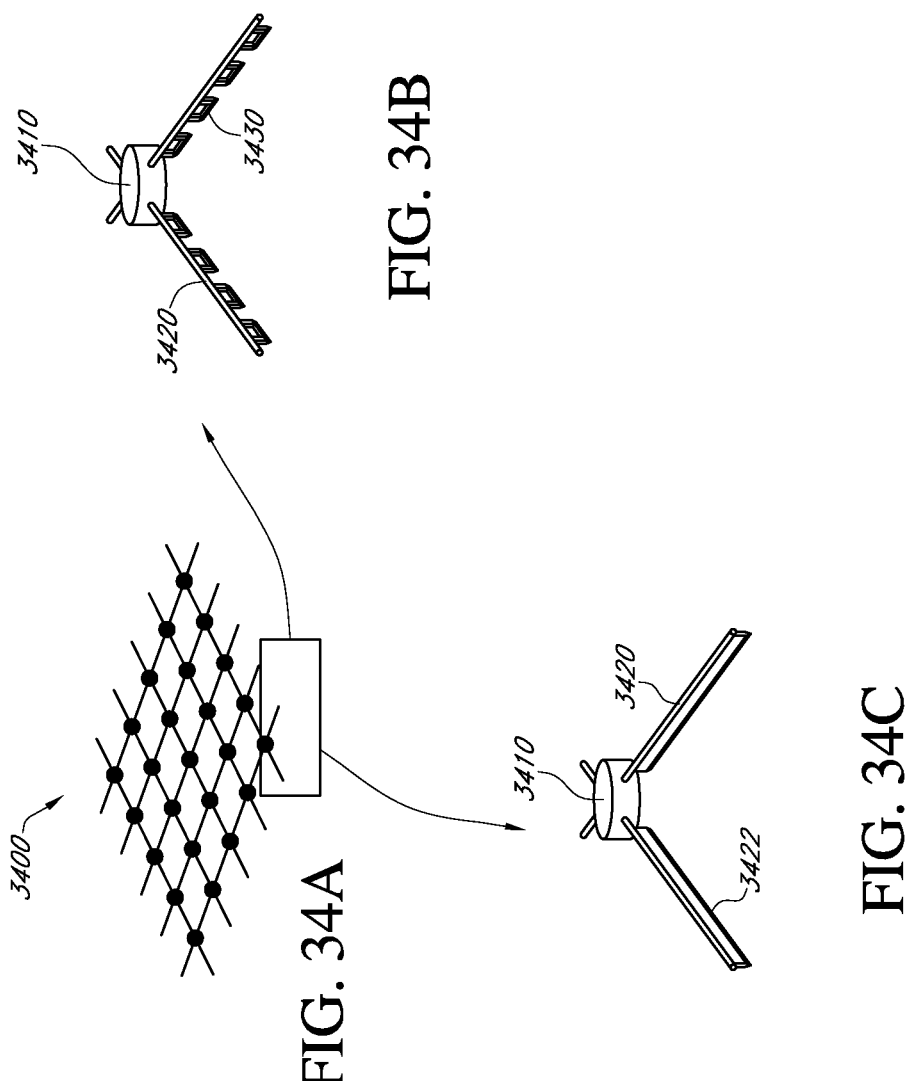
FIGS. 34A-34C show various embodiments of a substrate comprising one or more sharp features for promoting tissue integration with the external surface of the cochlea.

FIGS. 34A-34C show various embodiments of a substrate comprising one or more sharp features for promoting tissue integration with the external surface of the cochlea. Energy delivery element 3400 of FIG. 34A, shown in a zoomed in view in FIGS. 34B-34C includes electrodes 3410 disposed in or on substrate 3420. One or more edges or perimeters of substrate 3420 comprise a tissue penetrating element 3422 (e.g., barbed edge, sharp edge, etc.) to couple the array to the surface and promote tissue growth at the site of penetration, as shown in FIG. 34A. Alternatively, or additionally, substrate 3420 defines one or more apertures 3430 such that tissue may grow through the apertures 3430 to couple the array to the surface. The substrate 3420, tissue penetrating elements, and/or apertures may be optionally coated in a tissue growth promoting factor to promote tissue integration into the energy delivery element.

In some embodiments, a portion of a perimeter of the substrate defines one or more perforations or apertures to promote tissue ingrowth. As used herein, perimeter may be defined as the exterior edge that is perpendicular to or parallel with the surface of the substrate that has the greatest surface area or the exterior edge of the surface of the substrate that has the greatest surface area.

Figure 35:
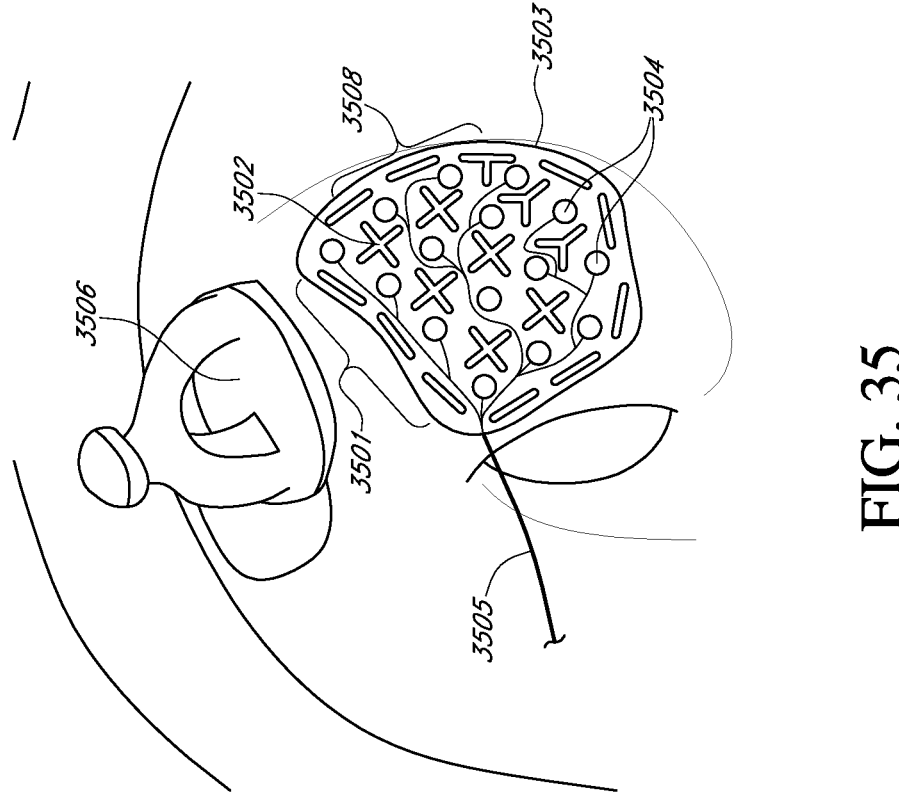
FIG. 35 shows an embodiment of an energy delivery element that is shaped to conform to the anatomical constraints of the middle ear cavity and the promontory.

FIG. 35 shows an embodiment of an energy delivery element that is shaped to conform to the anatomical constraints of the middle ear cavity and the promontory. Such shaping may include a curved or concave portion or section 3501 in the substrate of the array to avoid contacting the stapes footplate 3506 and round window membrane. In some embodiments, this shaping may further function as a self-locating feature to allow for correct orientation and initial positioning of the energy delivery element in the middle ear surface. As shown in FIG. 35, the substrate of the array defines perforations 3502 distributed across a center region 3508 and/or along at least a portion of a perimeter 3503 of the electrode substrate. Such perforation distribution allows for adhesive to be applied to a top side of the array, passing through the perforations, and anchoring the substrate to the middle ear surface below. These perforations also enable the electrode substrate to conform more readily to the curved contour of the middle ear surface. Perforations may also allow tissue growth through the electrode substrate, a form of body mediated adhesion. The plurality of electrodes 3504 distributed across the substrate are connected to an implanted stimulator through a lead 3505 that exits from the energy delivery element at a trajectory allowing for easy connection to the implanted stimulator. Such positioning functions to avoid contact with any important anatomical structures such as the ossicles of hearing and minimizes tension on the body of the electrode array.

Figure 36:
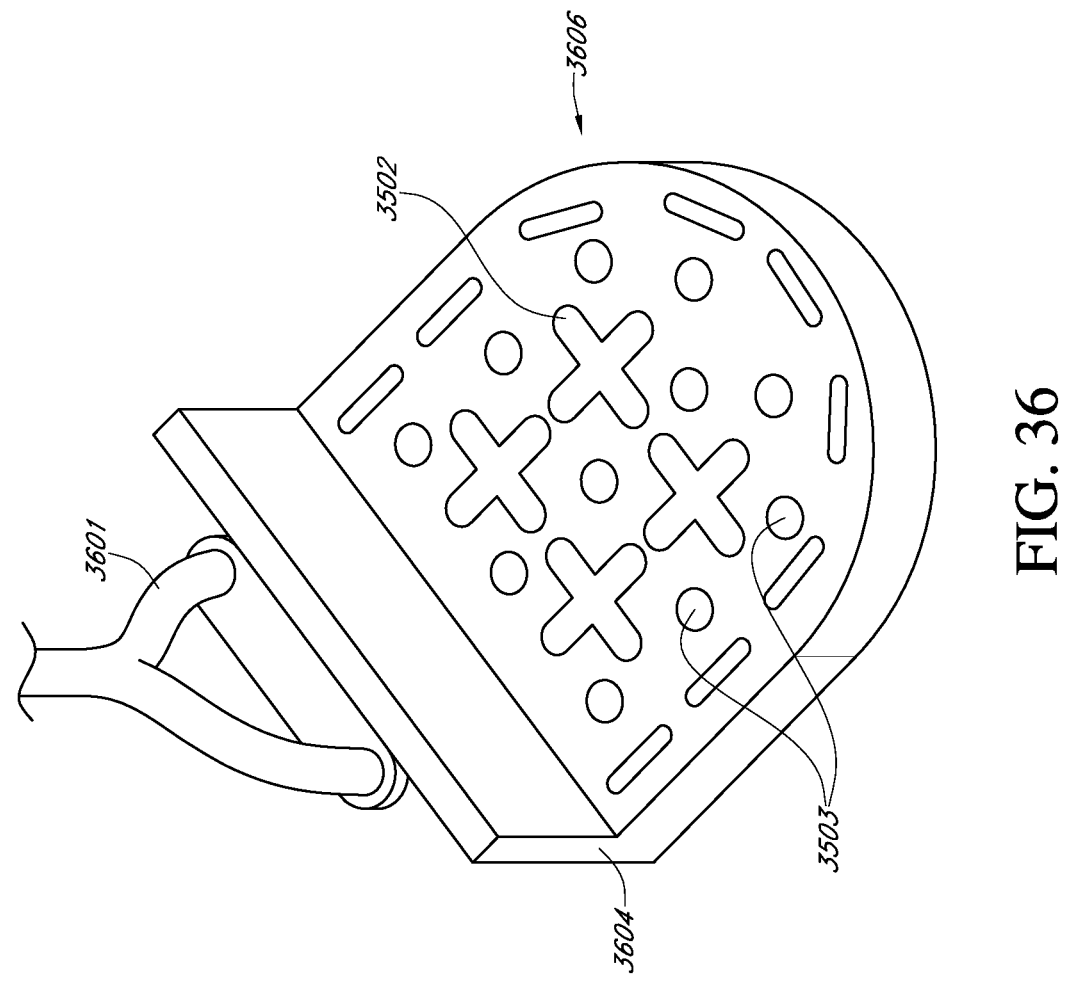
FIG. 36 shows an embodiment of an energy delivery element that comprises a raised perimeter.

FIG. 36 shows a similar embodiment of the energy delivery element of FIG. 35 comprising one or more perforations 3502 and one or more electrodes 3503, except that the substrate further comprises a raised edge 3504 along at least a portion of the array 3606 that is adjacent to the stapes footplate 3601. Raised edge 3504 is configured to prevent any adhesive applied to the back side (facing away from the target tissue) of the energy delivery element 3606 from migrating toward the stapes footplate 3601 that could disrupt the conductive hearing pathway. In some embodiments, the raised edge 3504 is at a substantially right angle relative to a body of the substrate. In other embodiments, the raised edge 3504 is at an angle of about 30 degrees to about 120 degrees; about 45 degrees to about 100 degrees; about 45 degrees to about 90 degrees; about 50 degrees to about 70 degrees; etc. relative to a body of the substrate.

Figure 39:
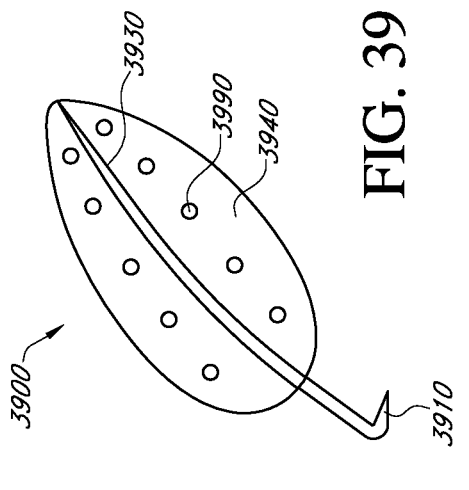
FIG. 39 shows another embodiment of an energy delivery element including a tissue piercing element.
Figure 37:
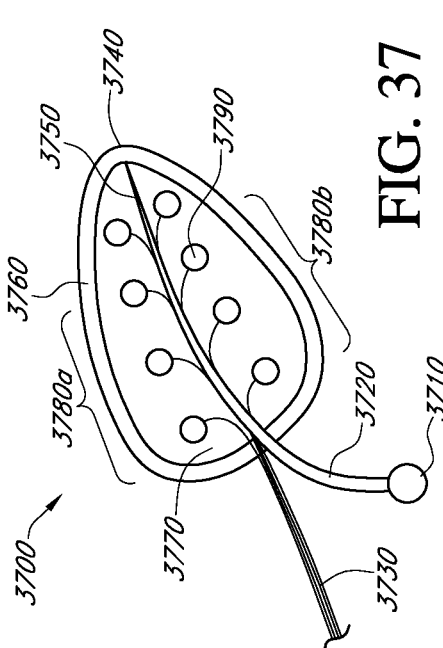
FIG. 37 shows another embodiment of an energy delivery element including a ball electrode insertable in a round window.
Figure 38:
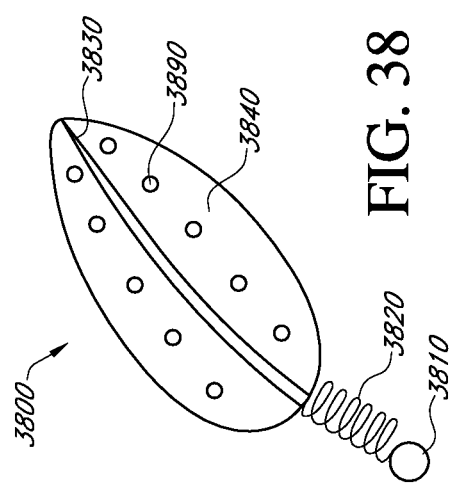
FIG. 38 shows another embodiment of an energy delivery element including a ball electrode extending from the body via a compressible lead.

FIGS. 37-39 show various embodiments of energy delivery elements that each include a round window membrane interaction element (e.g., ball electrode, tissue piercing element, etc.). Turning first to FIG. 37, energy delivery element 3700 includes substrate 3770 having a first convex section 3780a opposite a second convex section 3780b. The first and second convex sections 3780a, 3780b join at tip 3740 of element 3700. When positioned in the middle ear cavity, tip 3740 of element 3700 may approach the Eustachian tube orifice. The radius of curvature of the first and second convex sections may be similar, or different, for example, depending on the structure of the middle ear cavity, cochlea, etc. of the patient. In this embodiment, energy delivery element 3700 comprises an electrode array comprising a plurality of electrodes 3790. Each electrode 3790 may include leads that extend from each electrode and join with interconnect 3730. Optionally, the array may include a circumferential ground electrode 3760 or other ground electrode configuration. An insulated conductor 3720 extends from ball electrode 3710 (e.g., positionable for contact with the round window) along or through substrate 3770 as a backbone 3750 towards the tip 3740. Insulated conductor 3720 and backbone 3750 may be malleable, such that one or both may be flexed or adjusted to conform to a surface within the middle ear cavity. External hardware is electrically coupled to the implanted hardware via interconnect 3730, which is configured to pass through a facial recess or other access point into the middle ear cavity.

FIG. 38 shows another embodiment of an energy delivery element 3800 including a ball electrode 3810 extending from the substrate 3840 via a compressible lead 3820. Compressible lead 3820 may comprise a spring, shape memory alloy, a biased material, or the like. As above in FIG. 37, energy delivery element 3800 includes backbone 3830 and a plurality of electrodes 3890 and a similar substrate 3840 shape and configuration.

FIG. 39 shows another embodiment of an energy delivery element 3900, similar to that of FIGS. 37-38, including a tissue piercing or penetrating element 3910. Tissue piercing element 3910, in one embodiment, may be configured as a round window membrane piercing element 3910. Additionally, or alternatively, the tissue piercing element 3910 may also serve as a needle type electrode for interaction with the round window. Energy delivery element 3900 comprises a plurality of electrodes 3990 arranged along substrate 3940 and backbone 3930, as above with respect to FIGS. 37-38.

Figure 40:
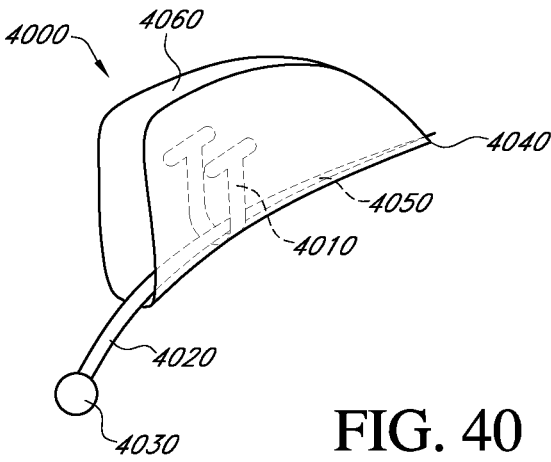
FIG. 40 shows an embodiment of an energy delivery element in a compressed configuration.
Figure 41:
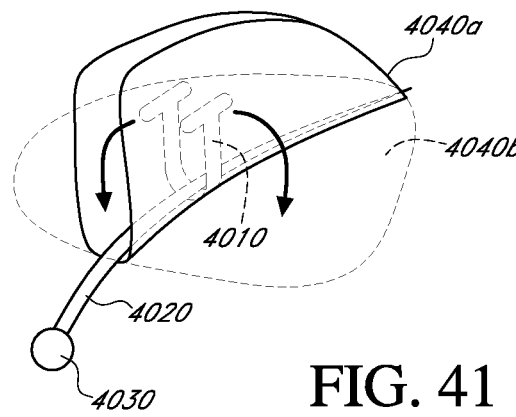
FIG. 41 shows the embodiment of FIG. 40 and how it is movable to an uncompressed or expanded configuration.
Figure 42:
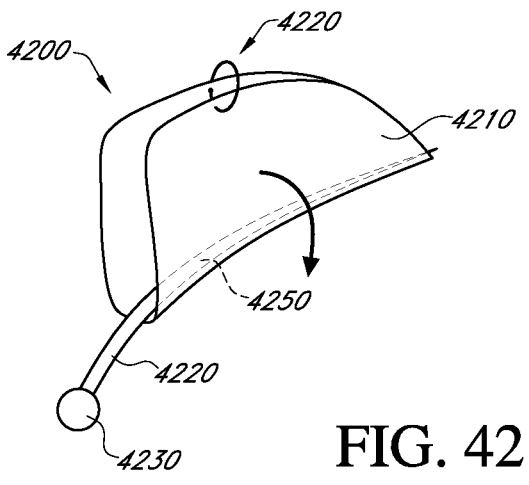
FIG. 42 shows another embodiment of an energy delivery element in a compressed configuration.

FIGS. 40-42 show various embodiments of energy delivery elements in a compressed configuration. Turning first to FIG. 40. FIG. 40 shows an energy delivery element 4000 comprising substrate 4060 comprising backbone 4050 that extends towards tip 4040. Backbone 4050 forms part of insulated conductor 4020, which is electrically connected to round electrode 4030, for example for positioning in a round window. Energy delivery element 4000 is compressible along backbone 4050 into a compressed or folded configuration. In one embodiment, a tissue contacting surface or top surface of the energy delivery element forms an interior of the folded configuration; in another embodiment, a tissue contacting surface of the energy delivery element forms an exterior of the folded configuration.

Substrate 4060 is maintained in the folded configuration via tabs 4010. Tabs 4010 may comprise a malleable material, shape memory alloy, other biased material, or the like. Upon insertion in the middle ear cavity, tabs 4010 may be adjusted to release the energy delivery element 4000 from its folded configuration. At which point, tabs 4010 may be re-used or further utilized to conform the substrate to a surface of the cochlea, or other surface in the middle ear cavity, by applying directed pressure on the substrate against the target surface.

FIG. 41 shows the embodiment of FIG. 40, and is thus similarly labeled to FIG. 40, and how it is movable to an uncompressed or expanded configuration. As shown in FIG. 41, the compressed or folded configuration 4040a (also shown in FIG. 40) is movable to the uncompressed or unfolded configuration 4040b, shown by the dotted lines. Transitioning between the folded 4040a and unfolded 4040b configurations occurs via active or passive manipulation of tabs 4010, as described above for FIG. 40.

FIG. 42 shows another embodiment of an energy delivery element 4200 in a compressed configuration. In this embodiment, the tabs of FIGS. 40-41 are replaced with sutures 4220, such that after delivery into the middle ear cavity, sutures 4220 can be cut or removed so that substrate 4210 may flatten and/or conform to a surface on which it is positioned. For example, substrate 4210 may flatten about backbone 4250 which forms part of insulated conductor 4220 connected to ball electrode 4230. In any of the embodiments described herein, for example FIGS. 37-42, the substrate may comprise silicone, polyurethane, a thermoplastic elastomer, or the like, such that the substrate is biased towards a substantially flat or planar configuration when it is released from the compressed or folded configuration.

FIGS. 43A-44B show similar overall shape and configuration of energy delivery elements as that of FIGS. 37-39, except in the embodiments of FIGS. 43A-44B, the compressed configuration comprises a rolled configuration as opposed to a folded configuration. Energy delivery element 4300, as shown in FIG. 43A, is in a partially compressed configuration, such that it is at least partially rolled about backbone 4350, which terminates at ball electrode 4330. Arrow 4320 shows how substrate 4340a is rolled upon itself about backbone 4350, such that a perimeter of the substrate folds in towards the backbone 4350 and the remaining substrate is rolled about the backbone 4350. Although FIG. 43A shows substrate 4340a rolling such that a top surface 4360a (tissue interaction surface) of the array is in an interior of the compressed configuration, one of skill in the art will appreciate that the array may be compressed such that a bottom surface 4360b (side of the array opposite the target tissue) is in an interior of the compressed configuration. In FIG. 43B, energy delivery element 4300b is in a fully compressed, unexpanded, or rolled configuration. In this embodiment, a bottom surface 4340b of the substrate forms an exterior of the rolled configuration, although as described above, an energy delivery element may also be rolled or compressed such that a top or tissue contacting surface forms an exterior of the rolled configuration. The energy delivery element 4300b may be maintained in the compressed configuration via suture 4350, tabs, a tie, or the like. In one embodiment, a tie may comprise a dissolvable material or a medical grade suture material. Alternatively, or additionally, a tie may comprise a tether or extension of another portion of the energy delivery element, for example from an electrode, that is configured to encircle the compressed configuration and maintain it in the compress configuration. After delivery into the middle ear cavity, suture 4350 may be cut or otherwise undone so that the energy delivery element 4300*b* may form an uncompressed or unrolled configuration. Alternatively, or additionally, an energy delivery element 4300*b* may be maintained in a compressed configuration via a delivery instrument, for example having an elongate body defining a tube therethrough. The energy delivery element 4300*b* while at least partially disposed in the delivery instrument may be maintained, at least partially, in the compressed or rolled configuration.

Figures 52, 53:
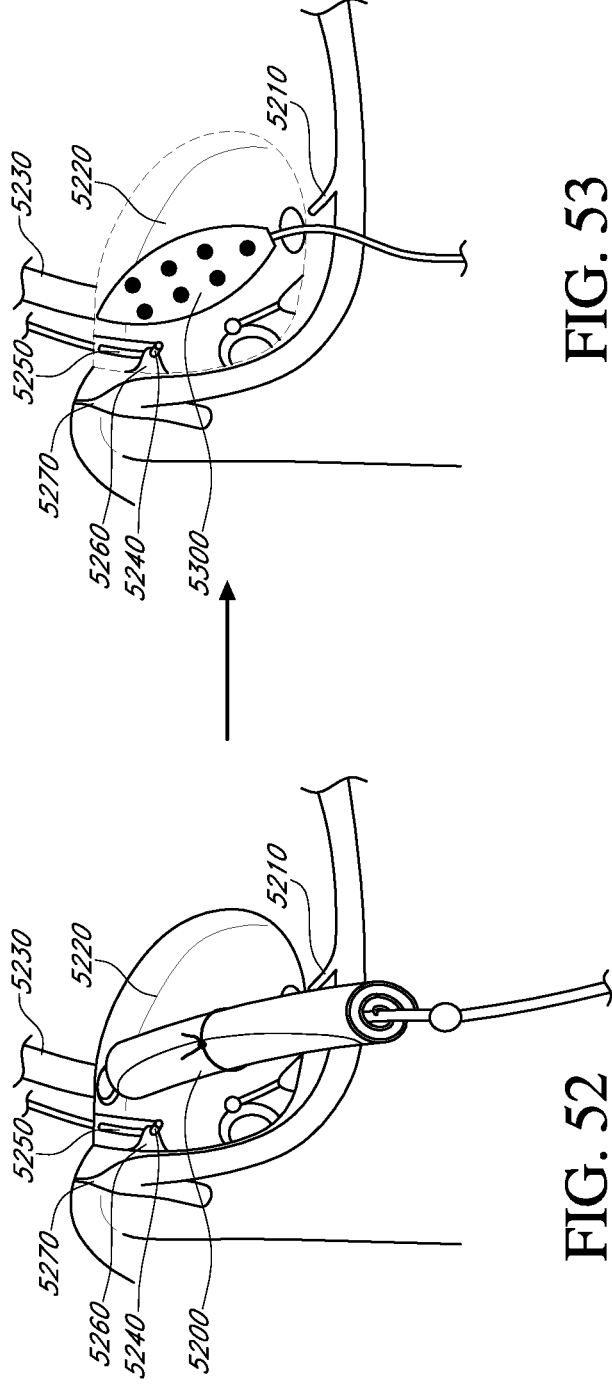
FIG. 52 shows an energy delivery element in a compressed configuration, positioned in the middle ear cavity after being delivered through the facial recess.
FIG. 53 shows an energy delivery element in an expanded configuration, positioned in the middle ear cavity after being delivered through the facial recess.

FIG. 52 shows an energy delivery element 5200 in a compressed configuration, similar to the compressed configuration shown in FIG. 43B, positioned in the middle ear cavity after being delivered through the facial recess (using any of the methods described elsewhere herein). FIG. 53 shows the energy delivery element 5300 in an expanded configuration, similar to the expanded configuration at least partially shown in FIG. 43A, positioned in the middle ear cavity after being delivered through the facial recess (using any of the methods described elsewhere herein). The chorda tympani 5210, Jacobson's nerve 5220, Eustachian tube 5230, Tensor tympani tendon 5240, Cochleariform process 5260, and greater superficial petrosal nerve 5270 are shown in FIGS. 52-53 for general orientation.

FIG. 44A is similar to FIG. 43A, except in this embodiment, ball electrode 4430 is tethered both to energy delivery element 4400 and to a delivery tool 4470 (e.g., catheter, guidewire, applicator, etc.). After delivery to the middle ear cavity, for example via a facial recess, energy delivery element 4400 may be untethered or cut from the delivery tool, for example at separation point 4460, leaving interconnect 4480 to pass through the facial recess to electrically connect to external hardware, as described elsewhere herein. Alternatively, as shown in FIG. 44B, ball electrode 4430 may include a slot 4490 therein that is configured to interact with the delivery tool 4470. After delivery to the middle ear cavity, delivery tool 4470 is removed from slot 4490 to release the ball electrode 4430, and thus an energy delivery element attached thereto, from the delivery tool.

Figure 45:
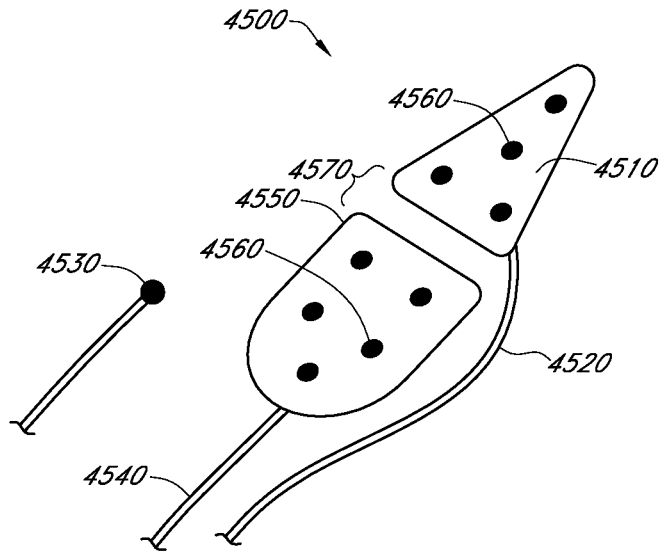
FIG. 45 shows another embodiment of an energy delivery element having distal and proximal arrays.

FIG. 45 shows another embodiment of an energy delivery element 4500 having distal 4510 and proximal 4550 elements or arrays. As shown in FIG. 45, the distal 4510 and proximal 4550 arrays may not be coupled to one another; in other embodiments, the distal 4510 and proximal 4550 arrays may be tethered or coupled to one another via a lead or nonconductive cable or coupling element. In the embodiment shown in FIG. 45, the distal array 4510 comprises insulated conductor 4520 and the proximal array 4550 also comprises an insulated conductor 4540. Further, each array comprises one or more energy delivery elements, for example electrodes 4560. The modular design of FIG. 45 enables the distal array 4510 to be positioned independent from the proximal array 4550. For example, a distance 4570 between the arrays may be increased or decreased to appropriately cover one or more surfaces in the middle ear cavity. Additionally, or alternatively, the arrays may be offset relative to one another to appropriately cover one or more surfaces in the middle ear cavity. Energy delivery element 4500 may further include ball electrode 4530, for example for interaction with the round window membrane or round window niche. Ball electrode 4530 may be electrically connected to either or both arrays 4510, 4550 or a separate energy delivery element.

Figure 46:
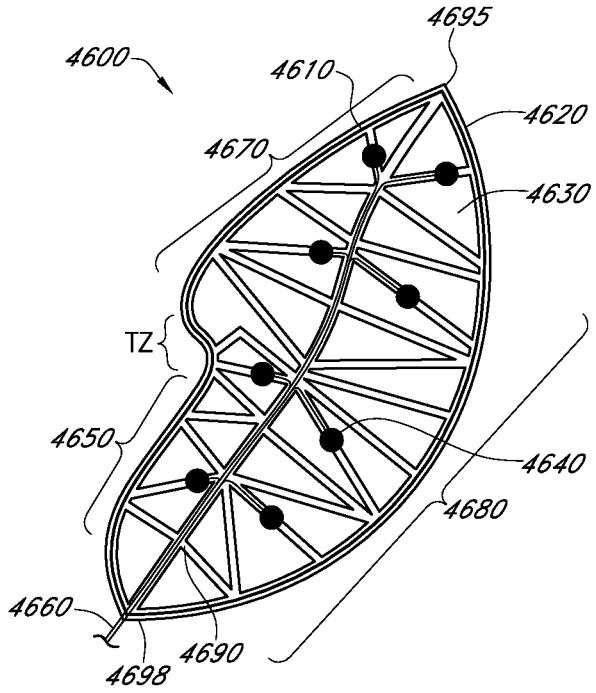
FIG. 46 shows another embodiment of an energy delivery element having a substrate scaffold defining one or more perforations.

FIG. 46 shows another embodiment of an energy delivery element 4600. Energy delivery element 4600 comprises a substrate 4620 defining one or more perforations 4630. Energy delivery element 4600 includes one or more electrode contacts 4640 that are configured to be apposed to the target tissue surface. In one embodiment, electrode contacts 4640 are unexposed on a back or bottom side of the substrate that is opposite or not adjacent to the target tissue surface. Further, energy delivery element 4600 optionally includes ground electrode 4610 disposed about a perimeter of the substrate 4620, for example to limit current spread to adjacent non-target tissues in the middle ear cavity. Insulated conductors 4660 are electrically connected to each electrode through the substrate, for example along a backbone 4690 but may also run through other portions or regions of the substrate. Substrate 4620 may include a first convex section 4680 opposite a concave section 4650 that transitions to a second convex section 4670. The transition zone TZ between the concave section 4650 and the second convex section 4670 may be angled between about 30 degrees to about 170 degrees; about 60 degrees to about 120 degrees; or substantially 90 degrees. The first convex section 4680 may meet the second convex section 4670 at distal point 4695 opposite the first convex section 4680 meeting the concave section 4650 at proximal point 4698.

Figures 48A, 48B, 48C, 48D, 48E, 48F:
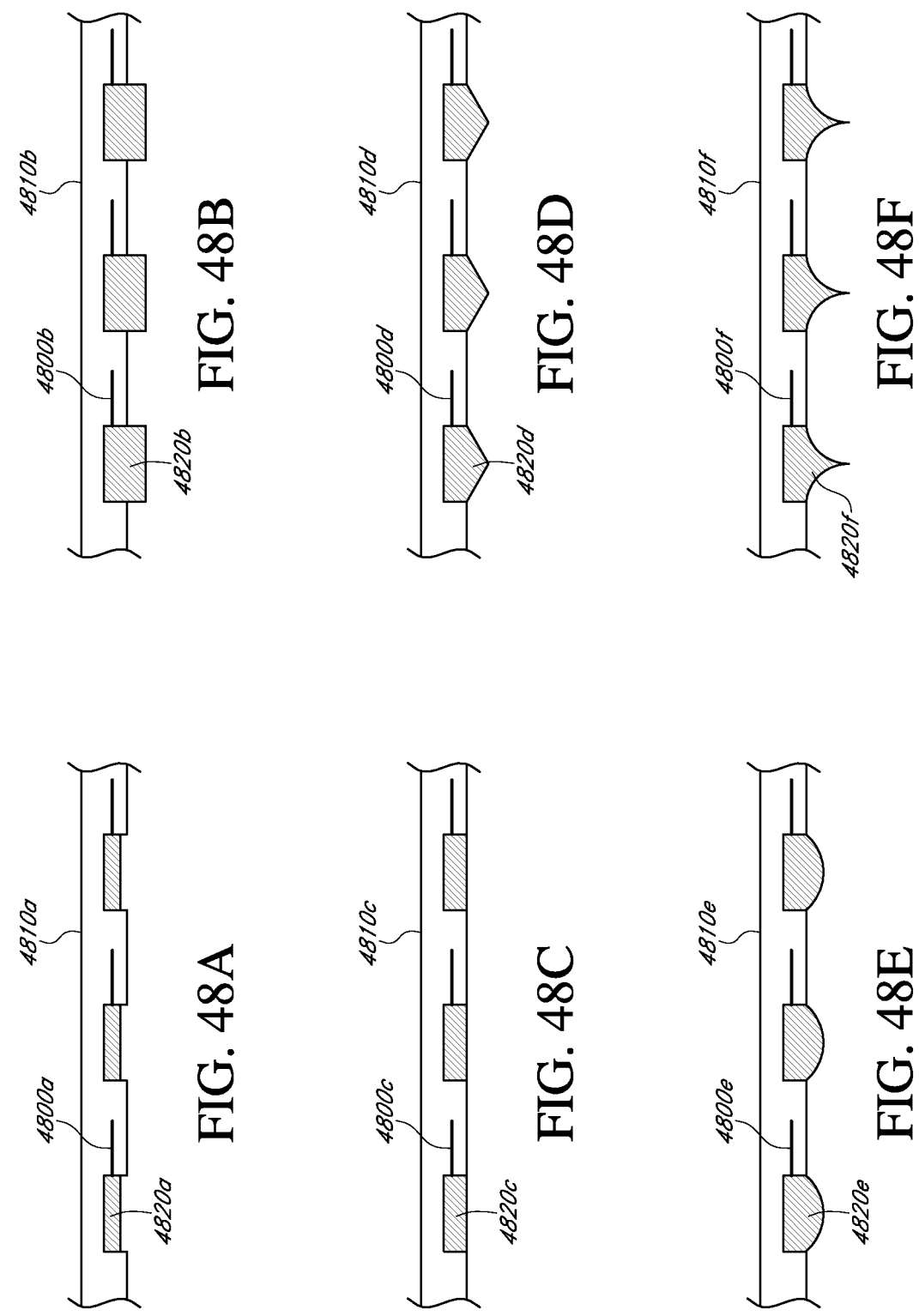
FIGS. 48A-48F show various electrode shapes and degree of protrusion from or embedded in a substrate.

FIGS. 48A-48F show various electrode shapes and degrees of protrusion from a substrate or embedded in a substrate. Any of the electrode shapes or designs shown in FIGS. 48A-48F may be used in any of the energy delivery elements or arrays shown and described elsewhere herein. FIG. 48A shows an electrode contact 4820*a* recessed in a substrate 4810*a* with a lead 4800*a* embedded in the substrate 4810*a*. Electrode contact 4820*a* may be recessed by about 0.01 mm to about 1 mm. FIG. 48B shows an electrode contact 4820*b* that is extruded from the substrate 4810*b* with a lead 4800*b* embedded in the substrate 4810*b*. Electrode contact 4820*b* may be extruded from the substrate 4810*b* by about 0.01 mm to about 1 mm. FIG. 48C shows an electrode contact 4820*c* that is flush with a surface 4812*c* of the substrate 4810*c*. Electrode contact 4820*c* includes lead 4800*c* embedded in substrate 4810*c*. FIG. 48D shows an electrode contact 4820*d* that includes a cone point extending out of the substrate 4810*d*. Each electrode contact 4820*d* includes lead 4800*d* embedded in substrate 4810*d*. FIG. 48E shows an electrode contact 4820*d* having a convex surface extending from the substrate 4810*e*. Each electrode contact 4820*e* includes lead 4800*e* embedded in substrate 4810*e*. FIG. 48F shows an electrode contact 4820*f* that includes a point formed from concave surfaces of the electrode contact 4820*f* meeting at an apex. The electrode contact 4820*f* and lead 4800*f* are embedded in substrate 4810*f*.

Figure 49A:
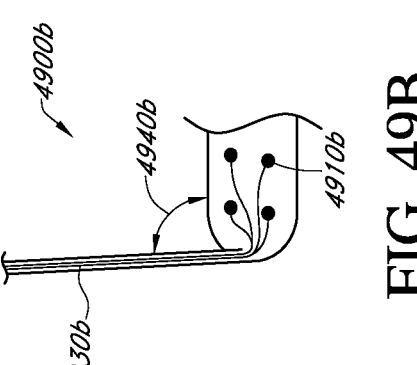
FIGS. 49A-49D show various lead configurations stemming from an energy delivery element.
Figure 49B:
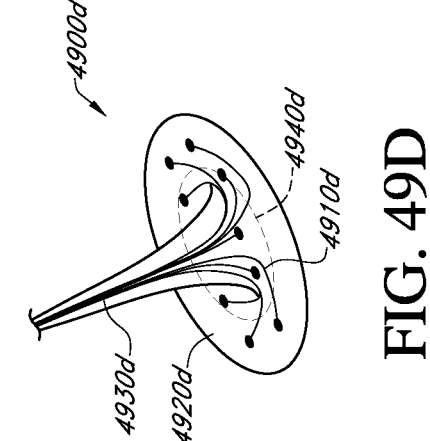
Figure 49C:
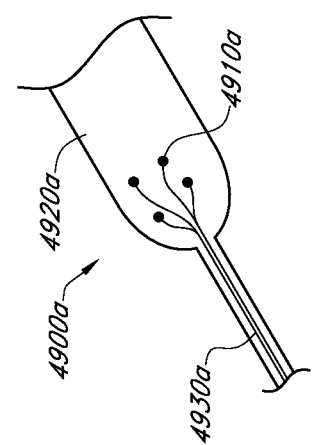
Figure 49D:
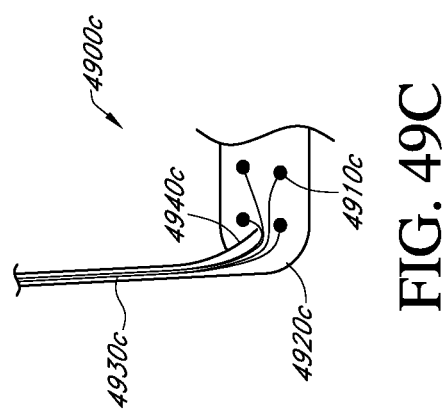

FIGS. 49A-49D show various lead configurations stemming from an energy delivery element. As can be appreciated by one of skill in the art, any of these lead configurations may be combined with any of the electrode shapes or configurations described elsewhere herein and/or combined with any of the energy delivery elements described elsewhere herein. FIG. 49A shows an energy delivery element 4900*a* comprising a plurality of electrodes 4910*a* embedded in a substrate 4920*a*, with leads 4930*a* extending from the plurality of electrodes 4910*a*. The leads 4930*a* are in a substantially same plane or colinear with the substrate 4920*a* and/or the electrodes 4910*a*. In some embodiments, this configuration is particularly suited for delivery through a facial recess, although other delivery methods are also contemplated herein. FIG. 49B shows an energy delivery element 4900*b* comprising a plurality of electrodes 4910*b* embedded in a substrate, with leads 4930*b* extending from the plurality of electrodes 4910*b*. The leads 4930*b* form an angle 4940b with respect to a plane of the substrate and/or the electrodes 4910b. Angle 4940b may be about 180 degrees to about 80 degrees; about 120 degrees to about 80 degrees; or substantially about 90 degrees. FIG. 49C shows an energy delivery element 4900c comprising a plurality of electrodes 4910c embedded in a substrate 4920c, with leads 4930c extending from the plurality of electrodes 4910c. Substrate 4920c may include a widened section 4940c where the leads 4930c extend from the substrate 4920c. This widened section 4940c may provide strain relief to prevent or reduce stress on individual leads. This widened section 4940c may be wider than the leads when in aggregate but thinner than a width of the substrate in its expanded configuration. FIG. 49D shows an energy delivery element 4900d comprising a plurality of electrodes 4910d embedded in a substrate 4920d, with leads 4930d extending from the plurality of electrodes 4910d. In the embodiment of FIG. 49D, leads 4930d extend from a substantially central region 4940d of substrate 4920d. Further, the leads 4930d may either extend from substrate 4920d at a substantially right angle, as in FIG. 49B, or in a tapered or strain relief fashion, as in FIG. 49C.

Figure 54:
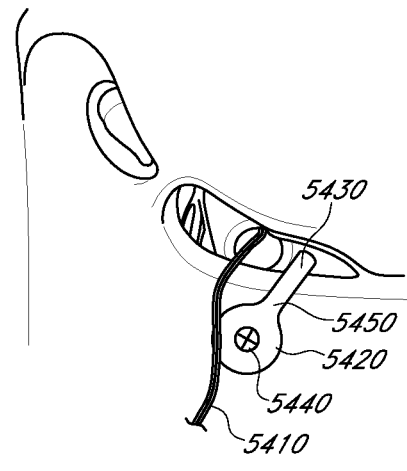
FIG. 54 shows an embodiment of a plate extending through a facial recess and into a middle ear cavity to apply pressure to an energy delivery element positioned therein.
Figure 55:
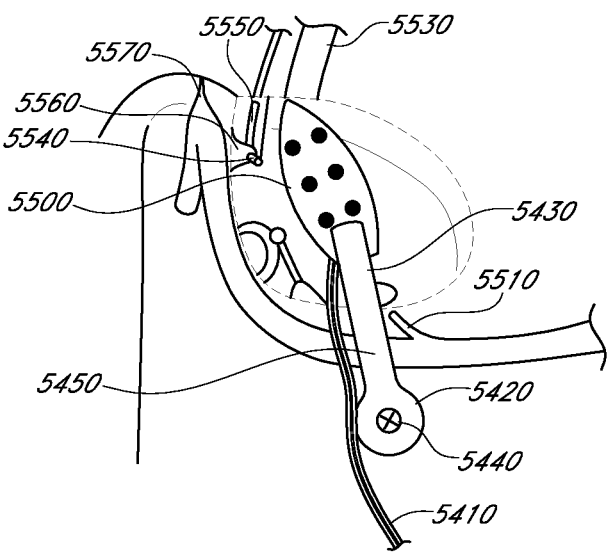
FIG. 55 shows the plate of FIG. 54 applying pressure to an energy delivery element positioned in the middle ear cavity.

FIG. 54 shows an embodiment of a plate extending through a facial recess and into a middle ear cavity to apply pressure to an energy delivery element positioned therein. FIG. 55 shows (via a cutaway view with the temporal bone removed) the plate of FIG. 54 applying pressure to an energy delivery element positioned in the middle ear cavity. As shown in FIGS. 54-55, plate 5450 comprises a distal portion 5430 that is configured to apply pressure to an energy delivery element 5500 positioned in the middle ear cavity and a proximal portion 5420 that extends through the facial recess and may be fixed to a temporal bone using one or more screws 5440. At least the distal portion 5430 of plate 5450 may comprise a leaf spring or malleable metal plate such that it is configured to apply a downward pressure on an electrode array in a middle ear cavity. The lead 5410 from energy delivery element 5500 extends through facial recess to external hardware. The chorda tympani 5510, Jacobson's nerve 5520, Eustachian tube 5530, Tensor tympani tendon 5540, Cochleariform process 5560, and greater superficial petrosal nerve 5570 are shown in FIG. 55 for general orientation.

Figure 56:
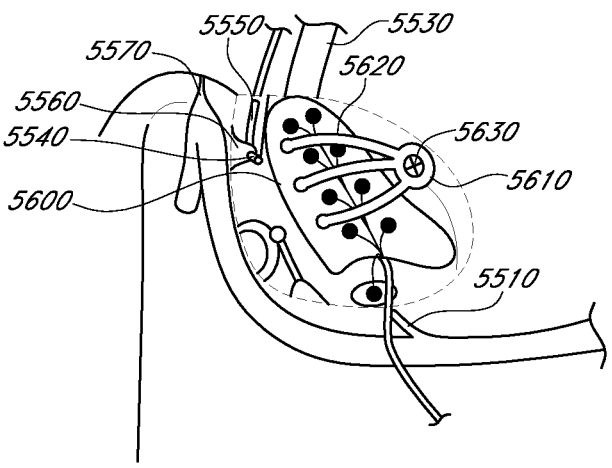
FIG. 56 shows an anchoring mechanism for an energy delivery element.

FIG. 56 shows another anchoring mechanism 5610 for securing an energy delivery element 5600 in a middle ear cavity. Anchoring mechanism 5610 comprises one or more arms 5620 that extend at least partially across a substrate of the energy delivery element 5600. Each of the arms 5620 is configured to apply a downward force on the energy delivery element 5600. For example, each of the arms 5620 may comprise a leaf spring, malleable material, biased material, or the like. A head 5630 of the anchoring mechanism 5610 may be secured to hypotympanum via a fastener, for example a screw. The chorda tympani 5510, Eustachian tube 5530, Semicanal 5550, Tensor tympani tendon 5540, Cochleariform process 5560, and greater superficial petrosal nerve 5570 are shown in FIG. 56 for general orientation.

Figure 57:
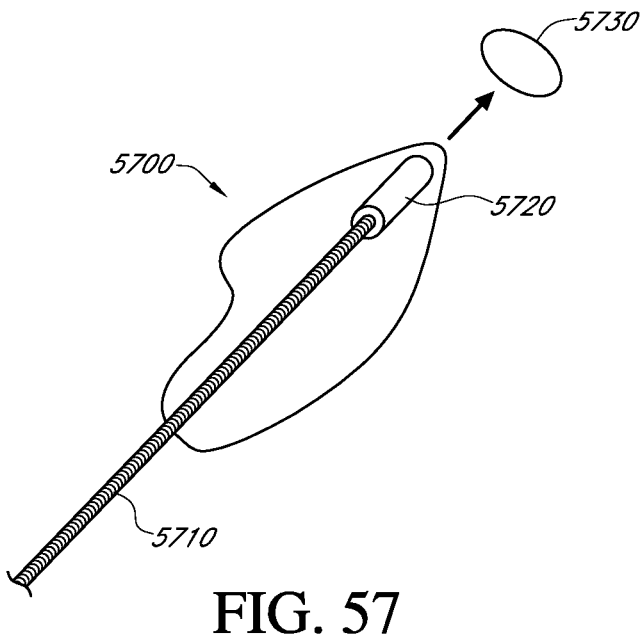
FIG. 57 shows a guidewire delivery device for delivering an energy delivery element.
Figure 58:
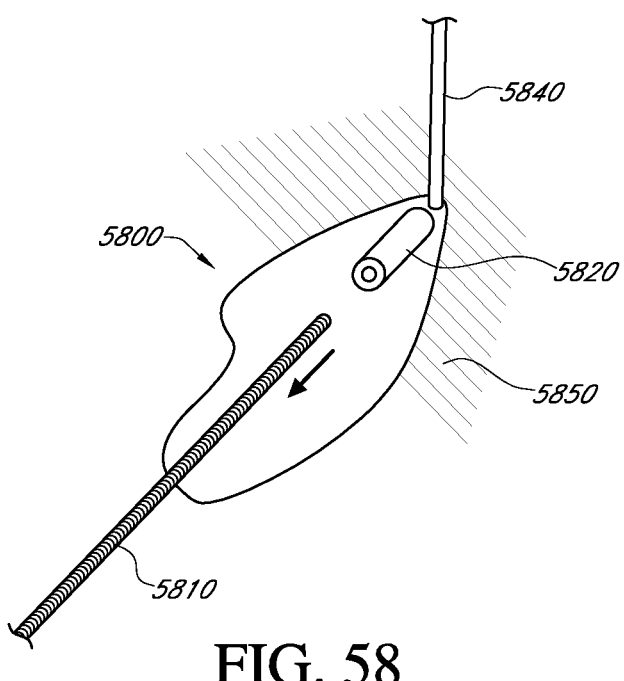
FIG. 58 shows removal of the guidewire delivery device from the energy delivery element of FIG. 57.

In some embodiments, as shown in FIGS. 57-58, a guidewire-based delivery tool may be used for delivering any of the energy delivery elements described elsewhere herein. As shown in FIG. 57, an energy delivery element 5700 may include a pocket or reversible attachment mechanism 5720 into which a guidewire 5710 or similar tool is insertable or to which the guidewire 5710 is reversibly couplable. The energy delivery element 5700 coupled to the guidewire 5710 may then be inserted through the facial recess 5730 for delivery into the middle ear cavity. Once the energy delivery element 5800 is positioned, for example, on the promontory surface 5850, as shown in FIG. 58, the guidewire 5810 may be uncoupled from the energy delivery element 5800, for example, by using a tool 5840 to apply pressure to a distal end of the energy delivery element while the guidewire 5810 is removed or uncoupled from the attachment mechanism 5820.

Figure 59:
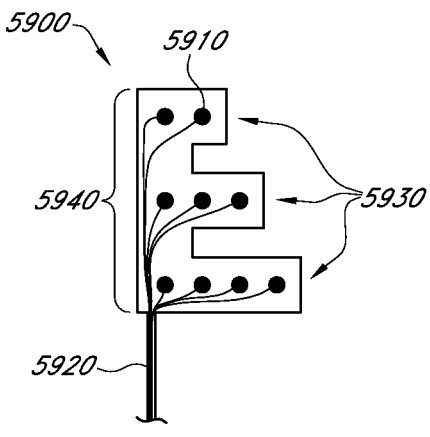
FIG. 59 shows another embodiment of an energy delivery element.
Figure 60:
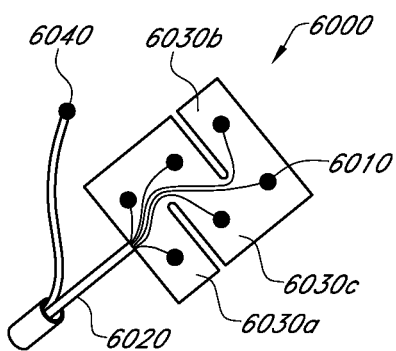
FIG. 60 shows another embodiment of an energy delivery element.

FIGS. 59-64 show various embodiments of energy delivery elements. For example, FIG. 59 shows an energy delivery element 5900 having one or more legs 5930 extending from an elongate section 5940 that is substantially colinear with or in line with one or more leads 5920 emanating from one or more electrodes 5910. As shown, there may be three legs 5930, or two, or one, or more than three, or a plurality. The legs 5930 may have a similar length or range in lengths or the length of each leg may be personalized for an anatomy of the patient. FIG. 60 shows an energy delivery element 6000 having a first leg 6030a extending from a first side (e.g., right side) and a second leg 6030b extending from a second side (e.g., left side), opposite the first side. The first and second legs may be linearly opposite one another or diagonally offset, as shown in FIG. 60. The first leg 6030a is connected to the second leg 6030b via transition section 6030c, such that the first leg 6030a, transition section 6030c, and second leg 6030b together form a substantially S-shaped pattern or a substantially sigmoidal curve. There may be zero or more electrodes per leg or section. For example, in the embodiment of FIG. 60, there are two electrodes per leg or section. Leads 6020 extend from each of the electrodes 6010. Optionally, ball or accessory electrode 6040 may form part of the energy delivery element 6000.

Figure 61:
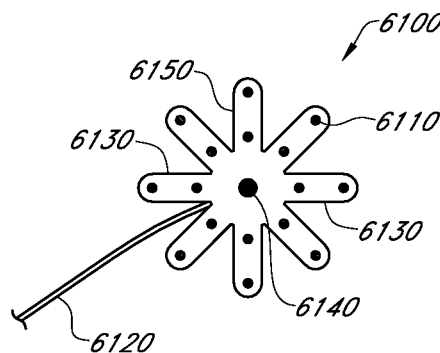
FIG. 61 shows another embodiment of an energy delivery element.
Figure 62:
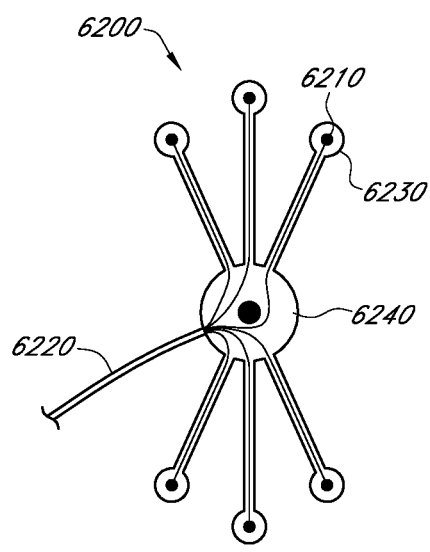
FIG. 62 shows another embodiment of an energy delivery element.
Figure 63:
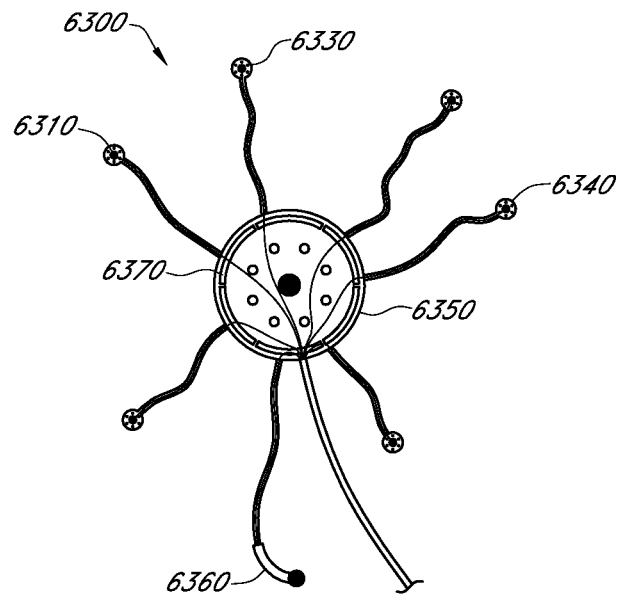
FIG. 63 shows another embodiment of an energy delivery element.

FIG. 61 shows another embodiment of an energy delivery element 6100 having a stellate shaped substrate 6150. The stellate shape comprises a plurality of legs 6130 extending from a central body 6140, which may or may not include an electrode or a ground electrode. Each of the legs 6130 may include zero or more electrodes 6110 embedded therein. For example, as shown in FIG. 61, each leg includes two electrodes 6110 embedded therein. An insulated conductor 6120 extends from the substrate and comprises one or more leads from the electrodes. The energy delivery element 6200 of FIG. 62 is similar to FIG. 61, except that each leg 6230 extending from a central body 6240 includes a terminal electrode 6210. As above, the central body 6240 may or may not include an electrode or a ground electrode. An insulated conductor 6220 extends from the substrate and comprises one or more leads from the electrodes. The energy delivery element 6300 of FIG. 63 is similar to FIG. 62, except that the terminal end 6340 of each leg 6330 defines one or more perforations for adhesion or integration of the substrate with the target surface in the middle ear cavity. Legs 6330 extend from central body 6350, which may or may not include an electrode or ground electrode. Further, the terminal end of each leg 6330 includes an electrode 6310. However, as one of skill in the art will appreciate, while all terminal ends of all legs are shown comprising an electrode, it is also contemplated herein that only a subset of the legs include an electrode. Central body 6350 may further define one or more perforations 6370 to promote adhesion and/or integration of the substrate with the target tissue. The perforations 6370 may be elongate or punctate or along a perimeter or circumscribing the central body or otherwise positioned anywhere in the central body. Optionally, energy delivery element 6300 includes an accessory or ball electrode 6360, for example for positioning in a round window.

Figure 64:
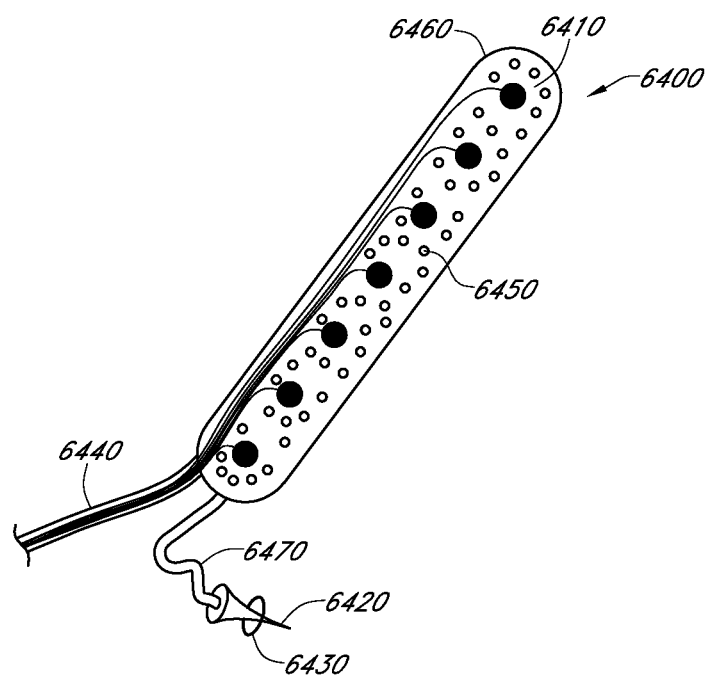
FIG. 64 shows another embodiment of an energy delivery element having an elongate or linear configuration.

FIG. 64 shows another embodiment of an energy delivery element 6400 comprising a substantially linear arrangement of electrodes 6410 along the length of the substrate 6460. The substrate 6460 further defines one or more perforations therein for promoting adhesion or integration with a target tissue. Insulated conductor 6440 is electrically connected to external hardware (e.g., an implanted stimulator). Element 6400 may further include a round window electrode 6420 that is substantially maintained in the round window via collar or cuff 6430 that at least partially circumscribes the lead 6470 connected to the round window electrode 6420.

Figure 65A:
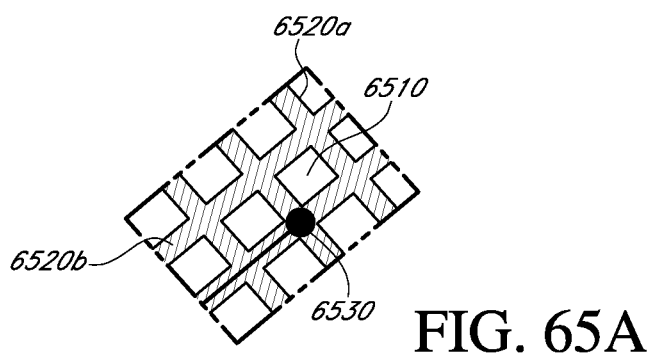
FIGS. 65A-65D show various perforation configurations for promoting tissue integration or adhesion.
Figure 65B:
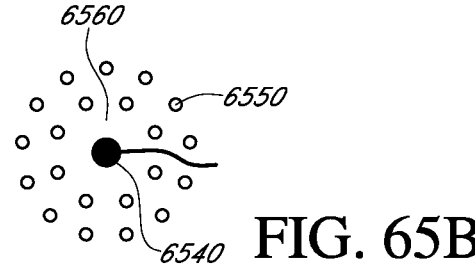
Figure 65C:
Figure 65D:
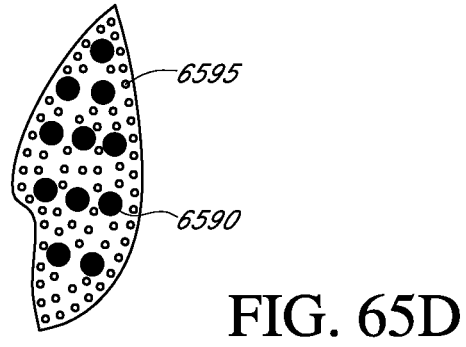

FIGS. 65A-65D show various perforation configurations for promoting tissue integration or adhesion. The perforation configurations of FIGS. 65A-65D may be used in combination with any of the energy delivery elements described elsewhere herein. FIG. 65A shows a perforation design in which longitudinally oriented substrate strips 6520a intersect with latitudinally oriented substrate strips 6520b at substantially right angles to define polygonal perforations 6510. One or more electrodes 6530 may be positioned at the intersection point between the longitudinal 6520a and latitudinal 6520b strips. FIG. 65B shows another perforation configuration where each of the perforations 6550, defined by the substrate 6560, are substantially circular, oval, or ellipse in shape. The perforations 6550 may be disposed about an electrode 6540 to promote persistent electrical contact between the electrode 6540 and the target surface. FIG. 65C shows another perforation configuration comprising one or more concentrically arranged perforations 6570 about an electrode 6580. FIG. 65D shows another perforation configuration where the perforations are irregular (e.g., vary in size, shape, etc.) and/or stochastically arranged (e.g., vary in density, distribution, etc.) to promote adhesion and/or integration with the target tissue.

FIG. 66A shows another embodiment of an energy delivery element 6600. Energy delivery element 6600 comprises a substrate 6610 and one or more electrodes 6620. FIG. 66B shows a zoomed-in view of an electrode contact 6620 of the energy delivery element 6600 of FIG. 66A. Substrate 6610 defines an aperture 6640 around electrode contact 6620. Aperture 6640 is configured to promote tissue growth around the electrode contact 6620 for long-term electrical contact. Non-electrode areas, such as area 6630, may be fully electrically insulated to prevent current leak.

FIG. 67A-67C show various energy delivery element configurations and shapes, any of which may be employed with any of the other array configurations or shapes described elsewhere herein. The element 6700a of FIG. 67A shows a circumferential ground electrode 6710, about one or more interior electrodes 6720, configured to prevent off-target effects and/or current leak. FIG. 67B shows an energy delivery element 6700b comprising a plurality of large electrodes 6730 that cover a majority of the surface area of the substrate to maximize contact surface area and charge injection capability. For example, in some embodiments, about 90% or less than 90% of the surface area of the area is consumed by electrical contacts. In other embodiments, between about 10% and about 90%; between about 30% to about 60%; between about 40% to about 70%; between about 20% to about 80%; etc. of the surface area of the energy delivery element is consumed by electrical contacts. FIG. 67C shows another energy delivery element 6700c comprising a central electrode 6710 and a plurality of peripheral electrodes 6730 disposed in or on the substrate 6720.

Figures 68A, 68B, 68C:
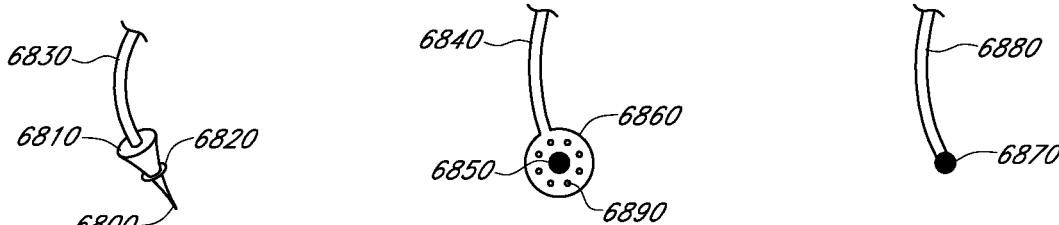
Figures 68D, 68E, 68F:
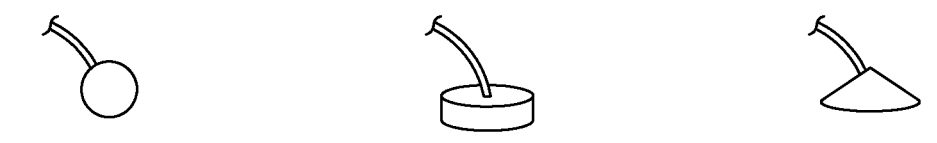

FIGS. 68A-68J show various round window electrode designs, any of which may be used with any other embodiment described elsewhere herein. For example, FIG. 68A shows an insulated conductor 6830 coupled to an electrode 6800. The electrode 6800 maintains its position in the round window via a first cuff 6820 and a second cuff 6810, such that the round window membrane may be positioned between the first 6820 and second 6810 cuffs. FIG. 68B shows an insulated conductor 6840 coupled to a patch 6860 defining one or more perforations 6890 and comprising an electrode 6850. FIG. 68C shows an insulated conductor 6880 coupled to a ball electrode 6870. The ball electrode may take on various shapes or configurations, such as any of those shown in FIGS. 68D-68F. FIG. 68D shows a spherical electrode; FIG. 68E shows a cylindrical electrode; and FIG. 68F shows a tapered or cone-like electrode, where the insulated conductor may be attached at the tip of the cone or the base of the cone. FIGS. 68G-68I show electrodes that are configured to be placed within the round window niche. These electrodes may be in electrical communication with the round window membrane but are not in direct contact with the membrane in order to prevent disruption of the natural movement of the membrane, thereby preserving residual hearing. FIG. 68G shows an electrode having an interrupted ring shape or a ring with a cutout or removed region. FIG. 68H shows an electrode having a ring or circular shape. FIG. 68I shows a plurality of electrodes arranged in a stellate configuration. For example, individual electrodes are arranged opposite another electrode. For example, there may be two, four, six, eight, or even ten electrodes, each one of the pair being arranged opposite the other. Any of the electrodes shown in FIGS. 68G-68I may be self-sizing or self-expanding such that they are introduced in a compressed state and may expand to make contact with the walls of the round window niche. FIG. 68J shows at least part of a delivery system comprising an elongate tubular structure defining a lumen therethrough that may be used to constrain or compress round window electrodes for delivery. For example, a first and second end or leg of an interrupted ring shape electrode may be compressed towards one another during delivery and during positioning in the elongate tube. Any of the round window electrodes described herein may have a monopolar or bipolar construction, for example comprising one material or metal or two materials or metals, respectively. Any of the round window electrodes described herein that are circular, cylindrical, conical, spherical, or ring-shaped may have a diameter between 0.1 mm and 2 mm.

Figure 80A:
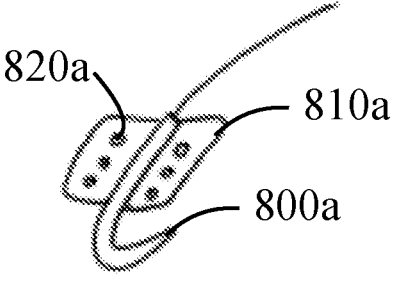
FIGS. 80A-80F show various electrode configurations for stimulation of a round window tissue.
Figure 80B:
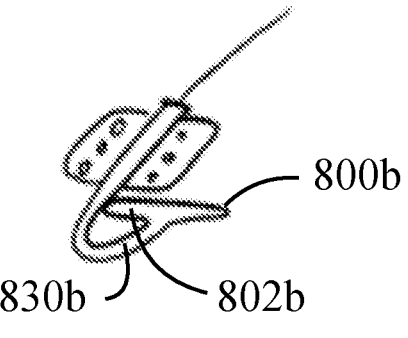
Figure 80C:
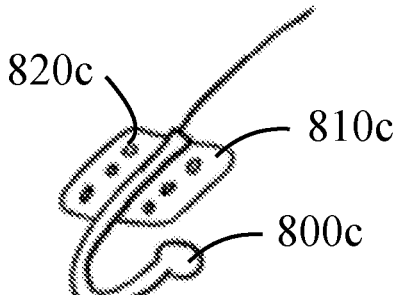
Figure 80D:
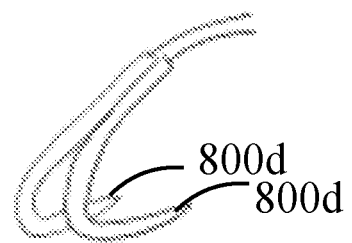
Figure 80E:
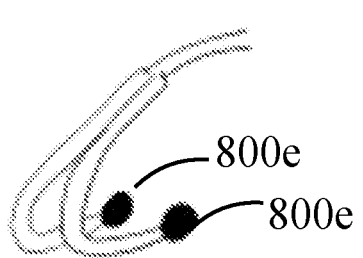
Figure 80F:
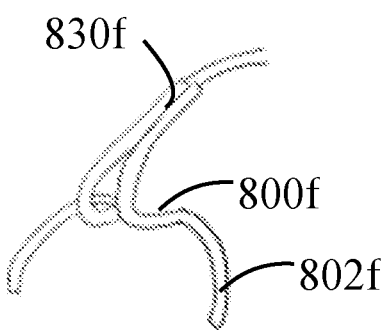

FIGS. 80A-80F show various electrode configurations for stimulation of a round window tissue. FIG. 80A shows a round window electrode comprising a hook or tissue anchoring end 800a. The round window electrode may further include a substrate 810a defining one or more apertures 820a for promoting tissue ingrowth or for application of an adhesive or the like. Optionally, as shown in FIG. 80D, there may be more than one or two tissue anchoring ends 800d. Further, optionally, as shown in FIG. 80E, the one or more anchoring ends may further include a sphere electrode 800e or other shape on a tip of each anchoring end. FIG. 80B shows another round window electrode comprising a first end 802b extending axially and opposite from a second end 800b that are substantially orthogonal or at right angles with respect to lead or interconnect 830b. The round window electrode shown in FIG. 80B similarly comprises a substrate defining one or more apertures. Further, any of the round window electrodes described herein may further include a substrate disposed about or on or coupled to the lead or interconnect and optionally defining one or more apertures therein. FIG. 80C is similar to FIG. 80A having a substrate 810c defining or more apertures 820c therein but further includes a round window electrode having a sphere configuration 800*c*. In some embodiments, as shown in FIG. 80F, there may be one or more electrodes extending from lead or interconnect 830*f* Each electrode may have a first section 800*f* that extends substantially perpendicularly from lead 830*f* and a second section 802*f* that extends substantially orthogonally or at a right angle from the first section 800*f* The first and second sections may extend in any plane that enables sufficient anchoring to or in the round window. Any of the round window electrodes described herein may have a monopolar or bipolar construction, for example comprising one material or metal or two materials or metals, respectively.

Figure 78:
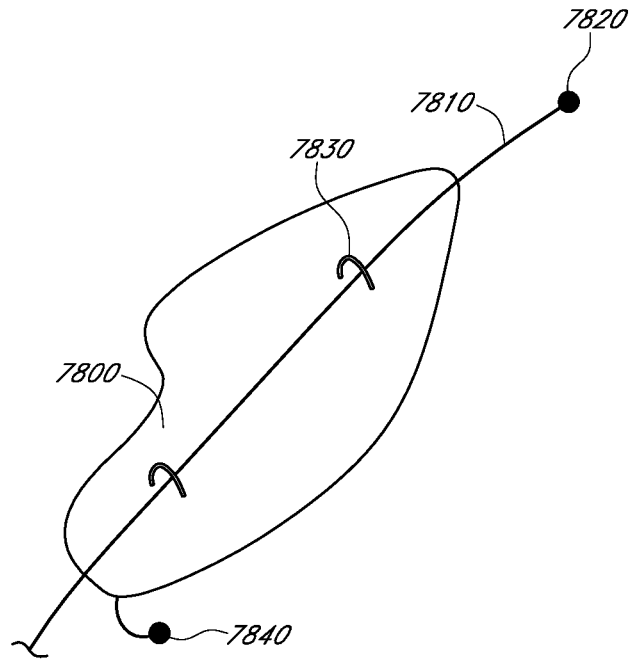
FIG. 78 shows a guidewire delivery system for delivering an energy delivery element.

FIG. 78 shows another embodiment of a guidewire delivery system. The system comprises a guidewire or similar device 7810 that is slidably coupled to a bottom side (opposite tissue facing side) an energy delivery element 7800. The guidewire 7810 may include a stop 7820 to prevent the guidewire from being removed from the brackets 7830 until the energy delivery element 7800 is properly positioned. The energy delivery element 7800 may include one or more, two or more, or a plurality of brackets 7830, in which the guidewire slides for positioning the energy delivery element 7800 during delivery. The energy delivery element 7800 may optionally comprise an electrode 7840 for contact with or stimulation of a round window membrane or tissue.

Figure 69:
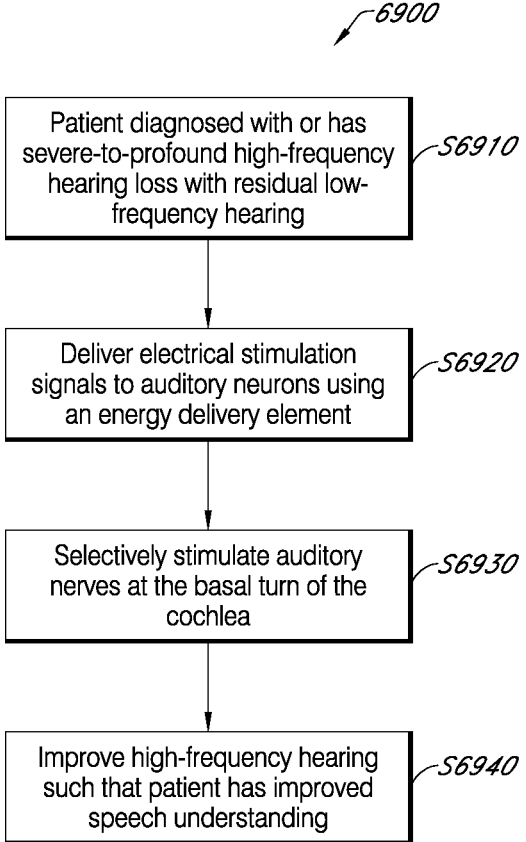
FIG. 69 shows one embodiment of a method of treating a patient having or diagnosed with a hearing condition.

A method 6900, as shown in FIG. 69, of using or employing any of the devices described herein may include having a patient diagnosed with or having severe-to-profound high-frequency hearing loss with residual low-frequency hearing at block 56910; delivering electrical stimulation signals to auditory neurons using an energy delivery element at block S6920; selectively stimulating auditory nerves at a basal turn of a cochlea at block 56930; and improving high-frequency hearing such that patient has improved speech understanding at block 56940. As appreciated by one of skill in the art, any of the method steps may be performed in any order or combined. Any of the energy delivery elements described herein may be used in combination with method 6900. In some embodiments, the method includes determining a level of speech understanding of the patient using one or more tests. Exemplary, non-limiting embodiments of tests include AzBio, CNC words, CNC sentences, or HINT Sentences in Noise and Quiet.

Figure 70:
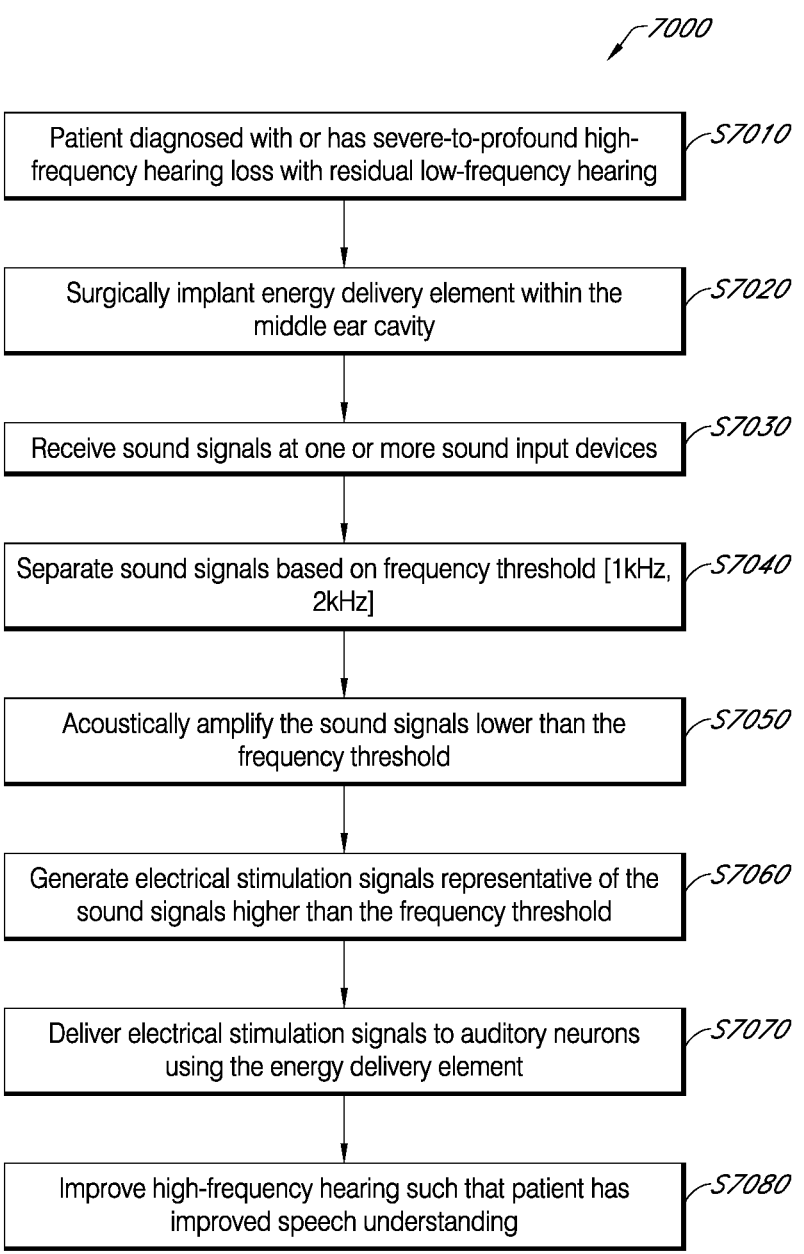
FIG. 70 shows another embodiment of a method of treating a patient having or diagnosed with a hearing condition.

Another method 7000, as shown in FIG. 70, of using or employing any of the devices described herein may include having a patient diagnosed with or having severe-to-profound high-frequency hearing loss with residual low-frequency hearing at block 57010; surgically implanting an energy delivery element within the middle ear cavity at block 57020 using any of the surgical methods described elsewhere herein; receiving sound signals at one or more sound input devices (e.g., a microphone in the external hardware) at block 57030; separating sound signals (e.g., via a speech or sound processor) based on a frequency threshold at block S7040; acoustically amplifying the sound signals lower than the frequency threshold at block S7050; generating electrical stimulation signals representative of the sound signals higher than the frequency threshold at block 57060; delivering electrical stimulation signals to auditory neurons using any of the energy delivery elements described herein at block 57070; and improving high-frequency hearing such that patient has improved speech understanding at block 57080. As appreciated by one of skill in the art, any of the method steps may be performed in any order or combined.

In some embodiments, delivering electrical stimulation signals comprises selectively stimulating auditory nerves at the basal turn of the cochlea.

In some embodiments, the frequency threshold is less than about 1 kHz. In some embodiments, the frequency threshold is less than or equal to about 1 kHz. In some embodiments, the frequency threshold is less than about 2 kHz. In some embodiments, the frequency threshold is less than or equal to about 2 kHz.

In some embodiments, delivering electrical stimulation signals comprises delivering a pattern of stimulation that encodes high-frequency sound information.

In some embodiments, the method includes determining a level of speech understanding of the patient using one or more tests. Exemplary, non-limiting embodiments of tests include AzBio, CNC words, CNC sentences, or HINT Sentences in Noise and Quiet.

In some embodiments, improving high-frequency hearing such that the patient has improved speech understanding comprising a measurable improvement in scores on a standardized sentence or word recognition test including AzBio, CNC words, CNC sentences, and HINT Sentences in Noise and Quiet. This improvement could be measured in absolute percentage improvement, of about 10% or greater or in relative percentage improvement on baseline, of about 20% or greater.

Figure 71:
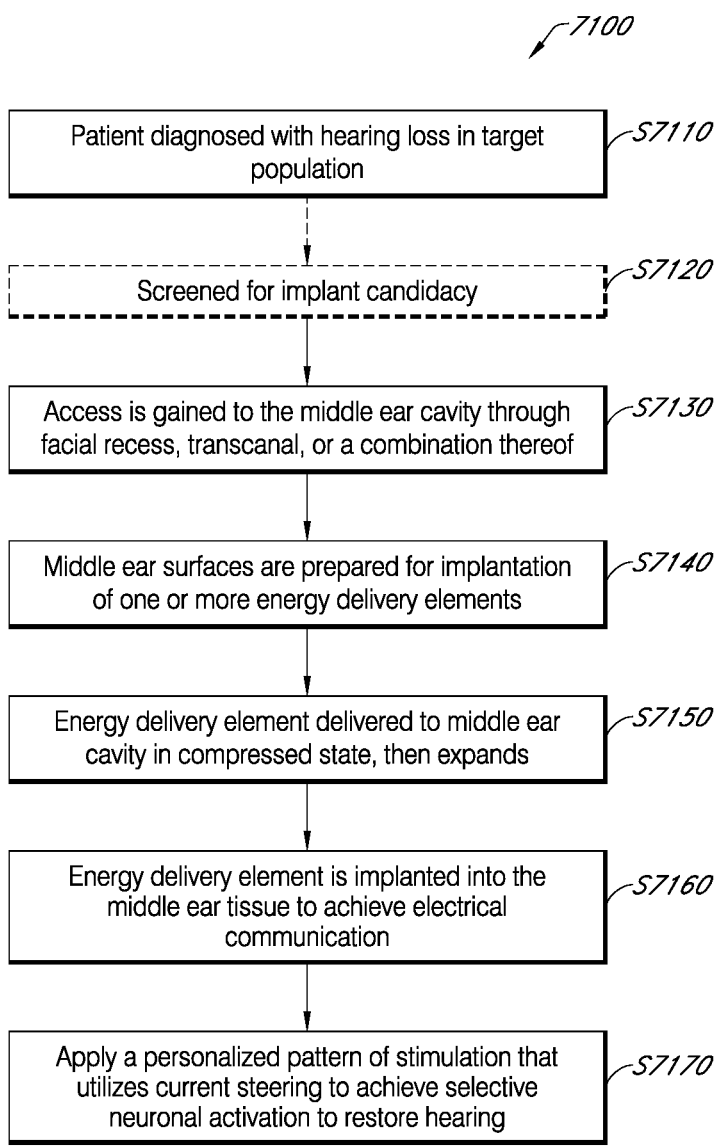
FIG. 71 shows one embodiment of a method of treating a patient having or diagnosed with a hearing condition.

Another method 7100, as shown in FIG. 71, of using or employing any of the devices described herein may include having a patient diagnosed with or having hearing loss in target population at block 57110; optionally (shown in dashed lines), screening the patient for implant candidacy at block 57120; accessing the middle ear cavity through a facial recess, a transcanal, or a combination thereof at block 57130, as described elsewhere herein; preparing one or more middle ear surfaces for implantation of one or more energy delivery elements at block 57140; delivering the one or more energy delivery elements to middle ear cavity in a compressed state, then expanding it (actively) or allowing it to expand (passively) at block S7150; implanting the one or more energy delivery elements into the middle ear tissue to achieve electrical communication at block 57160; and applying a personalized pattern of stimulation that utilizes current steering (e.g., FIGS. 17A-17C) to achieve selective neuronal activation to improve or restore hearing at block 57170. As appreciated by one of skill in the art, any of the method steps may be performed in any order or combined.

In some embodiments, screening comprises performing implant evaluation. Implant evaluation may include pure tone audiometry both unaided and best-aided (with traditional hearing aids) and performing the speech recognition tests in a best-aided condition. This evaluation help determine the criteria that would be includes in the method of treatment.

In some embodiments, the electrical communication that is achieved is long-term. Long-term includes greater than about 30 days; greater than about 60 days; between about 20 days and about 50 days; between about 30 days and about 60 days; etc. or alternatively, for a period greater than a year after an initial 30 to 90 day period of healing after implantation.

In some embodiments, applying a personalized pattern occurs in real-time, on-demand, at a pre-determined interval or frequency, automatically, upon physician request, upon patient request, or a combination thereof. A personalized pattern of electrical stimulation may be based on the patient's hearing loss profile, degree of high-frequency hearing loss, degree of residual low-frequency hearing, or speech recognition scores.

Exemplary Embodiments

One embodiment of an improved device for extracochlear stimulation includes an electrode array configured to integrate with surrounding tissue such that the electrode array maintains electrical communication with the cochlear promontory or round window for more than about 30 days. The electrode array may be configured to have perforations or fenestrations within the body of the array such that tissue can grow into or around the body of the array. The electrode array may comprise features that increase contact area with the underlying tissue such as, but not limited to: roughened surfaces, protrusions, and/or indentations. The electrode array may comprise features that mechanically couple with the underlying tissue such as, but not limited to: hooks, teeth, and/or microneedles. The electrode array may have regions that comprise materials that promote tissue growth such as, but not limited to: growth factors, hydrogels, polymer scaffolds, and/or open cell foams. The electrode array may have regions that comprise materials that prevent or limit tissue growth or regions that have been surface treated to prevent or limit tissue growth. The electrode array may have regions configured for differential tissue growth where different regions promote different degrees of tissue growth. The electrode array may be configured for placement onto the mucosa overlying the cochlear promontory, onto the intact bone of the cochlear promontory, onto the bone of the cochlear promontory that has been prepared using methods described elsewhere within, or onto another tissue of the middle ear near the basal turn of the cochlea. The electrode array may have one or more electrical conductors configured to be placed within the round window niche. The electrode array may have one or more electrical conductors configured to be in contact with the round window membrane. The improved device may also include a microphone, signal processor, stimulator, and receiver/ transmitter.

One embodiment of a method for establishing electrical communication between an electrode array and middle ear tissues includes preparing the tissue and placing an electrode array in physical contact with the prepared tissue. Middle ear tissues may include, but are not limited to: the cochlear promontory, the mucosa overlying the cochlear promontory, the promontory bone, and the round window membrane. Preparing the tissue may include drying the tissue or removing blood or moisture. Preparing the tissue may include removing one or more regions of the mucosa overlying the promontory to reveal the underlying promontory bone. Preparing the tissue may include making lacerations or perforations in the mucosa overlying the promontory bone. Preparing the tissue may include changing the surface of promontory bone with chemical treatments, drilling regions of the cochlear bone, or removing surface layers of the promontory bone. Preparing the tissue may include drilling regions of the round window niche to increase exposure to the round window membrane. The method may include applying pressure to the electrode array after placing the electrode in physical contact with the prepared tissue. Applying pressure may include applying force with the surgical instrument or with surgical packing such as, but not limited to: gel foam. The method may include adhering the electrode array to the prepared tissue using materials such as, but not limited to: cyanoacrylate, hydrogel, fibrin glue, and/or hydroxyapatite. The method may include testing electrical communication between an electrode array and middle ear tissues by measuring the impedance across two electrical conductors of the electrode array that are in contact with tissue. Impedance may be measured using an input signal with frequency of about 1 kHz or between about 10 Hz and about 10 kHz. Sufficient electrical communication may comprise having impedance value less than about 50 kΩ, or in some cases less than about 30 kΩ, or in some cases less than about 20 kΩ, or in some cases less than about 10 kΩ, or in some cases less than about 5 kΩ.

One embodiment of an improved device for extracochlear stimulation includes an electrode array configured to conform to the natural anatomy of the middle ear cavity. The electrode array may be made of a flexible substrate such as, but not limited to: silicone, urethane, a silicone-urethane composite, polyimide, and/or nitinol wire. The electrode array may have a thickness between about 0.01 mm and about 1 mm, or between about 0.01 mm and about 0.5 mm, or between about 0.01 mm and about 0.3 mm, or between about 0.01 mm and about 0.1 mm, or between about 0.05 mm and about 0.5 mm, or between about 0.1 mm and about 0.5 mm, or between about 0.1 mm and about 0.3 mm where the thickness may be chosen to optimize the flexibility of the electrode array. The electrode array may have perforations or fenestrations configured to increase the flexibility of the entire array or configured to create different degrees of flexibility in different regions of the array. The size of the perforations or fenestrations may be chosen such that the open area of the electrode array is between about 20% and about 99%, or between about 40% and about 99%, or between about 60% and about 99%, or between about 80% and about 99%, or between about 60% and about 95%, or between about 80% and about 95% where the open area may be chosen to optimize the flexibility of the electrode array. The electrode array may comprise a mesh-like structure with individual electrical conductors connected together with nitinol wire. The electrode array may be sized to fit within the middle ear cavity. The longitudinal axis of the array is defined by the path from the round window to the eustachian tube. The longitudinal dimension of the electrode array may be between about 1 mm and about 15 mm, or between about 1 mm and about 12 mm, or between about 1 mm and about 10 mm, or between about 1 mm and about 8 mm, or between about 3 mm and about 12 mm, or between about 3 mm and about 10 mm, or between about 3 mm and about 8 mm. The transverse axis of the electrode array is defined as the axis perpendicular to the longitudinal axis along the surface of the cochlear promontory. The transverse dimension of the electrode array may be between about 1 mm and about 10 mm, or between about 1 mm and about 8 mm, or between about 1 mm and about 6 mm, or between about 1 mm and about 4 mm, or between about 2 mm and about 10 mm, or between about 2 mm and about 8 mm, or between about 2 mm and about 6 mm. The electrode array may taper along the longitudinal axis such that the transverse measurement is larger near the round window and smaller near the Eustachian tube. The electrode array may have projections from the main body of the array which are configured to contact additional structures in the middle ear including, but not limited to: the round window, the round window membrane, the eustachian tube orifice, the hypotympanum, the epitympanum, the stapes footplate, the facial recess, the tympanic membrane, or the distal wall of the middle ear cavity. The projects may not have a fixed length and may be lengthened or shortened in order to contact the target tissue. The electrode array may have one or more notches within the body of the array to allow the array to bend or twist in a predefined direction. The electrode may be compressible and may be delivered in a compressed state and may be expanded to a second configuration within the middle ear cavity. The electrode may be delivered to the middle ear cavity through the facial recess or may be delivered through a minimally invasive transcanal approach or may be delivered through a combination of both approaches. The electrode array may have features that allow for blind placement through the facial recess. The electrode array may have redundancy in electrodes such that not all electrodes need to be in contact with tissues of the middle ear cavity in order for the device to be fully functional. The electrode array may have individual contacts that are arranged such that they may be positioned longitudinally along the basal turn of the cochlea. The electrode array may have individual contacts that are arranged such that individual electrodes are positioned inferiorly and superiorly to the basal turn of the cochlea. The electrode array may have individual contacts that are arranged such that individual electrodes are positioned anteriorly and posteriorly to the basal turn of the cochlea. The electrode array may have individual contacts arranged to optimize the ability to perform current steering or to shape the electric field to target specific auditory neurons.

One embodiment of a method for improving speech understanding includes delivering electrical stimulation signals to auditory nerves using an extracochlear electrode array configured to be implanted within the middle ear cavity without penetrating the lumen of the cochlea. The electrical stimulation signals may be configured to selectively stimulate auditory nerves at the basal turn of the cochlea. The electrical stimulation signals may be configured to selectively stimulate the region of the cochlea responsible for perception of about 1 kHz to about 8 kHz hearing, or in some cases about 1.5 kHz to about 8 kHz hearing, or in some cases about 2 kHz to about 8 kHz hearing, or in some cases about 1 kHz to about 6 kHz hearing, or in some cases about 1.5 kHz to about 6 kHz hearing, or in some cases about 2 kHz to about 6 kHz hearing. The electrical stimulation signals may be configured to improve or restore high-frequency hearing in the patient, such that the patient has improved speech understanding and substantially preserved residual hearing. The electrical stimulation signals may be configured to selectively stimulate auditory neurons in order to create the perception of speech sounds that are difficult for the patient to distinguish such as, but not limited to: the consonant sounds "k", "f", "s", and "sh". The method may include collecting sound signals at one or more sound input devices. The method may include generating electrical stimulation signals representative of the sound signals in a sound processor. The method may include separating sound signals based on a frequency threshold of about 1 kHz or about 1.5 kHz or about 2 kHz and generating electrical stimulation signals representative of the sound signals higher than the frequency threshold in a sound processor. The method may include acoustically amplifying the sound signals lower than the frequency threshold. The method may include implanting an electrode array within a middle ear cavity wherein the electrode array is in electrical communication with one or more surfaces comprising of: a cochlear promontory, a mucosa overlying a cochlear promontory, a hypotympanum, an epitympanum, a medial aspect of an opening to a Eustachian tube, a round window membrane or niche, or a combination thereof. The method may include implanting an electrode array in the round window niche such that the electrode array is not in contact with the round window membrane in order to prevent disrupting the natural movement of the membrane or to prevent diminishing residual hearing. The electrode array may comprise one or more electrical conductors.

One embodiment of a method for improving speech understanding includes delivering electrical stimulation signals to auditory nerves using an extracochlear electrode array configured to be implanted within the middle ear cavity without penetrating the lumen of the cochlea. The electrical stimulation signals may be configured to provide high-frequency sound information to the patient, such that the patient has improved speech understanding and substantially preserved residual hearing. The electrical stimulation signals may be configured to selectively stimulate auditory neurons in order to create the perception of speech sounds that are difficult for the patient to distinguish such as, but not limited to: the consonant sounds "k", "f", "s", and "sh". The method may include collecting sound signals at one or more sound input devices. The method may include generating electrical stimulation signals representative of the sound signals in a sound processor. The method may include separating sound signals based on a frequency threshold of about 1 kHz or about 1.5 kHz or about 2 kHz and generating electrical stimulation signals representative of the sound signals higher than the frequency threshold in a sound processor. The method may include generating electrical stimulation signals representative of specific speech sounds that the patient is unable to distinguish such as, but not limited to: the consonant sounds "k", "f", "s", and "sh". The method may include creating a unique pattern of electrical stimulation signals for specific speech sounds that does not necessarily create the perception of a particular high-frequency sound but allows a patient to distinguish speech sounds based on the unique pattern. The electrical stimulation signals may be temporally modulated, frequency modulated, or amplitude modulated in order to create a unique pattern representative of speech sounds. The method may include delivering electrical stimulation signals to provide supplementary speech information that may be perceived in combination with acoustic hearing to improve speech understanding. The method may be appropriate for patients with high frequency hearing loss who only benefit from a limited number of extracochlear electrodes, which can be used for high frequency information encoding. The method may include identifying and extracting in real-time, important features of speech in the high frequencies, for example from the "speech banana", sounds such as "c", "f", "ch", "sh", using a speech processor. The method may then include translating these speech features into patterns of stimulation that can be distinguished by a patient even solely by their temporal stimulation characteristics even through a single extracochlear electrode. The method may involve the patient adapting to this new type of auditory stimulus encoding over months of use of the device during which time their speech understanding would improve. The method may include acoustically amplifying the sound signals lower than the frequency threshold. The method may include implanting an electrode array within a middle ear cavity wherein the electrode array is in electrical communication with one or more surfaces comprising of: a cochlear promontory, a mucosa overlying a cochlear promontory, a hypotympanum, an epitympanum, a medial aspect of an opening to a Eustachian tube, a round window membrane or niche, or a combination thereof. The method may include implanting an electrode array in the round window niche such that the electrode array is not in contact with the round window membrane in order to prevent disrupting the natural movement of the membrane or to prevent diminishing residual hearing. The electrode array may comprise one or more electrical conductors.

One embodiment of a system to improve speech understanding in a patient with high frequency hearing loss may comprise a flexible silicone electrode array with many substrate perforations interspersed throughout the array to allow for both greater conformability of the array to the promontory and middle ear surfaces and also to allow mucosal overgrowth and tissue integration after implantation. The envelope of the electrode array may be shaped to avoid the stapes footplate and designed to follow the longitudinal axis of the basal turn of the cochlea underlying the promontory bone in order for the surface electrodes to target different neuron populations along the high frequency region of the cochlea. In addition to the electrode array there may be an electrode specifically designed to maintain electrical contact with the round window membrane while not disturbing the free movement of the membrane. The electrode array and round window electrode may be delivered in a compressed state through a minimally invasive facial recess surgical approach to the middle ear. Once delivered to the middle ear cavity, the electrodes could be decompressed allowing the surgeon to position them and temporarily affix them to the middle ear surfaces using an adhesive capable of holding the electrodes in place until tissue integration occurred. The electrodes may be connected to the implantable stimulator receiver by two leads, angulated to minimize strain between the electrode surface and the round window aperture. The implantable stimulator receiver may be positioned under the skin behind the ear with a coil and alignment magnet to align and communicate with an externally worn component that would include the battery, signal processor and microphones.

One embodiment of a method for securing an electrode in an ear of a subject, includes: inserting an electrode array into a middle ear cavity and proximate an external surface of a cochlea of the subject; applying pressure to the electrode array against the external surface of the cochlea; and attaching the electrode array to the external surface of the cochlea while the pressure is applied.

In any of the preceding embodiments, the method may further comprise measuring electrical contact between the electrode array and the external surface of the cochlea before attaching the electrode array to the external surface of the cochlea. In any of the preceding embodiments, the method may further comprise temporarily attaching the electrode array to the external surface of the cochlea. In any of the preceding embodiments, the method may further comprise applying one or more adhesives to one or both of the electrode array or the external surface of the cochlea In any of the preceding embodiments, the one or more adhesives comprise one or more of: bone wax, bone cement, fibrin glue, or cyanoacrylate. In any of the preceding embodiments, the method may further comprise preparing the external surface of the cochlea prior to attachment of the electrode array. In any of the preceding embodiments, the method may further comprise preparing comprises one or more of: disrupting mucosa on the external surface of the cochlea, applying an acid to the external surface of the cochlea, at least partially drying the external surface of the cochlea, or applying a tissue growth factor to the external surface of the cochlea. In any of the preceding embodiments, attaching the electrode array to the external surface of the cochlea comprises introducing a scaffold into the middle ear cavity to promote attachment of the electrode array to the external surface of the cochlea. In any of the preceding embodiments, the scaffold comprises one or more of: fibrin glue or gelatin sponge. In any of the preceding embodiments, the method may further comprise preparing the electrode array prior to insertion. In any of the preceding embodiments, preparing comprises determining or creating a size of the electrode array based on a size of the cochlea. In any of the preceding embodiments, attachment comprises one or more of: attaching using an adhesive, attaching by promoting tissue ingrowth into at least a portion of the electrode array, fixing the electrode array to the external surface using one or more mechanical anchors, or suctioning the electrode array to the external surface. In any of the preceding embodiments, attaching comprises applying an adhesive, and curing the adhesive using one or more of: ultraviolet light, heat, or an accelerant. In any of the preceding embodiments, applying pressure further comprises inserting a balloon into the middle ear cavity and inflating the balloon to apply pressure to the electrode array against the external surface of the cochlea. In any of the preceding embodiments, applying pressure further comprises inserting one or more springs or posts into the middle ear cavity, such that the one or more springs or posts apply pressure to the electrode array against the external surface of the cochlea. In any of the preceding embodiments, applying pressure further comprises inserting a tool into the middle ear cavity to apply pressure to the electrode array against the external surface of the cochlea. In any of the preceding embodiments, applying pressure further comprises inserting a deformable material into the middle ear cavity. In any of the preceding embodiments, during insertion, the deformable material has a first unexpanded configuration. In any of the preceding embodiments, once positioned in the middle ear cavity, the deformable material has a second expanded configuration, such that the deformable material applies pressure to the electrode array in the second expanded configuration. In any of the preceding embodiments, the external surface of the cochlea corresponds to a basal turn of the cochlea. In any of the preceding embodiments, the method may further comprise electrically stimulating neurons in the cochlea to effect hearing in the subject. In any of the preceding embodiments, the method may further comprise selectively stimulating the neurons in the cochlea to effect high frequency hearing in the subject. In any of the preceding embodiments, selectively stimulating comprises personalizing the selective stimulation based on one or more of: feedback from the subject, an anatomy of the subject, a psychoacoustic testing of the subject, brain activity, imaging data, impedance values, or electrically elicited compound action potential data. In any of the preceding embodiments, inserting comprises advancing the electrode array through an external auditory canal, past the tympanic membrane and into the middle ear cavity. In any of the preceding embodiments, inserting comprises advancing the electrode array through a surgically created canal through a temporal bone of the subject. In any of the preceding embodiments, the electrode array is further manipulated through an external auditory canal, past the tympanic membrane either under direct visualization or using a microscope or endoscope. In any of the preceding embodiments, inserting comprises advancing the electrode array through a nasopharynx through a eustachian tube into the middle ear cavity. In any of the preceding embodiments, the method may further comprise releasing the pressure on the electrode array once the electrode array is attached.

One embodiment of an energy delivery element configured for attachment to a bony surface of a subject, comprises: a substrate; and a plurality of electrodes disposed in or on the substrate, such that each electrode comprises an electrical contact, such that stimuli can be delivered to both all or a subset of the plurality of electrodes.

In any of the preceding embodiments, the bony surface is a promontory of a cochlea of the subject. In any of the preceding embodiments, the substrate is configured to conform to the promontory of the cochlea. In any of the preceding embodiments, an arrangement of the plurality of electrodes is configured to selectively stimulate neurons in the cochlea that are associated with high frequency hearing. In any of the preceding embodiments, at least a subset of the plurality of electrodes comprises a bone adhesion promoting coating. In any of the preceding embodiments, the substrate defines one or more perforations or apertures to promote tissue ingrowth. In any of the preceding embodiments, the one or more perforations or apertures are coated with a tissue growth promoting factor. In any of the preceding embodiments, a body of the substrate defines one or more perforations or apertures to promote tissue ingrowth. In any of the preceding embodiments, a portion of a perimeter of the substrate defines one or more perforations or apertures to promote tissue ingrowth. In any of the preceding embodiments, the substrate comprises one or more barbed protrusions to couple the array to the bony surface. In any of the preceding embodiments, the one or more barbed protrusions are coated with a tissue growth promoting factor. In any of the preceding embodiments, a portion of a perimeter of the substrate comprises one or more barbed protrusions to couple the array to the bony surface. In any of the preceding embodiments, a body of the substrate comprises one or more barbed protrusions to couple the array to the bony surface. In any of the preceding embodiments, the substrate defines one or more microfluidic channels. In any of the preceding embodiments, the one or more microfluidic channels are configured to be filled with one or more of: an adhesive, a tissue growth promoting factor, an acid, or an accelerant. In any of the preceding embodiments, the element further comprises a housing defining an injection port, such that the housing is configured to be positioned at least partially over or around the substrate and retain an adhesive that is injected through the injection port to adhere the substrate to the bony surface. In any of the preceding embodiments, the element further comprises a housing that is configured to be positioned at least partially over or around the substrate and retain an adhesive for adhering the substrate to the bony surface. In any of the preceding embodiments, the substrate is flexible. In any of the preceding embodiments, the substrate comprises at least one elastomer. In any of the preceding embodiments, the substrate comprises one or both of: polydimethylsiloxane (PDMS) or silicone. In any of the preceding embodiments, the substrate comprises a mesh. In any of the preceding embodiments, the substrate comprises a rigid substrate. In any of the preceding embodiments, the substrate comprises one or more of: a printed circuit board, a complementary metal-oxide-semiconductor (CMOS) chip, polycarbonate, or acrylic. In any of the preceding embodiments, the plurality of electrodes comprises one or more of: spring probes, leaf springs, or spring coils. In any of the preceding embodiments, the substrate has a delivery conformation having a cross-sectional area of less than about 200 mm². In any of the preceding embodiments, the electrode array is communicatively coupled to: a stimulator/receiver; a transmitter; a microphone; a power source; and a processing unit. In any of the preceding embodiments, the device further comprises an acoustic amplifier electrically coupled to the processing unit and configured to amplify low frequency sounds. In any of the preceding embodiments, communicatively coupled comprises a wired connection. In any of the preceding embodiments, the device further comprises a base defining an aperture, the base being secured to the cochlea such that the substrate is coupled to the base and the plurality of electrodes extend through the aperture and contact the promontory of the cochlea. In any of the preceding embodiments, the device further comprises one or more return electrodes. In any of the preceding embodiments, the substrate comprises a conformable wire, such that the wire has a substantially linear delivery configuration and a substantially coiled stimulation configuration. In any of the preceding embodiments, the device further comprises one or more tethers coupled to the substrate, wherein the one or more tethers are configured to contact or anchor to a surface of a middle ear cavity to apply pressure to the substrate against the cochlea. In any of the preceding embodiments, the device further comprises one or more mechanical anchors to secure the substrate to the bony surface.

One embodiment of a method for securing an electrode in an ear of a subject, comprises: inserting an electrode array into a middle ear cavity; positioning the electrode array on an external surface of a cochlea; and attaching the electrode array to the external surface of the cochlea. In any of the preceding embodiments, attaching comprises applying pressure to the electrode array against the external surface of the cochlea. In any of the preceding embodiments, applying pressure further comprises inserting a balloon into the middle ear cavity and inflating the balloon to apply pressure to the electrode array against the external surface of the cochlea. In any of the preceding embodiments, applying pressure further comprises inserting one or more springs or posts into the middle ear cavity, such that the one or more springs or posts apply pressure to the electrode array against the external surface of the cochlea. In any of the preceding embodiments, applying pressure further comprises inserting a tool into the middle ear cavity to apply pressure to the electrode array against the external surface of the cochlea. In any of the preceding embodiments, the device further comprises applying pressure further comprises inserting a deformable material into the middle ear cavity. In any of the preceding embodiments, wherein during insertion, the deformable material has a first unexpanded configuration. In any of the preceding embodiments, wherein, once positioned in the middle ear cavity, the deformable material has a second expanded configuration, such that the deformable material applies pressure to the electrode array in the second expanded configuration.

One embodiment of a method for treating high frequency hearing loss in a subject in need thereof, comprises: inserting an electrode array into a middle ear cavity; positioning the electrode array on an external surface of a cochlea; and attaching the electrode array to the external surface of the cochlea while the pressure is applied.

One embodiment of a method for securing an electrode in an ear of a subject, comprises: inserting an electrode array into a middle ear cavity; positioning the electrode array on an external surface of a cochlea; attaching the electrode array to the external surface of the cochlea while the pressure is applied; and selectively stimulating neurons in the cochlea to effect high frequency hearing in the subject.

One embodiment of an electrode array configured for attachment to a bony surface comprising a promontory bone or a mucosa overlying the promontory bone of a subject, comprises: a substrate comprising: a body having a top side and a bottom side, wherein the bottom side is configured to contact the bony surface when inserted into a middle ear cavity of a patient, and one or more perforations defined by the body, wherein the perforations extend through the body from the top side to the bottom side; and a plurality of electrodes disposed in or on the substrate but not overlapping with the one or more perforations, such that each electrode comprises an electrical contact, such that stimuli can be delivered to both all or a subset of the plurality of electrodes.

In any of the preceding embodiments, the body of the substrate is surrounded by a perimeter, such that at least a portion of the perimeter comprises a raised edge. In any of the preceding embodiments, the raised edge is substantially perpendicular to the body of the substrate. In any of the preceding embodiments, the raised edge is at an angle of about 30 degrees to about 120 degrees relative to the body of the substrate. In any of the preceding embodiments, the perimeter further comprises a concave section to accommodate one or more anatomical structures in the middle ear cavity. In any of the preceding embodiments, the device further comprises a lead that is electrically coupled to the electrode array. In any of the preceding embodiments, the device further comprises an implanted stimulator electrically coupled to the lead, wherein the implanted stimulator is external to the middle ear cavity but implanted subcutaneously.

One embodiment of a method of implanting an electrode array in a middle ear cavity of a subject, the method comprises: minimally preparing a promontory bone of a cochlea of a patient; inserting an electrode array into a middle ear cavity, wherein the electrode array comprises a substrate comprising a body have a top side and a bottom side, such that the body defines one or more perforations that extend through the body from the top side to the bottom side; positioning the electrode array on an external surface of a basal turn of the cochlea; and applying adhesive to the one or more perforations, such that the adhesive at least partially flows from the top side to the bottom side of the body to adhere the array to the cochlea.

In any of the preceding embodiments, the method further comprises temporarily applying pressure to the electrode array to allow curing of the adhesive. In any of the preceding embodiments, applying pressure further comprises inserting a balloon into the middle ear cavity and inflating the balloon to apply pressure to the electrode array against the cochlea. In any of the preceding embodiments, applying pressure further comprises inserting one or more springs or posts into the middle ear cavity, such that the one or more springs or posts apply pressure to the electrode array against the cochlea. In any of the preceding embodiments, applying pressure further comprises inserting a tool into the middle ear cavity to apply pressure to the electrode array against the cochlea. In any of the preceding embodiments, applying pressure further comprises inserting a deformable material into the middle ear cavity. In any of the preceding embodiments, wherein during insertion, the deformable material has a first unexpanded configuration. In any of the preceding embodiments, wherein, once positioned in the middle ear cavity, the deformable material has a second expanded configuration, such that the deformable material applies pressure to the electrode array in the second expanded configuration. In any of the preceding embodiments, inserting further comprises inserting the array into the middle ear cavity through a facial recess of a temporal bone of the patient. In any of the preceding embodiments, the method further comprises positioning a lead electrically coupled to the array in the facial recess. In any of the preceding embodiments, inserting further comprises inserting the array through a transcanal pathway. In any of the preceding embodiments, the method further comprises positioning a lead electrically coupled to the array subcutaneously along an ear canal of the patient. In any of the preceding embodiments, the method further comprises curing the adhesive using one or more of: ultraviolet light, heat, an accelerant, or laser light. In any of the preceding embodiments, the method further comprises selectively stimulating neurons in the cochlea to effect high frequency hearing in the patient. In any of the preceding embodiments, minimally preparing comprises one or more of: disrupting mucosa on an external surface of the cochlea, applying an acid to the external surface of the cochlea, at least partially drying the external surface of the cochlea, or applying a tissue growth factor to the external surface of the cochlea. In any of the preceding embodiments, the substrate of the array further comprises a perimeter surrounding the body, and wherein the perimeter comprises a concave section. In any of the preceding embodiments, positioning comprises positioning the concave section proximal to a stapes footplate so that the array avoids the stapes footplate. In any of the preceding embodiments, the perimeter further comprises a raised edge that is configured to prevent adhesive flowing to or interacting with a stapes footplate. In any of the preceding embodiments, the raised edge is substantially perpendicular to the body of the substrate.

One embodiment of a method for treating a patient diagnosed with at least severe high-frequency sensorineural hearing loss with residual low-frequency hearing, comprises: implanting one or more energy delivery elements within a middle ear cavity, wherein the one or more electrical conductors are in electrical communication with one or more tissues in the middle ear cavity; delivering electrical stimulation to activate a spiral ganglion of a basal turn of a cochlea, the electrical stimulation driven by external acoustic stimuli sensed by a microphone; and improving high-frequency hearing in the patient, such that the patient has improved speech understanding and substantially preserved residual hearing.

In any of the preceding embodiments, the one or more tissues comprise one of: a cochlear promontory, a mucosa overlying a cochlear promontory, a hypotympanum, an epitympanum, a medial aspect of an opening to a Eustachian tube, a round window membrane or niche, or a combination thereof. In any of the preceding embodiments, implanting occurs without penetrating a lumen of the cochlea. In any of the preceding embodiments, the electrical stimulation comprises active electrical stimulation. In any of the preceding embodiments, improving high frequency hearing comprising improving hearing in a frequency range of about 2 kHz to about 8 kHz. In any of the preceding embodiments, the severe-to-profound hearing loss comprises having pure tone audiometric thresholds greater than about 70 dB in a frequency range of about 2 kHz to about 8 kHz. In any of the preceding embodiments, the residual low-frequency hearing comprises having pure tone audiometric thresholds lower than about 70 dB in a frequency range of about 125 Hz to about 500 Hz. In any of the preceding embodiments, before electrical stimulation, the patient is further characterized as having an impaired ability to understand speech as measured by one or more standardized tests. In any of the preceding embodiments, the one or more standardized tests comprise: AzBio test, a CNC words test, a CNC sentences test, or a HINT Sentences in Noise and Quiet test, all with varying background noise. In any of the preceding embodiments, the impaired ability to understand speech comprises scoring lower than about 60% correct on the one or more standardized tests. In any of the preceding embodiments, before electrical stimulation, the patient is characterized as no longer substantially benefitting from acoustic amplification of high frequencies in a frequency range of about 2 kHz to about 8 kHz. In any of the preceding embodiments, implanting comprises implanting an energy delivery element that comprises the one or more electrical conductors, the energy delivery element being connected to an implanted stimulator which is in wireless communication with a signal processor and the microphone. In any of the preceding embodiments, the method further comprises surgically accessing the middle ear cavity through one of: a facial recess approach, a transcanal approach, or a combination thereof. In any of the preceding embodiments, the facial recess approach comprises advancing the energy delivery element through a surgically created canal through a temporal bone of the patient. In any of the preceding embodiments, the transcanal approach comprises advancing the energy delivery element through or alongside an external auditory canal, past a tympanic membrane, and into the middle ear cavity. In any of the preceding embodiments, the combination thereof comprises delivering the energy delivery element through the facial recess and further manipulating the energy delivery element through an external auditory canal. In any of the preceding embodiments, the further manipulation occurs under direct visualization. In any of the preceding embodiments, the further manipulation occurs using a microscope or an endoscope. In any of the preceding embodiments, the combination thereof comprises reducing facial recess exposure to reduce a likelihood of facial nerve injury. In any of the preceding embodiments, the combination thereof comprises delivering the energy delivery element to the middle ear cavity in a compressed configuration. In any of the preceding embodiments, the method further comprises preparing the one or more tissues of the middle ear cavity for implantation of the one or more energy delivery elements. In any of the preceding embodiments, the method further comprises maintaining chronic electrical contact between the one or more energy delivery elements and the one or more tissues. In any of the preceding embodiments, chronic electrical contact comprises contact for greater than about 30 days. In any of the preceding embodiments, preparing the one or more tissues comprises disrupting a mucosa on an external surface of the cochlea. In any of the preceding embodiments, preparing the one or more tissues comprises applying an acid to an external surface of the cochlea. In any of the preceding embodiments, preparing the one or more tissues comprises applying a sclerosing agent to promote accelerated adhesion of mucosa to the one or more electrical conductors. In any of the preceding embodiments, preparing the one or more tissues comprises at least partially drying an external surface of the cochlea. In any of the preceding embodiments, preparing the one or more tissues comprises applying a tissue growth factor to an external surface of the cochlea. In any of the preceding embodiments, the method further comprises delivering an electrode array comprising the one or more energy delivery elements through the facial recess approach in a compressed configuration and expanding the electrode array into an expanded configuration in the middle ear cavity. In any of the preceding embodiments, the method further comprises delivering an electrode array comprising the one or more energy delivery elements through an external auditory canal in a compressed configuration and expanding the electrode array into an expanded configuration in the middle ear cavity. In any of the preceding embodiments, implanting the one or more energy delivery elements comprises reversibly implanting the one or more energy delivery elements. In any of the preceding embodiments, implanting comprises positioning the one or more energy delivery elements on the one or more tissues of the middle ear cavity. In any of the preceding embodiments, implanting comprises establishing electrical communication between the one or more energy delivery elements and the one or more tissues of the middle ear cavity. In any of the preceding embodiments, establishing electrical communication comprises adhesively attaching the one or more energy delivery elements to the one or more tissues. In any of the preceding embodiments, adhesively attaching comprises applying one or more of: a bone wax, a bone cement, a fibrin glue, a cyanoacrylate, or a combination thereof. In any of the preceding embodiments, establishing electrical communication comprises applying mechanical force to the one or more energy delivery elements against the one or more tissues. In any of the preceding embodiments, establishing electrical communication comprises promoting tissue integration of the one or more tissues with the one or more energy delivery elements. In any of the preceding embodiments, establishing electrical communication comprises mechanical attaching the one or more energy delivery elements to the one or more tissues. In any of the preceding embodiments, the mechanical attachment comprises a temporary attachment. In any of the preceding embodiments, the method further comprises confirming electrical communication between the one or more energy delivery elements and the one or more tissues with impedance measurements. In any of the preceding embodiments, implanting comprises maintaining electrical communication between the one or more energy delivery elements and the one or more tissues of the middle ear cavity. In any of the preceding embodiments, delivering electrical stimulation comprises current steering with two or more energy delivery elements. In any of the preceding embodiments, current steering comprises shaping an electric field delivered by the electrical stimulation to target specific neurons within the basal turn of the cochlea. In any of the preceding embodiments, the method further comprises individualizing the electrical stimulation by mapping a position of the one or more energy delivery elements to a tonotopicity of the basal turn of the cochlea of the patient. In any of the preceding embodiments, electrical communication comprises physical contact with the one or more tissues. In any of the preceding embodiments, the external acoustic stimuli comprise sounds sensed by a microphone and processed by a processor. In any of the preceding embodiments, the one or more energy delivery elements comprise an electrode array or one or more electrodes.

One embodiment of a method for treating a patient having at least severe high-frequency sensorineural hearing loss and residual low-frequency hearing, comprises: implanting one or more energy delivery elements within a middle ear cavity, wherein the one or more electrical conductors are in electrical communication with one or more tissues in the middle ear cavity; delivering electrical stimulation to activate a spiral ganglion of a basal turn of a cochlea, the electrical stimulation driven by external acoustic stimuli sensed by a microphone; and improving high-frequency hearing in the patient, such that the patient has improved speech understanding and substantially preserved residual hearing.

In any of the preceding embodiments, the one or more tissues comprise one of: a cochlear promontory, a mucosa overlying a cochlear promontory, a hypotympanum, a medial aspect of an opening to a Eustachian tube, a round window membrane and niche, or a combination thereof. In any of the preceding embodiments, implanting occurs without penetrating a lumen of the cochlea. In any of the preceding embodiments, the electrical stimulation comprises active electrical stimulation. In any of the preceding embodiments, improving high frequency hearing comprising improving hearing in a frequency range of about 2 kHz to about 8 kHz. In any of the preceding embodiments, the severe-to-profound hearing loss comprises having pure tone audiometric thresholds greater than about 70 dB in a frequency range of about 2 kHz to about 8 kHz. In any of the preceding embodiments, the residual low-frequency hearing comprises having pure tone audiometric thresholds lower than about 70 dB in a frequency range of about 125 Hz to about 500 Hz. In any of the preceding embodiments, before electrical stimulation, the patient is further characterized as having an impaired ability to understand speech as measured by one or more standardized tests. In any of the preceding embodiments, the one or more standardized tests comprise: AzBio test, a CNC words test, a CNC sentences test, or a HINT Sentences in Noise and Quiet test. In any of the preceding embodiments, the impaired ability to understand speech comprises scoring lower than about 60% correct on the one or more standardized tests. In any of the preceding embodiments, before electrical stimulation, the patient is characterized as no longer substantially benefitting from acoustic amplification of high frequencies in a frequency range of about 2 kHz to about 8 kHz. In any of the preceding embodiments, implanting comprises implanting an energy delivery element that comprises the one or more electrical conductors, the energy delivery element being connected to an implanted stimulator which is in wireless communication with a signal processor and the microphone. In any of the preceding embodiments, the method further comprises surgically accessing the middle ear cavity through one of: a facial recess approach, a transcanal approach, or a combination thereof. In any of the preceding embodiments, the facial recess approach comprises advancing the energy delivery element through a surgically created canal through a temporal bone of the patient. In any of the preceding embodiments, the transcanal approach comprises advancing the energy delivery element through or alongside an external auditory canal, past a tympanic membrane, and into the middle ear cavity. In any of the preceding embodiments, the combination thereof comprises delivering the energy delivery element through the facial recess and further manipulating the energy delivery element through an external auditory canal. In any of the preceding embodiments, the further manipulation occurs under direct visualization. In any of the preceding embodiments, the further manipulation occurs using a microscope or an endoscope. In any of the preceding embodiments, the combination thereof comprises reducing facial recess exposure to reduce a likelihood of facial nerve injury. In any of the preceding embodiments, the combination thereof comprises delivering the energy delivery element to the middle ear cavity in a compressed configuration. In any of the preceding embodiments, the method further comprises preparing the one or more tissues of the middle ear cavity for implantation of the one or more energy delivery elements. In any of the preceding embodiments, the method further comprises maintaining chronic electrical contact between the one or more energy delivery elements and the one or more tissues. In any of the preceding embodiments, chronic electrical contact comprises contact for greater than about 30 days. In any of the preceding embodiments, preparing the one or more tissues comprises disrupting a mucosa on an external surface of the cochlea. In any of the preceding embodiments, preparing the one or more tissues comprises applying an acid to an external surface of the cochlea. In any of the preceding embodiments, preparing the one or more tissues comprises applying a sclerosing agent to promote accelerated adhesion of mucosa to the one or more electrical conductors. In any of the preceding embodiments, preparing the one or more tissues comprises at least partially drying an external surface of the cochlea. In any of the preceding embodiments, preparing the one or more tissues comprises applying a tissue growth factor to an external surface of the cochlea. In any of the preceding embodiments, the method further comprises delivering an electrode array comprising the one or more energy delivery elements through the facial recess approach in a compressed configuration and expanding the electrode array into an expanded configuration in the middle ear cavity. In any of the preceding embodiments, the method further comprises delivering an electrode array comprising the one or more energy delivery elements through an external auditory canal in a compressed configuration and expanding the electrode array into an expanded configuration in the middle ear cavity. In any of the preceding embodiments, implanting the one or more energy delivery elements comprises reversibly implanting the one or more energy delivery elements. In any of the preceding embodiments, implanting comprises positioning the one or more energy delivery elements on the one or more tissues of the middle ear cavity. In any of the preceding embodiments, implanting comprises establishing electrical communication between the one or more energy delivery elements and the one or more tissues of the middle ear cavity. In any of the preceding embodiments, establishing electrical communication comprises adhesively attaching the one or more energy delivery elements to the one or more tissues. In any of the preceding embodiments, adhesively attaching comprises applying one or more of: a bone wax, a bone cement, a fibrin glue, a cyanoacrylate, or a combination thereof. In any of the preceding embodiments, establishing electrical communication comprises applying mechanical force to the one or more energy delivery elements against the one or more tissues. In any of the preceding embodiments, establishing electrical communication comprises promoting tissue integration of the one or more tissues with the one or more energy delivery elements. In any of the preceding embodiments, establishing electrical communication comprises mechanical attaching the one or more energy delivery elements to the one or more tissues. In any of the preceding embodiments, the mechanical attachment comprises a temporary attachment. In any of the preceding embodiments, the method further comprising confirming electrical communication between the one or more energy delivery elements and the one or more tissues with impedance measurements. In any of the preceding embodiments, implanting comprises maintaining electrical communication between the one or more energy delivery elements and the one or more tissues of the middle ear cavity. In any of the preceding embodiments, delivering electrical stimulation comprises current steering with two or more energy delivery elements. In any of the preceding embodiments, current steering comprises shaping an electric field delivered by the electrical stimulation to target specific neurons within the basal turn of the cochlea. In any of the preceding embodiments, the method further comprising individualizing the electrical stimulation by mapping a position of the one or more energy delivery elements to a tonotopicity of the basal turn of the cochlea of the patient. In any of the preceding embodiments, electrical communication comprises physical contact with the one or more tissues. In any of the preceding embodiments, the external acoustic stimuli comprise sounds sensed by a microphone and processed by a processor. In any of the preceding embodiments, the one or more energy delivery elements comprise an electrode array or one or more electrodes.

One embodiment of an energy delivery element for stimulating a spiral ganglion of a cochlea from a middle ear cavity comprises: a flexible substrate configured to conform to a curvature of one or more of: a cochlear promontory, one or more projections of a hypotympanum, a cavity within a round window niche, or a combination thereof within a middle ear cavity; one or more electrical contacts coupled to the substrate and configured to deliver electrical stimuli to activate a spiral ganglion of a basal turn of a cochlea; and one or more perforations defined by the flexible substrate and configured to promote long-term electrical contact with one or more of: the cochlear promontory, the one or more projections of the hypotympanum, the cavity within the round window niche, or the combination thereof within the middle ear cavity.

In any of the preceding embodiments, long-term electrical contact comprises at least about 30 days. In any of the preceding embodiments, long-term electrical contact comprises about 30 days to about one year. In any of the preceding embodiments, a thickness of the flexible substrate is less than about 0.5 mm. In any of the preceding embodiments, the one or more electrical contacts are configured to deliver electrical stimuli individually. In any of the preceding embodiments, the one or more electrical contacts are configured to deliver electrical stimuli in combination with one or more other electrical contacts. In any of the preceding embodiments, the one or more electrical contacts are arranged in a current steering configuration. In any of the preceding embodiments, the one or more perforations are configured to promote biointegration with one or more of: the cochlear promontory, the one or more projections of the hypotympanum, the cavity within the round window niche, or the combination thereof within the middle ear cavity. In any of the preceding embodiments, the method further comprises a delivery configuration and an implantation configuration. In any of the preceding embodiments, the delivery configuration comprises a compressed state configured for delivery through either a facial recess or an external auditory canal. In any of the preceding embodiments, the implantation configuration comprises an expanded state when in the middle ear cavity. In any of the preceding embodiments, one or more projections comprising independent electrical contacts configured to stimulate tissue not directly underlying the energy delivery element. In any of the preceding embodiments, the one or more projections comprise one or more substrate extensions that comprise the independent electrical contacts. In any of the preceding embodiments, the one or more projections comprise insulated electrical conductors that electrically couple the independent electrical contacts to the substrate. In any of the preceding embodiments, the tissue not directly underlying the energy delivery element comprises one or more of: a round window, a eustachian tube, a hypotympanum, or a combination thereof. In any of the preceding embodiments, the element further comprises an array geometry to avoid mechanical interference with one or more tissues of the middle ear. In any of the preceding embodiments, the one or more tissues comprise an ossicular chain or an Eustachian tube. In any of the preceding embodiments, the array geometry comprises one or more concave or convex sections. In any of the preceding embodiments, the array geometry comprises a raised edge or perimeter. In any of the preceding embodiments, the element further comprises one or more ground electrodes configured to reduce or prevent current spread to a facial nerve or accessory nerves.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor, speech processor, external hardware components, and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "electrode" may include, and is contemplated to include, a plurality of electrodes. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method, comprising:

using an energy delivery element for stimulating a spiral ganglion of a cochlea from a middle ear cavity, wherein the energy delivery element comprises:

(i) a flexible substrate configured to conform to a curvature of one or more of: a cochlear promontory, one or more projections of a hypotympanum, a cavity within a round window niche, or a combination thereof within a middle ear cavity;

(ii) one or more electrical contacts coupled to the flexible substrate and configured to deliver electrical stimuli to activate a spiral ganglion of a basal turn of a cochlea; and (iii) characterized in that the energy delivery element further comprises one or more perforations defined by the flexible substrate and configured to promote long-term electrical contact with one or more of: the cochlear promontory, the one or more projections of the hypotympanum, the cavity within the round window niche, or the combination thereof within the middle ear cavity; and delivering the electrical stimuli to activate spiral ganglion of a cochlea from a middle ear cavity and for improving high-frequency hearing while preserving a residual low-frequency hearing.

2. The method of claim 1, wherein the improving high frequency hearing comprises improving hearing in a frequency range of about 2 kHz to about 8 kHz.

3. The method of claim 1, wherein the residual low-frequency hearing comprises having pure tone audiometric thresholds lower than about 70 dB in a frequency range of about 125 Hz to about 500 Hz.

4. The method of claim 1, further comprising implanting the energy delivery element, wherein the implanting comprises establishing electrical communication by adhesively attaching the energy delivery element to one or more tissues.

5. The method of claim 1, further comprising implanting the energy delivery element, wherein the implanting comprises establishing electrical communication by at least one of applying mechanical force to the energy delivery element against one or more tissues, or mechanically attaching the energy delivery element to one or more tissues.

6. The method of claim 1, further comprising confirming electrical communication between the energy delivery element and one or more tissues based on an impedance measurement.

7. The method of claim 1, wherein the delivering electrical stimuli comprises current steering with energy delivery element.

8. The method of claim 1, further comprising individualizing the electrical stimuli by mapping a position of the energy delivery element to a tonotopicity of the basal turn of the cochlea.

9. The method of claim 1, further comprising implanting the energy delivery element, wherein the implanting occurs without drilling a bone of the cochlear promontory.

* * * * *